(12) United States Patent
Caldwell et al.

(10) Patent No.: US 9,708,353 B2
(45) Date of Patent: Jul. 18, 2017

(54) HETEROBICYCLIC SPHINGOSINE 1-PHOSPHATE ANALOGS

(71) Applicant: BIOGEN MA INC., Cambridge, MA (US)

(72) Inventors: Richard D. Caldwell, Brookline, MA (US); Kevin Guckian, Northborough, MA (US); Gnanasambandam Kumaravel, Lexington, MA (US); Wen-Cherng Lee, Lexington, MA (US); Edward Yin-Shiang Lin, Ashland, MA (US); Xiaogao Liu, Dover, MA (US); Bin Ma, Arlington, MA (US); Daniel M. Scott, Weston, MA (US); Zhan Shi, Concord, MA (US); Jermaine Thomas, Chelsea, MA (US); Arthur G. Taveras, Boston, MA (US); Guo Zhu Zheng, Lexington, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 14/620,700

(22) Filed: Feb. 12, 2015

(65) Prior Publication Data

US 2015/0232492 A1 Aug. 20, 2015

Related U.S. Application Data

(62) Division of application No. 13/646,143, filed on Oct. 5, 2012, now Pat. No. 9,181,191, which is a division of application No. 12/588,882, filed on Oct. 30, 2009, now Pat. No. 8,349,849.

(60) Provisional application No. 61/109,720, filed on Oct. 30, 2008.

(51) Int. Cl.

| C07D 263/24 | (2006.01) |
|---|---|
| C07F 9/6512 | (2006.01) |
| C07C 233/47 | (2006.01) |
| C07C 229/36 | (2006.01) |
| C07C 217/58 | (2006.01) |
| C07D 215/20 | (2006.01) |
| C07F 9/60 | (2006.01) |
| C07D 239/80 | (2006.01) |

(52) U.S. Cl.
CPC ......... *C07F 9/6512* (2013.01); *C07C 217/58* (2013.01); *C07C 229/36* (2013.01); *C07C 233/47* (2013.01); *C07D 215/20* (2013.01); *C07D 239/80* (2013.01); *C07D 263/24* (2013.01); *C07F 9/60* (2013.01)

(58) Field of Classification Search
CPC .................................................. C07C 217/74
See application file for complete search history.

(56) References Cited

U.S. PATENT DOCUMENTS

| 5,041,639 | A | 8/1991 | Shroot et al. |
|---|---|---|---|
| 7,064,217 | B2 | 6/2006 | Macdonald et al. |
| 7,241,790 | B2 | 7/2007 | Lynch et al. |
| 7,560,477 | B2 | 7/2009 | Lynch et al. |
| 7,638,637 | B2 | 12/2009 | Lynch et al. |
| 7,786,173 | B2 | 8/2010 | Lynch et al. |
| 7,915,315 | B2 | 3/2011 | Lynch et al. |
| 8,349,849 | B2 * | 1/2013 | Caldwell ............... C07C 217/52 514/266.1 |
| 9,181,191 | B2 * | 11/2015 | Caldwell ............... C07C 217/74 514/311 |
| 2008/0027036 | A1 | 1/2008 | Burli et al. |
| 2009/0042955 | A1 | 2/2009 | Lynch et al. |
| 2009/0253759 | A1 | 10/2009 | Lynch et al. |
| 2009/0253760 | A1 | 10/2009 | Lynch et al. |
| 2010/0240617 | A1 | 9/2010 | Lynch et al. |

FOREIGN PATENT DOCUMENTS

| WO | WO-2007/092638 A1 | 8/2007 |
|---|---|---|
| WO | WO-2009/023854 A1 | 2/2009 |
| WO | WO-2010/051030 A1 | 5/2010 |
| WO | WO-2011/017561 A1 | 2/2011 |

OTHER PUBLICATIONS

International Preliminary Report on Patentability issued in International Patent Application No. PCT/US2009/005898, dated: May 3, 2011.
Silverman; "II. Drug Development: Lead Modification"; The Organic Chemistry of Drug Design and Drug Action; Academic Press Inc.; pp. 15-22 (1992).
Vippagunta et al.; "Crystalline solids"; Advanced Drug Delivery Reviews; 48:3-26 (2001).

* cited by examiner

*Primary Examiner* — Paul V Ward
(74) *Attorney, Agent, or Firm* — McCarter & English, LLP; Steven G. Davis; Xin Zhang

(57) ABSTRACT

Compounds that have agonist activity at one or more of the S1P receptors are provided. The compounds are sphingosine analogs that, after phosphorylation, can behave as agonists at S1P receptors.

29 Claims, 7 Drawing Sheets

HETEROBICYCLIC SPHINGOSINE 1-PHOSPHATE ANALOGS

CLAIM OF PRIORITY

This application is a divisional application of U.S. patent application Ser. No. 13/646,143, filed on Oct. 5, 2012; which is a divisional application of U.S. patent application Ser. No. 12/588,882, filed on Oct. 30, 2009, now U.S. Pat. No. 8,349,849, issued on Jan. 8, 2013; which claims priority to U.S. Provisional Patent Application No. 61/109,720, filed on Oct. 30, 2008. All applications are incorporated by reference in their entirety.

BACKGROUND

Sphingosine 1-phosphate (S1P) is a lysophospholipid mediator that evokes a variety of cellular responses by stimulation of five members of the endothelial cell differentiation gene (EDG) receptor family. The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. Ultimately, this S1P-driven signaling results in cell survival, increased cell migration and, often, mitogenesis. The recent development of agonists targeting S1P receptors has provided insight regarding the role of this signaling system in physiologic homeostasis. For example, the immunomodulator, FTY720 (2-amino-2-[2-(4-octylphenyl)ethyl]propane 1,3-diol), that following phosphorylation, is an agonist at 4 of 5 S1P receptors, revealed that enhancing S1P tone influences lymphocyte trafficking. Further, S1P type 1 receptor ($S1P_1$) antagonists cause leakage of the lung capillary endothelium, which suggests that S1P may be involved in maintaining the integrity of the endothelial barrier in some tissue beds.

S1P has been demonstrated to induce many cellular processes, including those that result in platelet aggregation, cell proliferation, cell morphology, tumor-cell invasion, endothelial cell chemotaxis and angiogenesis. For these reasons, S1P receptors are good targets for therapeutic applications such as wound healing and tumor growth inhibition.

Sphingosine-1-phosphate signals cells in part via a set of G protein-coupled receptors named $S1P_1$, $S1P_2$, $S1P_3$, $S1P_4$, and $S1P_5$ (formerly EDG1, EDG5, EDG3, EDG6 and EDG8). The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. These receptors share 50-55% amino acid sequence identity and cluster with three other receptors ($LPA_1$, $LPA_2$, and $LPA_3$ (formerly EDG2, EDG4 and EDG7) for the structurally related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit and each subunit can then associate with effector proteins, which activate second messengers leading to a cellular response. Eventually the GTP on the G-proteins is hydrolyzed to GDP and the subunits of the G-proteins reassociate with each other and then with the receptor. Amplification plays a major role in the general GPCR pathway. The binding of one ligand to one receptor leads to the activation of many G-proteins, each capable of associating with many effector proteins leading to an amplified cellular response.

S1P receptors make good drug targets because individual receptors are both tissue and response specific. Tissue specificity of the S1P receptors is desirable because development of an agonist or antagonist selective for one receptor localizes the cellular response to tissues containing that receptor, limiting unwanted side effects. Response specificity of the SIP receptors is also of importance because it allows for the development of agonists or antagonists that initiate or suppress certain cellular responses without affecting other responses. For example, the response specificity of the S1P receptors could allow for an S1P mimetic that initiates platelet aggregation without affecting cell morphology.

Sphingosine-1-phosphate is formed as a metabolite of sphingosine in its reaction with sphingosine kinase and is stored in abundance in the aggregates of platelets where high levels of sphingosine kinase exist and sphingosine lyase is lacking. S1P is released during platelet aggregation, accumulates in serum, and is also found in malignant ascites. Reversible biodegradation of S1P most likely proceeds via hydrolysis by ectophosphohydrolases, specifically the sphingosine 1-phosphate phosphohydrolases. Irreversible degradation of SIP catalyzed by S1P lyase yielding ethanolamine phosphate and hexadecenal.

A class of S1P agonist compounds are described in provisional U.S. Application No. 60/956,111, filed Aug. 15, 2007, and PCT/US2008/073378, filed Aug. 15, 2008, each of which is incorporated by reference in its entirety.

SUMMARY

Currently, there is a need for novel, potent, and selective agents that are agonists of the S1P receptor having enhanced potency, selectivity, and oral bioavailability. In addition, there is a need in the art for identification of, as well as the synthesis and use of, such compounds.

In one aspect, a compound of formula (I):

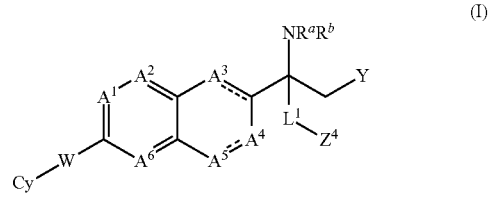

in which $A^1$ can be —$C(X^1)$=, —N=, —O—, —S—, or a bond; $A^2$ can be —$C(X^2)$=, —N=, —O—, —S—, or a bond; $A^3$ can be —$C(X^3)(X^{3'})$—, —$C(X^3)$=, —$NX^3$—, —N=, —O—, or —S—; $A^4$ is —$C(X^4)(X^{4'})$—, —$C(X^4)$=, —$NX^4$—, —N=, —O—, or a bond; $A^5$ can be —$C(X^5)$ ($X^{5'}$)—, —$C(X^5)$=, —$NX^5$—, —N=, —O—, or —S—; and $A^6$ can be —$C(X^6)$=, —N=, —O—, —S—, or a bond; provided that $A^1$, $A^2$, $A^3$, $A^4$, $A^5$ and $A^6$ are not simultaneously —$C(X^1)$=, —$C(X^2)$=, —$C(X^3)$=, —$C(X^4)$=, —$C(X^5)$=, and —$C(X^6)$= respectively, and provided that the bicyclic ring includes 0-3 heteroatoms; and further provided that no more than one of $A^1$, $A^2$, and $A^6$ is a bond.

Each of $X^1$, $X^2$, $X^3$, $X^{3'}$, $X^4$, $X^{4'}$, $X^5$, $X^{5'}$, and $X^6$, independently, can be hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —$NR^fR^g$, —$N(R^f)SO_2R^g$, —$SO_2R^f$, —$SO_2NR^fR^g$, —$CO_2R^f$, trialkylamino, aryl, or heteroaryl.

Y can be —OR$^f$, —(CR$^f$R$^g$)OR$^f$, —(CR$^f$R$^g$)$_2$OR$^f$, —O—P(O)(OR$^f$)OR$^g$, —OC(O)R$^c$, —C(O)OR$^c$, —(CR$^f$R$^g$)—P(O)(OR$^f$)OR$^g$, —(C(OH)R$^f$)—P(O)(OR$^f$)OR$^g$, —S—P(O)(OR$^f$)OR$^g$, tetrazole, —SO$_2$NHR$^f$, —SO$_3$, —CONHR$^f$, —Si(OH)$_2$, or —B(OH)$_2$.

W can be —CR$^f$R$^g$—, —NR$^f$—, —O—, —S—, —SO—, or —SO$_2$—.

Cy can be cycloalkyl, cycloalkenyl, heterocyclyl, aryl, or heteroaryl; wherein Cy is optionally substituted by 1-6 substituents selected from the group consisting of hydrogen, halo, hydroxy, nitro, cyano, —NR$^f$R$^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, haloalkoxy, cycloalkylalkoxy, cycloalkenylalkoxy, heterocyclylalkoxy, aryloxy, arylalkoxy, heteroaryloxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, and heteroaryl.

L$^1$ can be —CH$_2$—, —CHF—, or —CF$_2$—.

Z$^4$ can be hydrogen, halo, alkyl, haloalkyl, alkenyl, haloalkenyl, alkynyl, or —OR$^f$; or Z$^4$ can be —CH$_2$— bound to the carbon atom to which Y is bound; or L$^1$, Z$^4$, Y, and the atoms to which they are bound can form a 4-7 membered cycloalkyl group or a 4-7 membered heterocyclyl group having 1 or 2 heteroatoms selected from O and N.

R$^a$ can be hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl.

R$^b$ can be hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl. In some circumstances, R$^b$ and Z$^4$ are taken to together to form —C(O)O— or =C(R$^f$)O—.

R$^c$ can be alkyl, aryl, trifluoromethyl, methylsulfonyl, trifluoromethylsulfonyl, p-tolylsulfonyl, or a group selected such that —OCOR$^c$ is a good leaving group;

Each R$^f$, independently, is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl.

Each R$^g$, independently, is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl.

The compound can be in the form of a pharmaceutically acceptable salt or prodrug.

In some embodiments, W is —O—. R$^a$ and R$^b$, independently, can each be H or alkyl. Y can be —OR$^f$, or in some circumstances, Y can be —OH or —O—P(O)(OR$^f$)OR$^g$. X$^6$ can be H, halo, alkyl, cycloalkyl, or haloalkyl.

Simultaneously, A$^3$ can be —C(X$^3$)H—, A$^4$ can be —C(X$^4$)H—, and A$^5$ can be —C(X$^5$)H—.

In some embodiments, Cy has the formula:

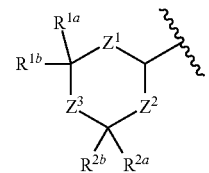

in which Z$^1$ is a bond, —[C(R$^d$R$^e$)]$_x$—, —CR$^d$=CR$^e$—, —O—, —NR$^f$—; Z$^2$ is a bond, —[C(R$^d$R$^e$)]$_y$—, —CR$^d$=CR$^e$—, —O—, —NR$^f$—; Z$^3$ is a bond, —[C(R$^d$R$^e$)]$_z$—, —CR$^d$=CR$^e$—, —O—, —NR$^f$—; and each of x, y, and z, independently, is 1 to 3.

Each R$^d$, independently, can be H, halo, hydroxy, alkyl, haloalkyl, alkenyl, alkoxy, cycloalkyl, —C(O)NR$^f$R$^g$, —NR$^f$R$^g$, —NR$^f$C(O)R$^g$, or —SO$_2$NR$^f$R$^g$.

Each R$^e$, independently, can be H, halo, hydroxy, alkyl, haloalkyl, alkenyl, alkoxy, cycloalkyl, —C(O)NR$^f$R$^g$, —NR$^f$R$^g$, —NR$^f$C(O)R$^g$, or —SO$_2$NR$^f$R$^g$.

R$^{1a}$ and R$^{1b}$, independently, can be hydrogen, halo, hydroxy, nitro, cyano, —NR$^f$R$^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl. In some circumstances, R$^{1a}$ and R$^{1b}$, when taken together, can be C$_2$-C$_5$ alkylene optionally terminated by or interrupted by 1 or 2 oxygen atoms, or C$_2$-C$_5$ alkenylene optionally terminated by or interrupted by 1 or 2 oxygen atoms.

R$^{2a}$ and R$^{2b}$, independently, can be hydrogen, halo, hydroxy, nitro, cyano, —NR$^f$R$^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl. In some circumstances, R$^{1a}$ and R$^{2a}$, when taken together, can be C$_1$-C$_5$ alkylene optionally terminated by or interrupted by 1 or 2 oxygen atoms, or C$_2$-C$_5$ alkenylene optionally terminated by or interrupted by 1 or 2 oxygen atoms.

R$^{1a}$, R$^{1b}$, R$^{2a}$, and R$^{2b}$ can each, independently, be substituted with 0-5 substituents selected from halo, hydroxy, nitro, cyano, —NR$^f$R$^g$, or —CO$_2$R$^f$.

In some embodiments, R$^{1a}$ and R$^{2a}$ can both be hydrogen. Z$^1$ can be —CH$_2$CH$_2$—. Z$^2$ can be —CH$_2$—. Z$^3$ can be a bond.

R$^{1b}$ can be fluoro, chloro, bromo, iodo, methyl, difluoromethyl, triflurormethyl, ethyl, 1,1-difluoroethyl, propyl, isopropyl, n-butyl, i-butyl, t-butyl, n-pentyl, isopentyl, 1,1-dimethylpropyl, neopentyl, cyclopentyl, n-hexyl, cyclohexyl, methoxy, trifluoromethoxy, ethoxy, n-propoxy, i-propoxy, n-butoxy, i-butoxy, t-butoxy, n-pentyloxy, i-pentyloxy, 1,1-dimethylpropoxy, neopentyloxy, cyclopentyloxy, n-hexyloxy, or cyclohexyloxy.

In another aspect, a compound of formula (II):

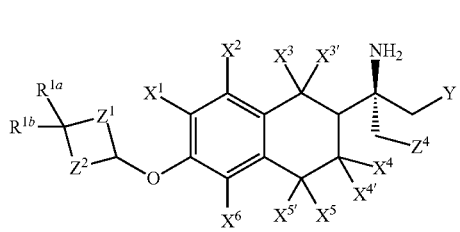

(II)

in which each of $X^1$, $X^2$, $X^3$, $X^{3'}$, $X^4$, $X^{4'}$, $X^5$, $X^{5'}$, $X^6$, Y, and $Z^4$ are as defined for formula (I).

$R^{1a}$ and $R^{1b}$, independently, can each be hydrogen, halo, hydroxy, nitro, cyano, —$NR^fR^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl.

$R^{1a}$ and $R^{1b}$, when taken together, can be $C_2$-$C_5$ alkylene optionally terminated by or interrupted by 1 or 2 oxygen atoms, or $C_2$-$C_5$ alkenylene optionally terminated by or interrupted by 1 or 2 oxygen atoms.

$Z^1$ can be a bond, —$[C(R^dR^e)]_x$—, or —$CR^d$=$CR^e$—; $Z^2$ can be a bond, —$[C(R^dR^e)]_y$—, or —$CR^d$=$CR^e$—; and each of x and y, independently, can be 1 to 3.

Each $R^d$, independently, can be H, halo, hydroxy, alkyl, alkenyl, alkoxy, or cycloalkyl. Each $R^e$, independently, can be H, halo, hydroxy, alkyl, alkenyl, alkoxy, or cycloalkyl. The compound can be in the form of a pharmaceutically acceptable salt or prodrug.

Y can be —$OR^f$, or in some circumstances, Y can be —OH or —O—$P(O)(OR^f)OR^g$. $X^6$ can be an electron withdrawing group, or in some circumstances, $X^6$ can be H, halo, alkyl, cycloalkyl, or haloalkyl. $Z^1$ can be —$CH_2CH_2$—, and $Z^2$ can be —$CH_2CH_2$—. $R^{1a}$ can be hydrogen, halo, hydroxy, alkyl, haloalkyl, cycloalkyl, cycloalkylalkyl, arylalkyl, alkoxy, cycloalkylalkoxy, arylalkoxy, or aryl. Simultaneously, Y can be —OH or —$OP(O)(OH)_2$; $Z^4$ can be H or —OH; $X^1$, $X^2$, $X^3$, $X^4$, and $X^5$ can each be H; $X^{3'}$, $X^{4'}$, and $X^{5'}$ can each be H; and $X^6$ can be halo, alkyl, cycloalkyl, or haloalkyl.

$Z^1$ can be —$(CH_2)_x$— and $Z^2$ can be —$(CH_2)_y$—. $R^{1a}$ can be alkyl, haloalkyl, cycloalkyl, aryl, or arylalkoxy. The compound of formula (II) having the formula:

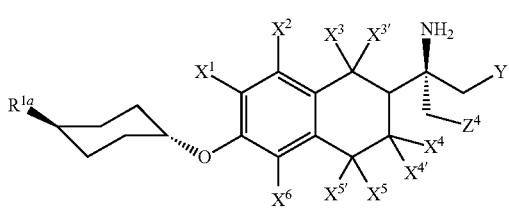

i.e., where $R^{1a}$ and the oxygen atom bound to the cyclohexyl ring are in the trans-orientation with respect to one another.

In another aspect, a compound can have formula (IV):

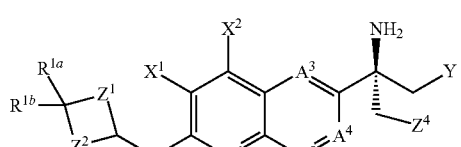

(IV)

in which each of $X^1$, $X^2$, $X^3$, $X^{3'}$, $X^4$, $X^{4'}$, $X^5$, $X^{5'}$, $X^6$, Y, and $Z^4$ are as defined for formula (I).

In formula (IV), $A^3$ can be —N=, $A^4$ can be —$C(R^4)$=, $A^5$ can be —$C(R^5)$=, and $A^6$ can be —$C(R^6)$=. Or $A^3$ can be —$C(R^3)$=, $A^4$ can be —N=, $A^5$ can be —$C(R^5)$=, and $A^6$ can be —$C(R^6)$=. Or, $A^3$ can be —$C(R^3)$=, $A^4$ can be —$C(R^4)$=, $A^5$ can be —N=, and $A^6$ can be —$C(R^6)$=. Or, $A^3$ can be —$C(R^3)$=, $A^4$ can be —$C(R^4)$=, $A^5$ can be —$C(R^5)$=, and $A^6$ can be —N=. Or, $A^3$ can be —N=, $A^4$ can be —N=, $A^5$ can be —$C(R^5)$=, and $A^6$ can be —$C(R^6)$=.

$R^{1a}$ and $R^{1b}$, independently, can each be hydrogen, halo, hydroxy, nitro, cyano, —$NR^fR^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl.

$R^{1a}$ and $R^{1b}$, when taken together, can be $C_2$-$C_5$ alkylene optionally terminated by or interrupted by 1 or 2 oxygen atoms, or $C_2$-$C_5$ alkenylene optionally terminated by or interrupted by 1 or 2 oxygen atoms.

$Z^1$ can be a bond, —$[C(R^dR^e)]_x$—, or —$CR^d$=$CR^e$—; $Z^2$ can be a bond, —$[C(R^dR^e)]_y$—, or —$CR^d$=$CR^e$—; and each of x and y, independently, can be 1 to 3.

Each $R^d$, independently, can be H, halo, hydroxy, alkyl, alkenyl, alkoxy, or cycloalkyl. Each $R^e$, independently, can be H, halo, hydroxy, alkyl, alkenyl, alkoxy, or cycloalkyl. The compound can be in the form of a pharmaceutically acceptable salt or prodrug.

In another aspect, a pharmaceutical composition includes a pharmaceutically acceptable carrier and a compound of formula (I) as defined above.

In another aspect, a method of making a compound of formula (I) comprising contacting a compound of formula (III):

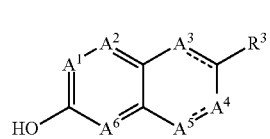

(III)

with a compound having the formula: Cy-OH.

In formula (III), each of $A^1$, $A^2$, $A^3$, $A^4$, $A^5$, and $A^6$, are as defined for formula (I). $R^3$ can have the formula:

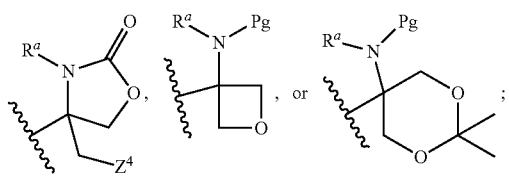

in which $Z^4$ is H or —$OR^f$ (where $R^f$ is as defined in formula (I)); $R^a$ is as defined in formula (I); and Pg is an amino protecting group.

In the compound have the formula Cy-OH, Cy can be cycloalkyl, cycloalkenyl, heterocyclyl, aryl, or heteroaryl; wherein Cy is optionally substituted by 1-6 substituents selected from the group consisting of hydrogen, halo, hydroxy, nitro, cyano, —$NR^fR^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, haloalkoxy, cycloalkylalkoxy, cycloalkenylalkoxy, heterocyclylalkoxy, aryloxy, arylalkoxy, heteroaryloxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, and heteroaryl. $R^f$ and $R^g$ are as defined for formula (I).

In another aspect, a method for prevention or treatment of a pathological condition or symptom in a mammal, wherein the activity of sphingosine 1-phosphate receptors is implicated and agonism of such activity is desired, includes administering to said mammal an effective amount of a compound of formula (I).

The pathological condition can be neuropathic pain. The pathological condition can be an autoimmune disease. The method can include administering to said mammal an effective amount of a drug selected from the group consisting of: corticosteroids, bronchodilators, antiasthmatics, antiinflammatories, antirheumatics, immunosuppressants, antimetabolites, immunomodulators, antipsoriatics, and antidiabetics. The autoimmune disease is uveitis, type I diabetes, rheumatoid arthritis, inflammatory bowel diseases, lupus, asthma, psoriasis, or multiple sclerosis.

The prevention or treatment of the pathological condition can include altering lymphocyte trafficking. Altering lymphocyte trafficking can provide prolonged allograft survival. The allograft can be for transplantation.

In another aspect, a method for prevention or treatment of a pathological condition or symptom in a mammal, wherein the activity S1P lyase implicated and inhibition of the SIP lyase is desired, includes administering to said mammal an effective amount of a compound of formula (I).

In another aspect, an assay includes transfecting HEK293 cells with a plasmid encoding sphingosine kinase 2, obtaining a soluble cell lysate including sphingosine kinase 2, contacting the soluble cell lysate with ATP and a test compound, and determining whether the test compound is phosphorylated.

The details of one or more embodiments are set forth in the accompanying description below. Other features, objects, and advantages will be apparent from the description and drawings, and from the claims.

DETAILED DESCRIPTION

Figure 1:
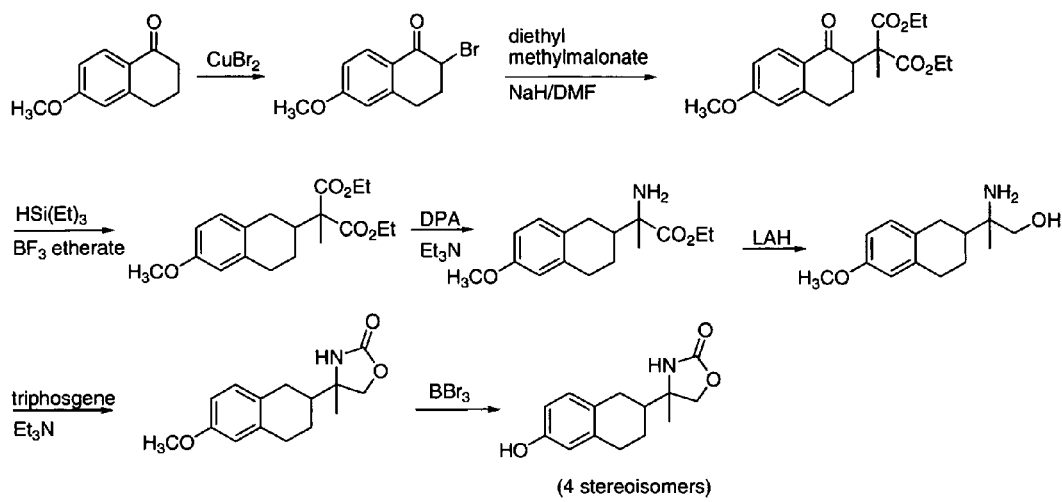
FIG. 1 is a schematic depiction of a synthesis of an intermediate useful in the preparation of compounds of Formula (I).

The following abbreviations are used herein: S1P, sphingosine-1-phosphate; $S1P_{1-5}$ SIP receptor types; GPCR, G-protein coupled receptor; SAR, structure-activity relationship; EDG, endothelial cell differentiation gene; EAE, experimental autoimmune encephalomyelitis; NOD non-obese diabetic; TNFα, tumor necrosis factor alpha; HDL, high density lipoprotein; and RT-PCR, reverse transcriptase polymerase chain reaction.

The values listed below for radicals, substituents, and ranges, are for illustration only; they do not exclude other defined values or other values within defined ranges for the radicals and substituents. The disclosed compounds include compounds of formula I having any combination of the values, specific values, more specific values, and preferred values described herein.

The term "halogen" or "halo" includes bromo, chloro, fluoro, and iodo. The term "haloalkyl", refers to an alkyl radical bearing at least one halogen substituent, non-limiting examples include, but are not limited to, chloromethyl, fluoroethyl, trichloromethyl, trifluoromethyl and the like.

The term "$C_1$-$C_{20}$ alkyl" refers to a branched or linear alkyl group having from one to twenty carbons. Non-limiting examples include, but are not limited to, methyl, ethyl, n-propyl, iso-propyl, butyl, iso-butyl, sec-butyl, tert-butyl, pentyl, hexyl, heptyl, octyl and the like.

The term "$C_2$-$C_{20}$ alkenyl", refers to an olefinically unsaturated branched or linear group having from two to twenty carbon atoms and at least one double bond. Typically, $C_2$-$C_{20}$ alkenyl groups include, but are not limited to, 1-propenyl, 2-propenyl, 1,3-butadienyl, 1-butenyl, hexenyl, pentenyl, hexenyl, heptenyl, octenyl and the like.

The term ($C_2$-$C_{20}$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl, and the like.

The term "($C_1$-$C_{10}$)alkoxy" refers to an alkyl group attached through an oxygen atom. Examples of ($C_1$-$C_{10}$) alkoxy can be methoxy, ethoxy, propoxy, isopropoxy, butoxy, iso-butoxy, sec-butoxy, pentoxy, 3-pentoxy, or hexyloxy and the like.

The term "$C_3$-$C_{12}$ cycloalkyl" refers to a cyclic alkyl group, such as, for example, cyclopropyl, cyclobutyl, cyclopentyl, cyclohexyl, cycloheptyl, cyclooctyl and the like. Cyloalkyl groups include bicyclic groups such as decalinyl, bridged bicyclic groups such as norbornyl and bicyclo[2.2.2] octyl, tricyclic, bridged tricyclic such as adamantyl, and spiro-linked bicyclic or tricyclic groups.

The term "($C_6$-$C_{14}$)aryl" refers to a monocyclic, bicyclic, or tricyclic carbocyclic ring system having one or two aromatic rings including, but not limited to, phenyl, benzyl, naphthyl, tetrahydronaphthyl, indanyl, indenyl, anthracyl, and the like.

The term "aryl($C_1$-$C_{20}$)alkyl" or "arylalkyl" or "aralkyl" refers to an alkyl group substituted with a mono or bicyclic carbocyclic ring system having one or two aromatic rings including, a group such as phenyl, naphthyl, tetrahydronaphthyl, indanyl, indenyl, and the like. Non-limiting examples of arylalkyl include benzyl, phenylethyl, and the like.

The term "($C_1$-$C_{14}$)heterocyclic group" refers to an optionally substituted mono- or bicyclic carbocyclic ring system containing one, two, three, or four heteroatoms (optionally in each ring) wherein the heteroatoms are oxygen, sulfur, and nitrogen.

The term "($C_4$-$C_{14}$)heteroaryl" refers to an optionally substituted mono- or bicyclic cyclic ring system containing one, two, or three heteroatoms (optionally in each ring) wherein the heteroatoms are oxygen, sulfur, and nitrogen. Non-limiting examples of heteroaryl groups include furyl, thienyl, pyridyl, and the like.

The term "phosphate analog" and "phosphonate analog" comprise analogs of phosphate and phosphonate wherein the phosphorous atom is in the +5 oxidation state and one or more of the oxygen atoms is replaced with a non-oxygen moiety, including for example, the phosphate analogs phosphorothioate, phosphorodithioate, phosphoroselenoate, phosphorodiselenoate, phosphoroanilothioate, phosphoranilidate, phosphoramidate, boronophosphates, and the like, including associated counterions, e.g., $H^+$, $NH_4^+$, $Na^+$, $K^+$, and the like if such counterions are present.

The term "alpha-substituted phosphonate" includes phosphonate (—$CH_2PO_3H_2$) groups that are substituted on the alpha-carbon such as —$CHFPO_3H_2$, —$CF_2PO_3H_2$, —$CHOHPO_3H_2$, —$C=OPO_3H_2$) and the like.

The term "pharmaceutically acceptable carrier" includes any of the standard pharmaceutical carriers, such as a phosphate buffered saline solution, hydroxypropyl beta-cyclodextrins (HO-propyl beta cyclodextrins), water, emulsions such as an oil/water or water/oil emulsion, and various types of wetting agents. The term also encompasses any of the agents approved by a regulatory agency of the U.S. Federal government or listed in the U.S. Pharmacopeia for use in animals, including humans.

The term "pharmaceutically acceptable salt or prodrug" refers to salts which retain the biological effectiveness and properties of the disclosed compounds and which are not biologically or otherwise undesirable. In many cases, the disclosed compounds are capable of forming acid or base salts by virtue of the presence of amino or carboxyl groups or groups similar thereto. "Prodrug" refers to a compound that can hydrolyze, oxidize, be phosphorylated, or otherwise react under biological conditions (in vitro or in vivo) to provide a compound in pharmacologically active form. In the present context, a compound of Formula (I) can be pharmacologically active (e.g., function as an S1P receptor agonist) when group Y includes, for example, a phosphate group. Suitable prodrugs can therefore include phosphate esters (hydrolyzed to the corresponding phosphate), alcohols (phosphorylated to the corresponding phosphate), esters (hydrolyzed to produce an alcohol, which is phosphorylated to the corresponding phosphate), oxetanes (e.g., where $L^1$, $Z^4$, Y, and the atoms to which they are bound form an oxetane ring; the oxetane can be hydrolyzed to produce an alcohol, which is phosphorylated to the corresponding phosphate) and other compounds that can be converted to a pharmacologically active form.

An "effective amount" means an amount sufficient to produce a selected effect. For example, an effective amount of an S1P receptor agonist is an amount that decreases the cell signaling activity of the S1P receptor.

The disclosed compounds can contain one or more asymmetric centers in the molecule. In accordance with the present disclosure any structure that does not designate the stereochemistry is to be understood as embracing all the various optical isomers, as well as racemic mixtures thereof.

The disclosed compounds may exist in tautomeric forms and the invention includes both mixtures and separate individual tautomers. For example, the following structure:

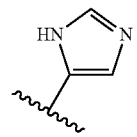 [SMILES: *c1cnc[nH]1]

is understood to represent a mixture of the structures:

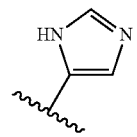 [SMILES: *c1cnc[nH]1]

as well as

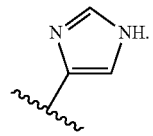 [SMILES: *c1c[nH]cn1]

Figure 3:
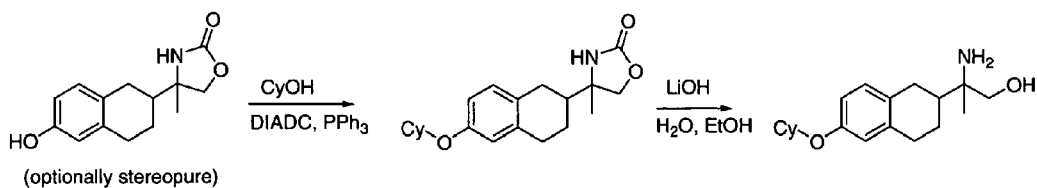
FIG. 3 is a schematic depiction of a synthesis of compounds of Formula (I).

FIGS. 1 and 3 illustrate schematically a synthetic route to certain compounds of Formula (I), starting from 6-methoxy-1-tetralone. First the 2-position is modified by bromination and diethyl methylmalonate. Reduction converts the oxo group to a methylene group. Amination and a further reduction affords the beta amino alcohol, which is protected as a cyclic carbamate. Then the 6-hydroxy group is unmasked. At this point, the different stereoisomers may be separated (e.g., by chiral chromatography), so that further steps can be carried out using substantially stereopure materials. A Mitsunobu reaction can be used to install the Cy group. Finally, the cyclic carbamate protection is reversed to afford the final product.

Figure 4:
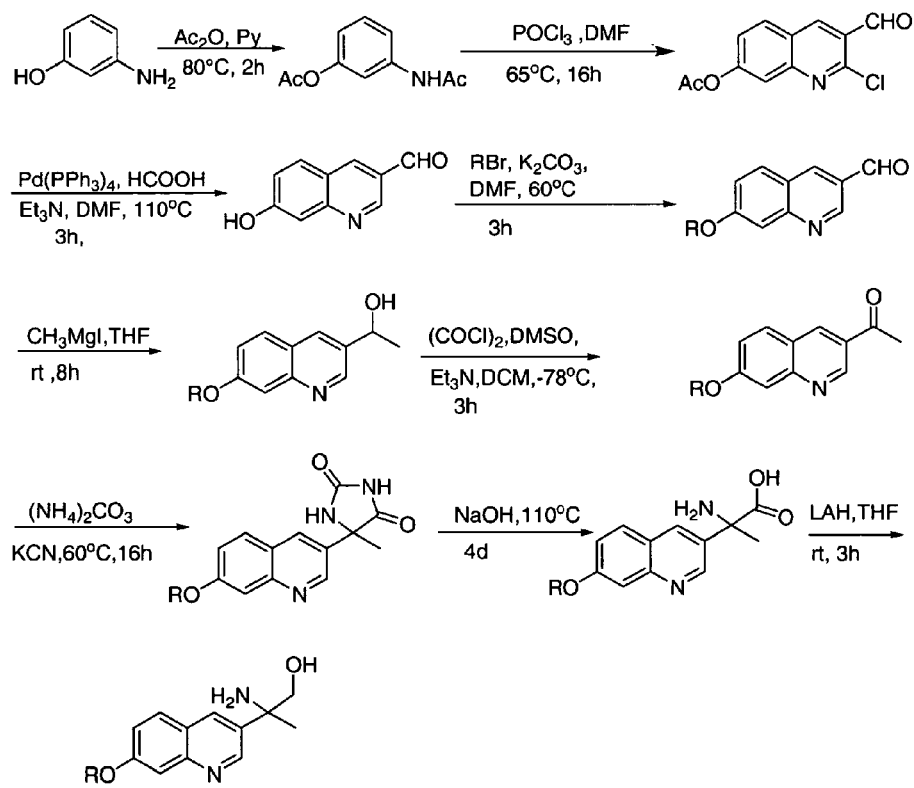
FIGS. 4-10 are schematic depictions of syntheses of compounds of Formula (I).
Figure 5:
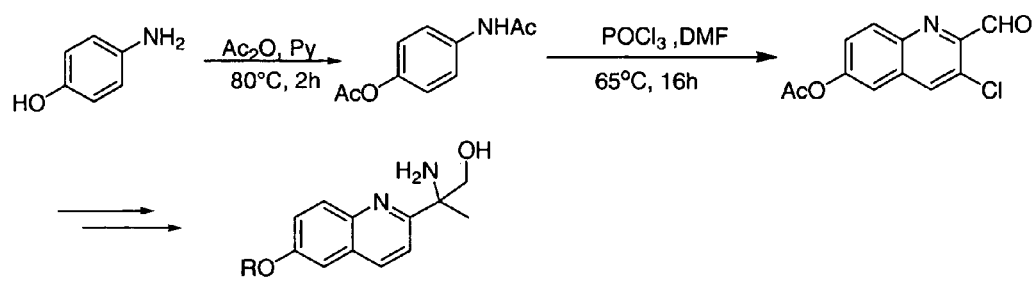
Figure 6:
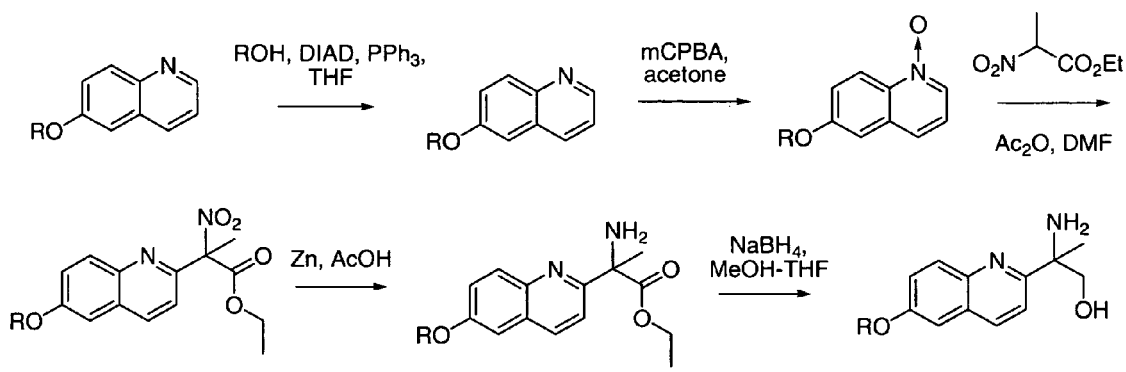
Figure 7:
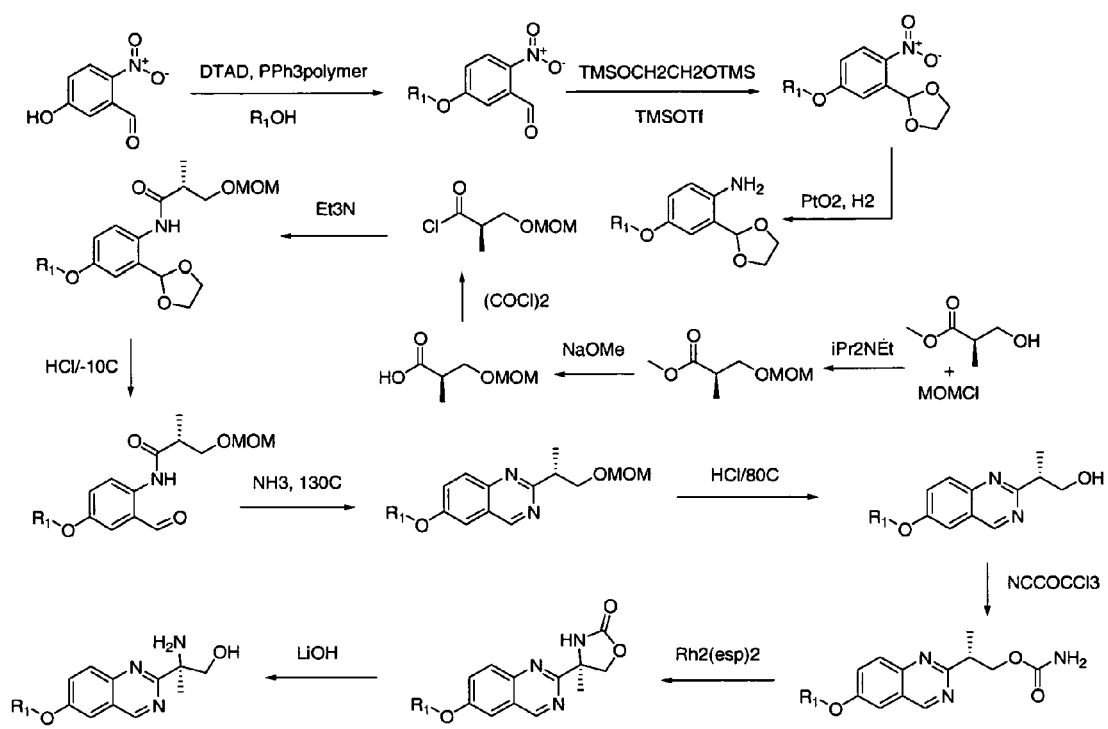

FIGS. 4 and 5 illustrate schematically a synthetic route to certain compounds of Formula (I), starting from m-aminophenol or p-aminophenol. Briefly, the starting material is acetylated and subsequently oxidized to afford 7-acetoxy-2-chloroquinoline-3-carbaldehyde (starting from m-aminophenol, FIG. 4) or 6-acetoxy-3-chloroquinoline-2-carbaldehyde (starting from p-aminophenol, FIG. 5). The acetoxy group is deprotected and the chloro group replaced by H. The resulting alcohol can be alkylated at this stage, for example using an alkyl halide. Next a Gringnard reaction followed by an oxidation affords a ketone. The ketone is reacted with ammonium carbonate, hydrolyzed, and reduced, to give the final product, a 2-amino-2-(7-alkoxy-quinolin-3-yl)-1-propanol as a mixture of stereoisomers. If desired, the stereoisomers may be separated, for example by chiral chromatography.

Figure 8:
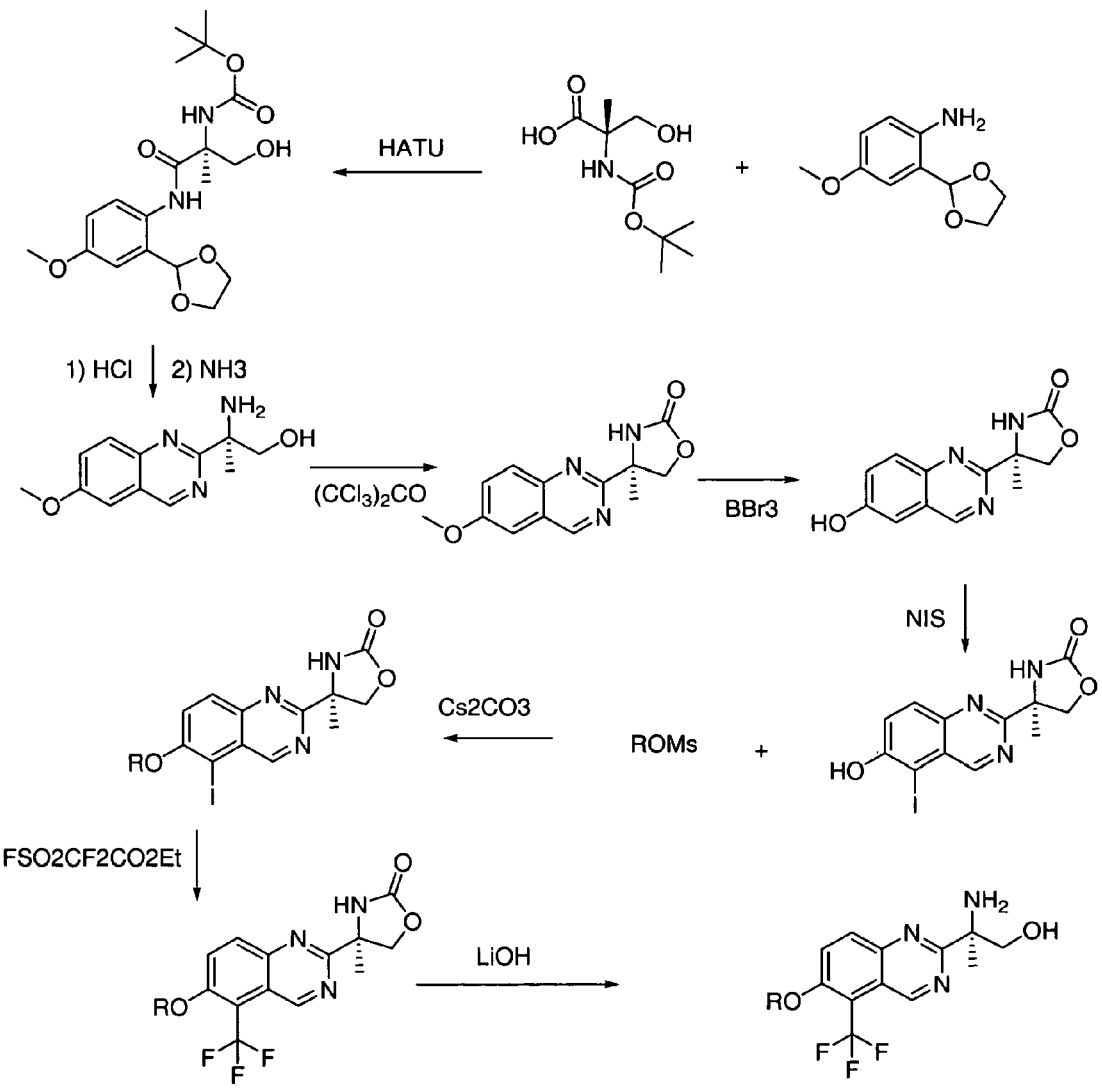
Figure 9:
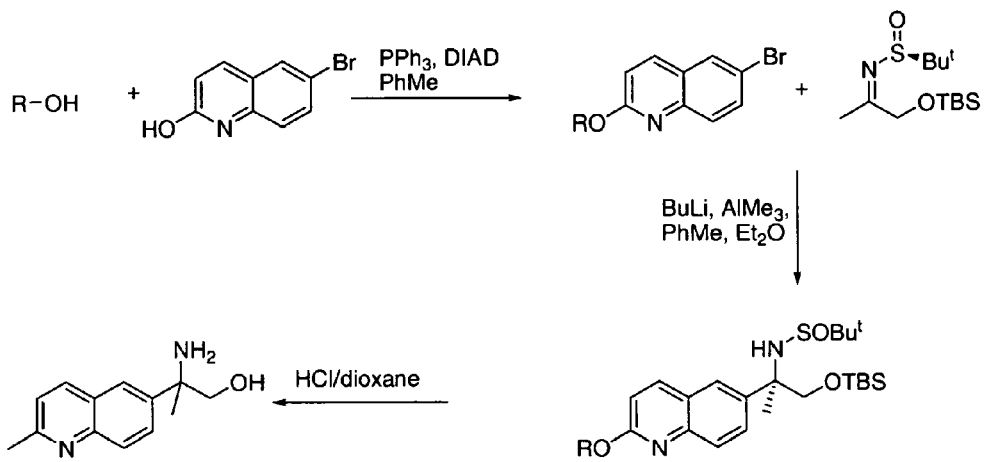
Figure 10:
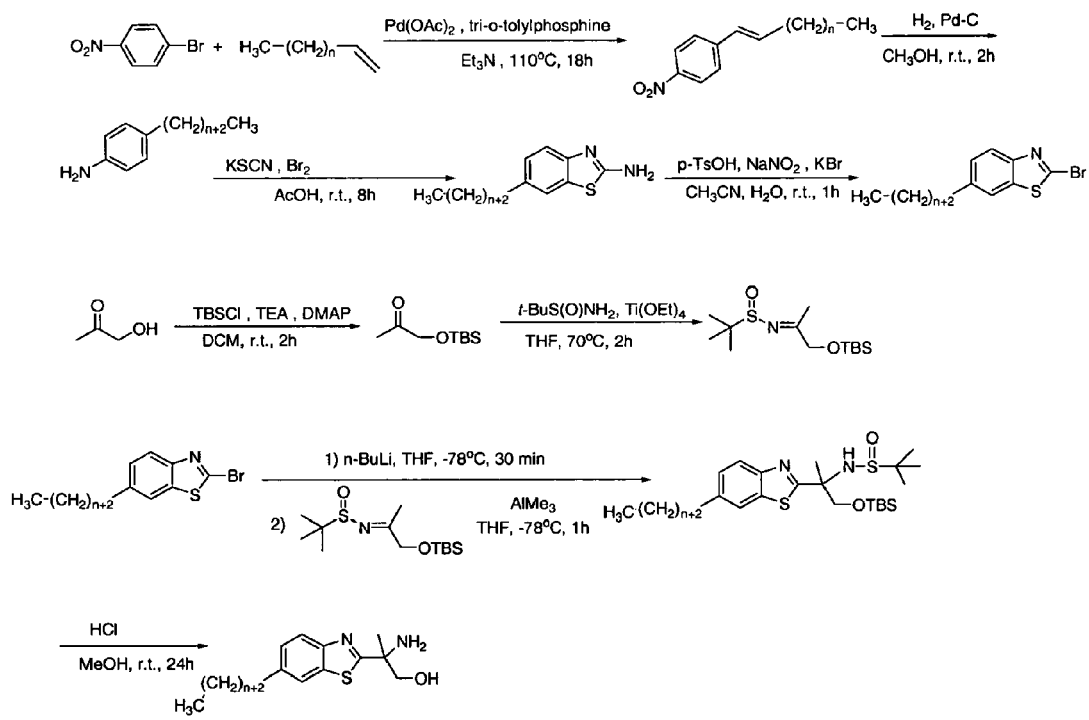

FIGS. 6-10 illustrate schematically synthetic routes to certain compounds of Formula (I), e.g., quinolines (FIGS. 6 and 9), quinazolines (FIGS. 7-8) and benzothiazoles (FIG. 10).

An "S1P modulating agent" refers a compound or composition that is capable of inducing a detectable change in S1P receptor activity in vivo or in vitro (e.g., at least 10% increase or decrease in S1P activity as measured by a given assay such as the bioassay described in the examples and known in the art. "S1P receptor," refers to all of the S1P receptor subtypes (for example, the S1P receptors $S1P_1$, $S1P_2$, $S1P_3$, $S1P_4$, and $S1P_5$), unless the specific subtype is indicated.

It will be appreciated by those skilled in the art that the disclosed compounds having chiral centers may exist in and be isolated in optically active and racemic forms. It is to be understood that the disclosed compounds encompass any racemic, optically active or stereoisomeric form, or mixtures thereof. It is well known in the art how to prepare such optically active forms (for example, resolution of the racemic form by recrystallization techniques, synthesis from optically-active starting materials, by chiral synthesis, or chromatographic separation using a chiral stationary phase) and how to determine S1P agonist activity using the standard tests described herein, or using other similar tests which are well known in the art. In addition, some compounds may exhibit polymorphism.

In some embodiments, the carbon atom labeled with a * in Formula (I) below can be a stereogenic center.

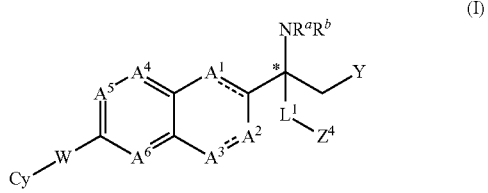

(I)

In such embodiments, there can be a preferred stereochemical configuration. For example, when $L^2$ is a bond, $L^1$ is —$CH_2$—, $Z^4$ is H, and Y is —OH, the preferred configuration is the R configuration:

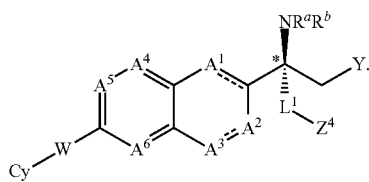

Potential uses of an S1P receptor agonist, and $S1P_1$ receptor type selective agonists particularly, include, but are not limited to, altering lymphocyte trafficking as a method of treatment for neuropathic pain, inflammation-induced pain (e.g., where prostaglandins are involved) or treatment of autoimmune pathologies such as uveitis, type I diabetes, rheumatoid arthritis, inflammatory bowel diseases (e.g., Crohn's disease and ulcerative colitis), multiple sclerosis, lupus, asthma, psoriasis, and in drug-eluting stents. Additional uses can include treatment of brain degenerative diseases, heart diseases, cancers, or hepatitis C. See, for example, WO 2005/085295, WO 2004/010987, WO 03/097028, and WO 2006/072562, each of which is incorporated by reference in its entirety.

"Treatment" of multiple sclerosis includes treating various forms of the disease including relapsing-remitting, chronic progressive, and the S1P receptor agonists can be used alone or in conjunction with other agents to relieve signs and symptoms of the disease as well as prophylactically.

In addition, the disclosed compounds can be used for altering lymphocyte trafficking as a method for prolonging allograft survival, for example solid organ transplants, treatment of graft vs. host disease, bone marrow transplantation, and the like.

In addition, the disclosed compounds can be used to inhibit autotaxin. Autotaxin, a plasma phosphodiesterase, has been demonstrated to undergo end product inhibition. Autotaxin hydrolyzes several substrates to yield lysophosphatidic acid and sphingosine 1-phosphate, and has been implicated in cancer progression and angiogenesis. Therefore, S1P receptor agonist pro-drugs of the disclosed compounds can be used to inhibit autotaxin. This activity may be combined with agonism at S1P receptors or may be independent of such activity.

In addition, disclosed compounds can be useful for inhibition of S1P lyase. S1P lyase is an intracellular enzyme that irreversibly degrades S1P. Inhibition of S1P lyase disrupts lymphocyte trafficking with concomitant lymphopenia. Accordingly, S1P lyase inhibitors can be useful in modulating immune system function. Therefore, the disclosed compounds can be used to inhibit S1P lyase. This inhibition could be in concert with S1P receptor activity, or be independent of activity at any S1P receptor.

In addition, disclosed compounds can be useful as antagonists of the cannabinoid $CB_1$ receptor. $CB_1$ antagonism is associated with a decrease in body weight and an improvement in blood lipid profiles. The $CB_1$ antagonism could be in concert with S1P receptor activity, or be independent of activity at any S1P receptor.

In addition, disclosed compounds can be useful for inhibition of group IVA cytosolic $PLA_2$ ($cPLA_2$). $cPLA_2$ catalyzes the release of eicosanoic acids (e.g., arachidonic acid). The eicosanoic acids are transformed to pro-inflammatory eicosanoids such as prostaglandins and leukotrienes. Thus, disclosed compounds may be useful as anti-inflammatory agents. This inhibition could be in concert with S1P receptor activity, or be independent of activity at any S1P receptor.

In addition, disclosed compounds may be useful for inhibition of the multiple substrate lipid kinase (MuLK). MuLK is highly expressed in many human tumor cells and thus its inhibition might slow the growth or spread of tumors.

Pharmaceutical compositions can include the compounds of formula I. More particularly, such compounds can be formulated as pharmaceutical compositions using standard pharmaceutically acceptable carriers, fillers, solubilizing agents and stabilizers known to those skilled in the art. For example, a pharmaceutical composition including a compound of formula I, or a salt, analog, derivative, or modification thereof, as described herein, is used to administer the appropriate compound to a subject.

The compounds of formula I are useful for treating a disease or disorder including administering to a subject in need thereof of a therapeutically acceptable amount of a compound of formula I, or a pharmaceutical composition comprising a therapeutically effective amount of a compound of formula I, and a pharmaceutically-acceptable carrier.

The disclosed compounds and method are directed to sphingosine 1-phosphate (S1P) analogs that have activity as receptor receptor agonists or antagonists at one or more S1P receptors, specifically the $S1P_1$, $S1P_4$ and $S1P_5$ receptor types. The disclosed compounds and method include both compounds that have a phosphate moiety as well as compounds with hydrolysis-resistant phosphate surrogates such as phosphonates, alpha-substituted phosphonates particularly where the alpha substitution is a halogen and phosphothionates.

The values listed below for radicals, substituents, and ranges, are for illustration only; they do not exclude other defined values or other values within defined ranges for the radicals and substituents.

In cases where compounds of formula I are sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, include but are not limited to, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl)amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are alkyl, substituted alkyl, alkenyl, substituted alkenyl, cycloalkyl, substituted cycloalkyl, cycloalkenyl, substituted cycloalkenyl, aryl, heteroaryl, or heterocyclic and the like. Also included are amines where the two or three substituents, together with the amino nitrogen, form a heterocyclic or heteroaryl group. Non-limiting examples of amines include, isopropylamine, trimethyl amine, diethyl amine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful, for example, carboxylic acid amides, including carboxamides, lower alkyl carboxamides, dialkyl carboxamides, and the like.

The compounds of formula I can be formulated as pharmaceutical compositions and administered to a mammalian host, such as a human patient in a variety of forms adapted to the chosen route of administration, e.g., orally or parenterally, as eyedrops, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically acceptable carrier, which may be a solid or a liquid.

Exemplary solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), each of which is incorporated by reference in its entirety.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

Generally, the concentration of the compound(s) of formula I in a liquid composition, such as a lotion, will be from about 0.1 to about 25 weight percent, preferably from about 0.5-10 weight percent. The concentration in a semi-solid or solid composition such as a gel or a powder will be about 0.1-5 wt-%, preferably about 0.5-2.5 weight percent based on the total weight of the composition.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. In general, however, a dose will be in the range of from about 0.1 to about 10 mg/kg of body weight per day.

The compound is conveniently administered in unit dosage form; for example, containing 0.01 to 10 mg, or 0.05 to 1 mg, of active ingredient per unit dosage form. In some embodiments, a dose of 5 mg/kg or less is suitable.

Ideally, the active ingredient should be administered to achieve peak plasma concentrations of the active compound of from about 1 nm to about 50 µM, preferably, about 10 nM to 5 µM, most preferably, about 10 nM to about 1 µM. This may be achieved, for example, by the intravenous injection of a 0.05 to 5% solution of the active ingredient, optionally in saline, or orally administered as a bolus containing about 0.01 to 10 µg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four, or more sub-doses per day, or more infrequently, such as one to five times a week, or one to five times a month. The sub-dose itself may be further divided, e.g., into a number of discrete loosely spaced administrations; such as multiple inhalations from an insufflator or by application of a plurality of drops into the eye.

The disclosed method includes a kit comprising a compound of formula I and instructional material which describes administering the compound or a composition comprising the compound to a cell or a subject. This should be construed to include other embodiments of kits that are known to those skilled in the art, such as a kit comprising a (preferably sterile) solvent for dissolving or suspending the compound or composition prior to administering the compound or composition to a cell or a subject. Preferably, the subject is a human.

In accordance with the disclosed compounds and methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

The following working examples are provided for the purpose of illustration only, and are not to be construed as limiting in any way the remainder of the disclosure. Therefore, the examples should be construed to encompass any and all variations which become evident as a result of the teaching provided herein.

EXAMPLES

General: Reactions were run under an inert atmosphere. The usual work-up procedure was to add organic solvent, usually ethyl acetate, wash with water or brine, dried, (usually over anhydrous magnesium sulfate) and solvent removed under reduced pressure. If necessary, the mixture was purified by column chromatography.

Example 1:
2-bromo-6-methoxy-3,4-dihydronaphthalen-1(2H)-one

A 10 L flask was fitted with two cooling condensers and a dry pipe. 6.75 L of 1,2-dichloroethane and 750 grams of 6-methoxy-1-tetralone were added and stirred to get a brown transparent liquid. The temperature was raised to 75° C., then 471 g of CuBr₂ was added over a period of 30 min. The mixture was heated to reflux for 2 hrs and a further 337.5 g of CuBr₂ added. After reflux overnight, the color had changed to yellowish-green-gray. HPLC revealed that 10% starting material still remained; a further 100 g of CuBr₂ was added and stirred for 3 hours to complete the reaction.

The reaction was cooled to room temperature, filtered, and the filter cake was washed with 1,2-dichloroethane (750 mL×2), and the mother liquid was washed with NaHCO₃ (1500 mL×4), then washed with brine (750 mL×2). The organic layer was dried with Na₂SO₄ and de-colored with active carbon. The liquid was maintained at a temperature lower than 90° C., concentrated under vacuum, and cooled to 50° C. Methanol was added, the solution decolorized with charcoal, filtered, and washed with 300 mL methanol. The liquids were combined, cooled to 0-5° C. for 30 min, filtered, then washed with 150 mL methanol. The cake was dried to obtain 940 g of 2-bromo-6-methoxy-3,4-dihydronaphthalen-1(2H)-one, M=255.2, purity 98.48%.

Example 2: Diethyl 2-methyl-2-(6-methoxy-1-oxo-1,2,3,4-tetrahydronaphthalen-2-yl)malonate To 6 L of ice cold DMF was added 183 grams of NaH; the mixture stirred and a solution of 811.2 grams diethyl methylmalonate in 1.5 L DMF was added dropwise. The temp was kept at 0-5° C. for 2 hrs, and then cooled below −3° C., and 650 grams bromo-6-methoxy-3,4-dihydronaphthalen-1(2H)-one was added. The reaction was followed by HPLC until the starting material disappeared. The mixture was poured onto ice water, adjusted to pH 4-5 with HCl, and extracted with ethyl acetate. The organic layer was washed with brine, dried, decolorized and concentrated. To the residue was added ether, the mixture cooled, filtered, and the residue washed with petroleum ether to get 745 g of diethyl 2-methyl-2-(6-methoxy-1-oxo-1,2,3,4-tetrahydronaphthalen-2-yl)malonate, M=348.2, purity 96.57%.

Example 3: 2-acetamido-3-ethoxy-2-(6-methoxy-1,2,3,4-tetrahydronaphthalen-2-yl)-3-oxopropanoic acid To 218 g KOH in 2.8 L absolute ethanol was added 560 grams diethyl 2-methyl-2-(6-methoxy-1-oxo-1,2,3,4-tetrahydronaphthalen-2-yl)malonate. The mixture was stirred for 15 hrs. When HPLC showed <2% of starting material remained, the solution was poured into ice water, and the flask was washed with 560 mL cold water. The pH of the solution was adjusted to 2.0-3.0 with 6N HCl. The solution was extracted with dichloromethane three times (1680 mL, 1120 mL, 560 mL), and the organic layers were combined and washed with brine. The temperature was kept <70° C. during concentration. The residue was dissolved in dichloromethane, and REDUCER (700 mL dichloromethane, 1.3 L triethylsilane, 179 mL trifluoroacetic acid, 1 L boron trifluoride etherate, and a further 530 mL dichloromethane) was added dropwise and followed by HPLC until complete. Product was 261 g of 2-methyl-3-ethoxy-2-(6-methoxy-1,2,3,4-tetrahydronaphthalen-2-yl)-3-oxopropanoic acid, M=320.2, purity 94%.

Example 4: ethyl 2-amino-2-(6-methoxy-1,2,3,4-tetrahydronaphthalen-2-yl)propanoate To 225 g of 2-methyl-3-ethoxy-2-(6-methoxy-1,2,3,4-tetrahydronaphthalen-2-yl)-3-oxopropanoic acid in 2.7 L toluene, 315 mL diphenyl phosphoryl azide (DPA) in 207 mL of triethylamine was added. The mixture was heated to reflux (100-110° C.) for 2 hrs, and cooled to 0° C. A fresh trimethylsilonate sodium salt solution (made by adding 240 g NaOH to 487 g hexamethyl disiloxane and 3 L DME, reflux for 20 hrs, filtered, washed with DME 600 mL×2, and concentrated, followed by addition of toluene 2 L×2, and concentrated. The mixture was cooled to 30° C., and 3200 mL THF added and stirred for 30 min to obtain the sodium trimethylsilanolate THF solution) was added dropwise then stirring was stopped and kept overnight. The solution was added to 10% citric acid, pH 3-4, the water layer was extracted with methyl tert-butyl ether three times, organic layers combined, washed with aqueous NaHCO₃, with brine, dried (temperature lower than 90° C.), cooled to room temperature. A mixture of 1.2 L HCl and 3.6 L water was added, stirred for 30 min, washed with methyl tert-butyl ether, adjusted the pH of water layer to 8-9, extracted with methyl tert-butyl ether. The organic layer was dried with Na₂SO₄, decolorized and concentrated to get an oil.

Example 5: 2-amino-2-(6-methoxy-1,2,3,4-tetrahydronaphthalen-2-yl)propan-1-ol To a 2 L flask cooled by ice water was added 60 g LiAlH₄, and 1 L of THF. When the mixture was cooled to below 10° C., a mixture of 118.8 grams of ethyl 2-amino-2-(6-methoxy-1,2,3,4-tetrahydronaphthalen-2-yl)propanoate and 350 mL THF was added dropwise. No starting material remained by HPLC. The temperature was kept below 30° C. while 100 mL ethyl acetate was added. To the concentrated mixture was added 400 mL ethyl acetate, followed by 25 mL ice water. The mixture was filtered, and the filter cake with 300 mL ethyl acetate. The combined organic layers washed with brine 100 mL×2, dried with Na₂SO₄, decolorized with carbon and concentrated. To the oil, was added ether, the mixture stirred for overnight, filtered and dried to afford 50 g of 2-amino-2-(6-methoxy-1,2,3,4-tetrahydronaphthalen-2-yl)propan-1-ol.

Example 6: 4-(6-methoxy-1,2,3,4-tetrahydronaphthalen-2-yl)-4-methyloxazolidin-2-one To 25 grams of 2-amino-2-(6-methoxy-1,2,3,4-tetrahydronaphthalen-2-yl)propan-1-ol in 575 mL of dichloromethane was added 45 g of triethylamine. The mixture was cooled to 0° C., and kept below 5° C. while 21 g of triphosgene in dichloromethane was added dropwise. The mixture was stirred at 20-25° C. for 1.5 hrs. The reaction was followed by HPLC until the starting material disappeared. The mixture was concentrated under reduced pressure, 375 mL ethyl acetate was added to the residue. It was washed with water (50 mL×2), dried, decolorized with carbon, and concentrated and dried to afford 10 g of 4-(6-methoxy-1,2,3,4-tetrahydronaphthalen-2-yl)-4-methyloxazolidin-2-one, M=261, purity 97%.

Example 7: 4-(6-hydroxy-1,2,3,4-tetrahydronaphthalen-2-yl)-4-methyloxazolidin-2-one A stirred solution of 100 grams of 4-(6-methoxy-1,2,3,4-tetrahydronaphthalen-2-yl)-4-methyloxazolidin-2-one in 6 L dichloromethane was cooled to −80° C. under nitrogen. A solution of 177 g BBr₃ in dichloromethane was added dropwise; during addition the reaction temperature was kept below −75° C. The reaction was stirred at 20° C. until the starting material was less than 2% by HPLC. Ice water was added to crystallize the solid, which was filtered, washed with water, and the cake was slurried in methanol and dried to afford 80 g of 4-(6-hydroxy-1,2,3,4-tetrahydronaphthalen-2-yl)-4-methyloxazolidin-2-one, M=247.29, purity>98%.

Example 8: (4S)-4-((2S)-5-Bromo-6-hydroxy-1,2,3, 4-tetrahydronaphthalen-2-yl)-4-methyloxazolidin-2-one Stereoisomers of 4-(6-hydroxy-1,2,3,4-tetrahydronaphthalen-2-yl)-4-methyloxazolidin-2-one (7 g) were separated using superfluid chromatography with two stages. First, using Chiralpak AS-H (2×25 cm) 07-8656 (30% methanol/$CO_2$, 100 bar, 70 mL/min, 220 nm. inj vol.: 1.5 mL, 20 mg/mL 1:1 ethanol:DCM) yielded 1.45 g of diastereomer-1 ($R_f$=5.32 min, chemical purity>99%, de>99%), 1.52 g of diastereomer-2 ($R_f$=6.26 min, chemical purity>99%, de>99%), and the mixture of isomers 3 and 4. Next, isomers 3 and 4 were separated using Chiralpak IC (3×15 cm) 806271 (30% isopropanol/$CO_2$, 100 bar, 75 mL/min, 220 nm., inj vol.: 1.25 mL, 35 mg/mL methanol) yielded 1.28 g of diastereomer-3 ($R_f$=7.97 min, chemical purity>99%, de>99%) and 1.13 g of diastereomer-4 ($R_f$=8.96 min, chemical purity>99%, de>99%). $^1$H NMR showed that isomer 1 and 4 were an enantiomeric pair, and isomer 2 and 3 were another enantiomeric pair.

Figure 2:
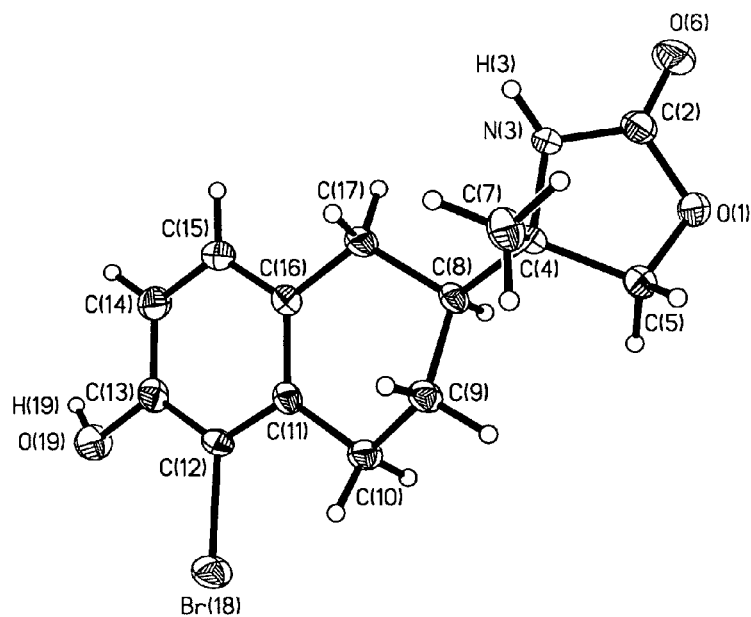
FIG. 2 is an illustration of an X-ray crystal structure of an intermediate useful in the preparation of compounds of Formula (I).

To a mixture of 4-(6-hydroxy-1,2,3,4-tetrahydronaphthalen-2-yl)-4-methyloxazolidin-2-one (100 mg, 0.0004 mol) (pure isomer 2) in N,N-Dimethylformamide (0.5 mL, 0.006 mol) was added N-Bromosuccinimide (72.0 mg, 0.000404 mol) in N,N-Dimethylformamide (0.5 mL, 0.006 mol) and was stirred at for 6 hrs. Water was added, and the mixture was extracted with dichloromethane. The solvent was removed and residue was purified with Isco (12 g silica gel, 0-40% MeOH:DCM) to give a white precipitate (125 mg, 95% yield). $^1$H NMR showed a single isomer. The solid (10.1 mg) was dissolved in MeOH (3 mL) and the solvent allowed to evaporate slowly to give white needles, which was washed with MeOH and collected (5.0 mg). LCMS 1.23 min 328.21 ([M+2], 100%). X-ray shows (S,S) configuration, see FIG. 2.

To obtain the X-ray crystal structure, one of the prisms was cut to 0.03 mm×0.10 mm×0.10 mm in size, mounted on a nylon loop with Paratone-N oil, and transferred to a Bruker SMART APEX II diffractometer equipped with an Oxford Cryosystems 700 Series Cryostream Cooler and Mo Kα radiation (λ=0.71073 Å). A total of 1823 frames were collected at 193 (2) K to $θ_{max}$=27.50° with an ω oscillation range of 0.5°/frame, and an exposure time of 40 s/frame using the APEX2 suite of software. (Bruker AXS, 2006a) Unit cell refinement on all observed reflections, and data reduction with corrections for Lp and decay were performed using SAINT. (Bruker AXS, 2006b) Scaling and a numerical absorption correction were done using SADABS. (Bruker AXS, 2004) The minimum and maximum transmission factors were 0.7429 and 0.9112, respectively. A total of 21361 reflections were collected, 2977 were unique ($R_{int}$=0.0499), and 2708 had I>2σ(I). Systematic absences were consistent with the compound having crystallized in the orthorhombic space group $P2_12_12$, (No. 19). The observed mean $|E^2-1|$ value was 0.687 (versus the expectation values of 0.968 and 0.736 for centric and noncentric data, respectively).

The structure was solved by direct methods and refined by full-matrix least-squares on $F^2$ using SHELXTL. (Bruker AXS, 2001) The asymmetric unit was found to contain one molecule of (4S)-4-((2S)-5-bromo-6-hydroxy-1,2,3,4-tetrahydronaphthalen-2-yl)-4-methyloxazolidin-2-one. All of the nonhydrogen atoms were refined with anisotropic displacement coefficients. The hydrogen atoms were assigned isotropic displacement coefficients U(H)=1.2U(C), 1.5U($C_{methyl}$), 1.5U(N) or 1.5U(O), and their coordinates were allowed to ride on their respective carbons, nitrogen or oxygen. The refinement converged to R(F)=0.0340, wR($F^2$)=0.0908, and S=1.084 for 2708 reflections with I>2σ(I), and R(F)=0.0392, wR($F^2$)=0.0931, and S=1.084 for 2977 unique reflections and 173 parameters. The maximum |Δ/σ| in the final cycle of least-squares was 0.001, and the residual peaks on the final difference-Fourier map ranged from −0.286 to 0.659 eÅ$^{-3}$. Scattering factors were taken from the International Tables for Crystallography, Volume C. (Maslen et al., 1992, and Creagh & McAuley, 1992).

The Flack absolute structure parameter refined to x=−0.001 (12) (versus the expectation values of 0 (within 3 esd's) for the correct and +1 for the inverted absolute structure) indicating that the coordinates were for the correct hand (i.e., (4S)(2S)). (Flack, 1983) For comparison, the incorrect (4R)(2R) enantiomer gave R(F)=0.0628, wR($F^2$)=0.1627, and S=1.034 for 2708 reflections with I>2σ(I), and R(F)=0.0681, wR($F^2$)=0.1664, and S=1.034 for 2977 unique reflections and 173 parameters. The Flack parameter for that incorrect enantiomer was x=1.01 (2).

Example 9: (S)-2-amino-2-((R)-6-(trans-4-tert-butylcyclohexyloxy)-1,2,3,4-tetrahydronaphthalen-2-yl)propan-1-ol The mixture of cis-4-tert-butylcyclohexanol (75.8 mg, 0.000485 mol), (S)-4-((R)-6-hydroxy-1,2,3,4-tetrahydronaphthalen-2-yl)-4-methyloxazolidin-2-one (100 mg, 0.0004 mol) (isomer 1) and triphenylphosphine (127 mg, 0.000485 mol) in tetrahydrofuran (4 mL, 0.05 mol) was heated to reflux, and diisopropyl azodicarboxylate (0.0955 mL, 0.000485 mol) was added dropwise and was stirred and refluxed for overnight. TLC and LCMS monitoring, 2.29 (386.43, M+1, 60%) showed the reaction to be incomplete. The mixture was taken up into DCM and subjected to chromatography purification with EtOAc/hexane (10:90 to 80:20) to give product (109.3 mg, 70% yield).

The mixture of (S)-4-((R)-6-(trans-4-tert-butylcyclohexyloxy)-1,2,3,4-tetrahydronaphthalen-2-yl)-4-methyloxazolidin-2-one (109.3 mg, 0.0002835 mol) (isomer 1) and lithium hydroxide (74.7 mg, 0.00312 mol) in ethanol (1.8 mL, 0.031 mol) and water (0.60 mL, 0.033 mol) was heated to reflux for overnight. LCMS showed starting material was consumed and peak $R_f$=1.66 min 360.39 ([M+1], 100%) left. The solvent was removed under vacuum and the residue was partitioned between water and dichloromethane. The aqueous layer was extensively extracted with dichloromethane. And the combined organic phase was dried over $Na_2SO_4$. The concentrated residue was taken up into dichloromethane and subjected to chromatography purification with dichloromethane/MeOH (10:90 to 80:20) to give the product (17.3 mg, 17% yield). LCMS 360.39 ([M+1], 100%). $^1$H NMR (400 MHz, CD3OD) δ ppm 0.89 (s, 9H), 1.07 (s, 3H), 1.09-1.54 (m, 6H), 1.79-1.87 (m, 3H), 2.04 (m, 1H), 2.15 (m, 2H), 2.53 (dd, J=15.5, 12.3 Hz, 1H), 2.72-2.86 (m, 3H), 3.46 (d, J=11.0 Hz, 1H), 3.55 (d, J=11.0 Hz, 1H), 4.07 (m, 1H), 6.59 (d, J=2.4 Hz, 1H), 6.63 (dd, J=8.3, 2.5 Hz, 1H), 6.94 (d, J=8.3 Hz, 1H).

Example 10: (S)-2-amino-2-((S)-6-(trans-4-tert-butylcyclohexyloxy)-1,2,3,4-tetrahydronaphthalen-2-yl)propan-1-ol The mixture of cis-4-tert-Butylcyclohexanol (75.8 mg, 0.000485 mol), (S)-4-((S)-6-hydroxy-1,2,3,4-tetrahydronaphthalen-2-yl)-4-methyloxazolidin-2-one (100 mg, 0.0004 mol) (isomer2) and triphenylphosphine (127 mg, 0.000485 mol) in tetrahydrofuran (4 mL, 0.05 mol) was heated to reflux, and diisopropyl azodicarboxylate (0.0955 mL, 0.000485 mol) was added dropwise and was stirred and refluxed for overnight. TLC and LCMS monitoring, 2.28 (386.46, M+1, 40%) showed the reaction to be incomplete. The mixture was taken up into dichloromethane and subjected to chromatography purification with EtOAc/hexane (10:90 to 80:20) to give product (46.6 mg, 30% yield).

The mixture of (S)-4-((S)-6-(trans-4-tert-butylcyclohexyloxy)-1,2,3,4-tetrahydronaphthalen-2-yl)-4-methyloxazolidin-2-one (46.6 mg, 0.000121 mol) (isomer2) and lithium hydroxide (31.8 mg, 0.00133 mol) in ethanol (0.77 mL, 0.013 mol) and water (0.26 mL, 0.014 mol) was heated to reflux for overnight. LCMS showed starting material was consumed and peak $R_f$=1.66 min left. The solvent was removed under vacuum and the residue was partitioned between water and dichloromethane. The aqueous was extensively extracted with dichloromethane. And the combined organic phase was dried over $Na_2SO_4$. The concentrated residue was taken up into dichloromethane and subjected to chromatography purification with dichloromethane/MeOH (10:90 to 80:20) to give the product (29.0 mg, 66% yield). LCMS 360.42 ([M+1], 100%). $^1$H NMR (400 MHz, CD3OD) δ ppm 0.89 (s, 9H), 1.06 (s, 3H), 1.04-1.40 (m, 6H), 1.77-1.88 (m, 3H), 1.97 (m, 1H), 2.15 (m, 2H), 2.56 (dd, J=15.8, 12.1 Hz, 1H), 2.71-2.84 (m, 3H), 3.47 (d, J=10.9 Hz, 1H), 3.51 (d, J=10.9 Hz, 1H), 4.07 (m, 1H), 6.58 (d, J=2.5 Hz, 1H), 6.63 (dd, J=8.2, 2.5 Hz, 1H), 6.96 (d, J=8.2 Hz, 1H).

Example 11: (R)-2-amino-2-((R)-6-(trans-4-tert-butylcyclohexyloxy)-1,2,3,4-tetrahydronaphthalen-2-yl)propan-1-ol The mixture of cis-4-tert-butylcyclohexanol (75.8 mg, 0.000485 mol), (R)-4-((R)-6-hydroxy-1,2,3,4-tetrahydronaphthalen-2-yl)-4-methyloxazolidin-2-one (100 mg, 0.0004 mol) (isomer 3) and triphenylphosphine (127 mg, 0.000485 mol) in tetrahydrofuran (4 mL, 0.05 mol) was heated to reflux, and diisopropyl azodicarboxylate (0.0955 mL, 0.000485 mol) was added dropwise and was stirred and refluxed for overnight. TLC and LCMS monitoring, 2.28 (386.29, M+1, 40%) showed the reaction to be incomplete. The mixture was taken up into dichloromethane and subjected to chromatography purification with EtOAc/hexane (10:90 to 80:20) to give product (44.3 mg, 30%).

The mixture of (R)-4-((R)-6-(trans-4-tert-butylcyclohexyloxy)-1,2,3,4-tetrahydronaphthalen-2-yl)-4-methyloxazolidin-2-one (46.6 mg, 0.000121 mol) (from isomer 3) and lithium hydroxide (31.8 mg, 0.00133 mol) in ethanol (0.77 mL, 0.013 mol) and water (0.26 mL, 0.014 mol) was heated to reflux for overnight. LCMS showed SM was consumed and peak $R_f$=1.65 left. The solvent was removed under vacuum and the residue was partitioned between water and dichloromethane. The aqueous was extensively extracted with dichloromethane and the combined organic phase was dried over $Na_2SO_4$. The concentrated residue was taken up into dichloromethane and subjected to chromatography purification with dichloromethane/MeOH (10:90 to 80:20) to give the product (21.2 mg, 49% yield). LCMS 360.42 ([M+1], 100%). $^1$H NMR (400 MHz, CD3OD) δ ppm 0.89 (s, 9H), 1.06 (s, 3H), 1.04-1.40 (m, 6H), 1.77-1.88 (m, 3H), 1.97 (m, 1H), 2.15 (m, 2H), 2.56 (dd, J=15.8, 12.1 Hz, 1H), 2.71-2.84 (m, 3H), 3.47 (d, J=10.9 Hz, 1H), 3.51 (d, J=10.9 Hz, 1H), 4.07 (m, 1H), 6.58 (d, J=2.5 Hz, 1H), 6.63 (dd, J=8.2, 2.5 Hz, 1H), 6.96 (d, J=8.2 Hz, 1H).

Example 12: (R)-2-amino-2-((S)-6-(trans-4-tert-butylcyclohexyloxy)-1,2,3,4-tetrahydronaphthalen-2-yl)propan-1-ol The mixture of cis-4-tert-butylcyclohexanol (75.8 mg, 0.000485 mol), (R)-4-((S)-6-hydroxy-1,2,3,4-tetrahydronaphthalen-2-yl)-4-methyloxazolidin-2-one (100 mg, 0.0004 mol) (isomer 4) and triphenylphosphine (127 mg, 0.000485 mol) in tetrahydrofuran (4 mL, 0.05 mol) was heated to reflux, and diisopropyl azodicarboxylate (0.0955 mL, 0.000485 mol) was added dropwise and was stirred and refluxed for overnight. TLC and LCMS monitoring, 2.28 (386.39, M+1, 50%) showed the reaction to be incomplete. The mixture was taken up into dichloromethane and subjected to chromatography purification with EtOAc/hexane (10:90 to 80:20) to give product (71.7 mg, 40% yield).

The mixture of (R)-4-((S)-6-(trans-4-tert-butylcyclohexyloxy)-1,2,3,4-tetrahydronaphthalen-2-yl)-4-methyloxazolidin-2-one (46.6 mg, 0.000121 mol) (from isomer 4) and lithium hydroxide (31.8 mg, 0.00133 mol) in ethanol (0.77 mL, 0.013 mol) and water (0.26 mL, 0.014 mol) was heated to reflux for overnight. LCMS showed starting material was consumed and peak $R_f$=1.66 min left. The solvent was removed under vacuum and the residue was partitioned between water and dichloromethane. The aqueous layer was extensively extracted with dichloromethane and the combined organic phase was dried over $Na_2SO_4$. The concentrated residue was taken up into dichloromethane and subjected to chromatography purification with dichloromethane/MeOH (10:90 to 80:20) to give the product. (15.7 mg, 36% yield). LCMS 360.43 ([M+1], 100%). $^1$H NMR (400 MHz, CD3OD) δ ppm 0.89 (s, 9H), 1.07 (s, 3H), 1.09-1.54 (m, 6H), 1.79-1.87 (m, 3H), 2.04 (m, 1H), 2.15 (m, 2H), 2.53 (dd, J=15.5, 12.3 Hz, 1H), 2.72-2.86 (m, 3H), 3.46 (d, J=11.0 Hz, 1H), 3.55 (d, J=11.0 Hz, 1H), 4.07 (m, 1H), 6.59 (d, J=2.4 Hz, 1H), 6.63 (dd, J=8.3, 2.5 Hz, 1H), 6.94 (d, J=8.3 Hz, 1H).

Example 13: 2-amino-2-(6-heptyloxyquinolin-3-yl)-1-propanol 3-aminophenol (19 g, 17 mol) was dissolved in $Ac_2O$ (162 g, 1.59 mol, 9.5 eq.), and pyridine (4.9 g, 0.062 mol, 0.36 eq.) was added. Then the reaction mixture was stirred at 80° C. over 2 h. Ice water (50 mL) was added to the mixture, and added saturated $NaHCO_3$ solution to the mixture until pH=7, then extracted (ethyl acetate), washed (brine), dried ($Na_2SO_4$), concentrated to give 3-acetamidophenyl acetate as gray solid (30 g, yield: 93%). ESI-MS: 194 $(M+H)^+$.

A three-neck flask was charged with DMF (25 mL, 0.325 mol, 3 eq.), then $POCl_3$ (70 mL, 0.758 mol, 7 eq.) was added to the DMF at 0° C. The solution was stirred at 0° C. for 30 min. Then 3-acetamidophenyl acetate (20.8 g, 0.108 mol) was added to the mixture at 0° C. After 30 min the mixture heated to 65° C. and stirred for 16 h. Then, the reaction mixture was added ice water (300 mL) and neutralized with saturated $NaHCO_3$ to pH=6, extracted (ethyl acetate), washed (brine), dried ($Na_2SO_4$), filtered and evaporated to dryness to give the crude product, which was purified by silica gel column chromatography (ethyl acetate:pet. ether, 3:1) to give 2-chloro-3-formylquinolin-7-yl acetate as gray solid (2.67 g, yield 10%). ESI-MS: 250 (M+H)$^+$.

To a solution of 2-chloro-3-formylquinolin-7-yl acetate (2.9 g, 14 mmol) and Pd(PPh$_3$)$_4$ (1.6 g, 1.4 mmol, 0.1 eq.), Et$_3$N (17 g, 168 mmol, 16 eq.) in DMF (100 mL) was added formic acid (3.48 g, 75.6 mmol, 5.4 eq.) dropwise over 5 min. The mixture was warmed to 110° C. over 2 h. Then, the reaction mixture was diluted (water), extracted (ethyl acetate), washed (brine), dried (Na$_2$SO$_4$), filtered and evaporated to dryness to give the crude product, which was purified by silica gel column chromatography (pet. ether: ethyl acetate, 1:1) to give 7-hydroxyquinoline-3-carbaldehyde as yellow solid (1.45 g, yield 60%). ESI-MS: 216 (M+H)$^+$.

To a solution of 7-hydroxyquinoline-3-carbaldehyde (1.3 g, 7.5 mmol) in DMF (30 mL) was added 1-bromo-heptane (5.37 g, 30 mmol, 4 eq.) and K$_2$CO$_3$ (2.0 g, 15 mmol, 2 eq.). The mixture was warmed to 60° C. over 3 h. Then, the reaction mixture was diluted (water), extracted (ethyl acetate), washed (brine), dried (Na$_2$SO$_4$), filtered and evaporated to dryness to give the crude product, which was purified by silica gel column chromatography (pet. ether: ethyl acetate, 10:1) to give 7-(heptyloxy)quinoline-3-carbaldehyde as yellow solid (610 mg, yield 30%). ESI-MS: 272 (M+H)$^+$.

To a solution of 7-(heptyloxy)quinoline-3-carbaldehyde (1.6 g, 5.9 mmol) in THF (30 mL) at 0° C. was added CH$_3$MgI (2 g, 12 mmol, 2 eq.) dropwise over 10 min. The mixture was warmed to it over 8 h. Then, the reaction mixture was quenched (water), extracted (ethyl acetate), washed (brine), dried (Na$_2$SO$_4$), filtered and evaporated to dryness to give the crude product, which was purified by silica gel column chromatography (pet. ether:ethyl acetate, 1:5) to give 1-(7-(heptyloxy)quinolin-3-yl)ethanol as yellow oil (1.35 g, yield 80%). ESI-MS: 288 (M+H)$^+$.

To a solution of oxalyl chloride (987 mg, 7.8 mmol, 1.5 eq.) in dry CH$_2$Cl$_2$ (40 mL) was added slowly DMSO (1.6 g, 20.8 mmol, 4 eq.) at −78° C. under N$_2$ After 30 min, 1-(7-(heptyloxy)quinolin-3-yl)ethanol (1.5 g, 5.2 mmol) was added dropwise at −78° C. The mixture was stirred for 2 h at −78° C., and then Et$_3$N (3.2 g, 31 mmol, 6 eq.) was added at −78° C. After 20 min, the mixture was warmed to room temperature. Then the reaction mixture was added water (30 mL), extracted (DCM), washed (brine), dried (Na$_2$SO$_4$), filtered and evaporated to dryness to give the crude product, which was purified by silica gel column chromatography (PE-EA, 10:1) to give 1-(7-(heptyloxy) quinolin-3-yl)ethanone as yellow solid (1.08 g, yield 73%). ESI-MS: 286 (M+H)$^+$.

A mixture of 1-(7-(heptyloxy)quinolin-3-yl)ethanone (730 mg, 2.56 mmol), EtOH (2 mL), H$_2$O (3 mL), (NH$_4$)$_2$CO$_3$ (1.47 g, 15.36 mmol, 6 eq.), and NaCN (251 mg, 5.12 mmol, 2 eq.) was stirred for 16 h at 60° C. Then, the reaction mixture was added water (20 mL), extracted (EA), washed (brine), dried (Na$_2$SO$_4$), filtered and evaporated to dryness to give the crude product, which was purified by silica gel column chromatography (PE-EA, 1:2) to give 5-(7-(heptyloxy)quinolin-3-yl)-5-methylimidazolidine-2,4-dione as yellow solid (480 mg, yield 53%). ESI-MS: 356 (M+H)$^+$.

A mixture of 5-(7-(heptyloxy)quinolin-3-yl)-5-methylimidazolidine-2,4-dione (1 g, 2.8 mmol), EtOH (2 mL), H$_2$O (4 mL), and NaOH (2.24 g, 56 mmol, 20 eq.) was stirred for 4 day at 110° C. Then, the reaction mixture was added HCl (40%) to adjust its pH=5 and then 2-amino-2-(7-(heptyloxy) quinolin-3-yl)propanoic acid was generated as yellow solid (740 mg, yield 80%), without further purification for next step. ESI-MS: 331 (M+H)$^+$.

To a solution of crude 2-amino-2-(7-(heptyloxy)quinolin-3-yl)propanoic acid (600 mg, 1.8 mmol) in dry THF (30 mL) was added LAH (138 mg, 3.6 mmol, 2 eq.) at 0° C. under N$_2$. Then, the mixture was warmed to room temperature for 3 h. Then the reaction mixture was added water (1 mL), diluted (EA), filtered and dried (Na$_2$SO$_4$), evaporated to dryness to give the crude product, which was purified by prep-HPLC to give 2-amino-2-(7-(heptyloxy)quinolin-3-yl) propan-1-ol as white solid (200 mg, yield 35%). ESI-MS: 317 (M+H)+.

Example 14:
6-(trans-4-tert-Butyl-cyclohexyloxy)-quinoline

Quinolin-6-ol (7.52 g, 0.0518 mol, Aldrich), 4-tert-butyl-cyclohexanol (9.71 g, 0.0621 mol) and triphenylphosphine (16.32 g, 0.06222 mol, Aldrich) were placed in a flask, and dissolved in tetrahydrofuran (150 mL, Acros). The reaction was cooled in a cold water bath. Diisopropyl azodicarboxylate (13.0 mL, 0.0620 mol, Acros) in tetrahydrofuran (50 mL, Acros) was then added dropwise. The reaction mixture was then allowed to stir at room temperature. After 26 h, the solvent was removed, and the residue was taken up in DCM. Silica gel was added and the solvent was removed. The residue was then purified via silica gel chromatography using 0-40% ethyl acetate in hexanes as eluent to give the product (Rf=0.22 in 3:1 hexanes/ethyl acetate), 6.11 g yield (42%).

Example 15:
6-(trans-4-tert-butyl-cyclohexyloxy)-quinoline 1-oxide 6-(trans-4-tert-Butyl-cyclohexyloxy)-quinoline (6.11 g, 0.0216 mol) was dissolved in acetone (100 mL, Acros), followed by m-chloroperbenzoic acid (11.7 g, 0.0542 mol, Aldrich) in small portions at RT. The reaction mixture was then stirred at 23° C. for 1.5 hours. Sodium thiosulfate was added, 97.6 mL of a saturated aqueous solution. The reaction mixture was then allowed to stir for 45 minutes. Excess of solvents were removed under vacuum, and the residue was diluted with water and extracted with methylene chloride. Combined organic layers were treated with magnesium sulfate, filtered and evaporated. The residue was taken up in methylene chloride and silica gel was added. The solvents were removed. The residue was then purified via chromatography (SiO$_2$, 0-10% MeOH/DCM) to give the product (Rf=0.19 in 5% methanol/methylene chloride). The appropriate fractions were combined to give the product in 4.99 g yield (77%).

Example 16: 2-[6-(trans-4-tert-butyl-cyclohexyloxy)-quinolin-2-yl]-2-nitro-propionic acid ethyl ester A solution of ethyl 2-nitropropionate (5.94 g, 0.0404 mol, Aldrich) in N,N-dimethylformamide (40 mL, Acros) was added to 6-(trans-4-tert-butyl-cyclohexyloxy)-quinoline 1-oxide (10.08 g, 0.03367 mol) and acetic anhydride (4.765 mL, 0.05050 mol, Aldrich) in N,N-dimethylformamide (80 mL, Aldrich) dropwise. The reaction mixture was then stirred at RT for 3 d. The reaction was partitioned between Na$_2$CO$_3$ (sat), and DCM. Organic layer was collected, and dried over MgSO$_4$. The drying agent was filtered and the solvent was removed by evaporation. The mixture was then purified via chromatography (SiO$_2$, 0-5% methanol in methylene chloride as eluent) to give the product (solvent front in 5% methanol/methylene chloride, Rf=0.72 in 3:1 hexanes/ethyl acetate). Appropriate fractions were combined and evaporated to give 7.37 g of the product as a white solid (51%).

Example 17: 2-Amino-2-[6-(trans-4-tert-butyl-cyclohexyloxy)-quinolin-2-yl]-propionic acid ethyl ester 2-[6-(trans-4-tert-Butyl-cyclohexyloxy)-quinolin-2-yl]-2-nitro-propionic acid ethyl ester (76 mg, 0.00018 mol) was dissolved in acetic acid (1.0 mL, Fisher), and cooled in a 20° C. water bath, followed by addition of zinc (115 mg, 0.00176 mol, Aldrich) in small portions. After 2 h, the reaction was diluted with acetic acid and acetonitrile and filtered through a PTFE filter. The excess of solvents were removed under vacuum, and the residue was purified via preparative HPLC (10-90% acetonitrile with 0.1% TFA) to give a pure product (18 mg, 20%) as TFA salt.

Example 18: 2-Amino-2-[6-(trans-4-tert-butyl-cyclohexyloxy)-quinolin-2-yl]-propan-1-ol 2-Amino-2-[6-(trans-4-tert-butyl-cyclohexyloxy)-quinolin-2-yl]-propionic acid ethyl ester (18 mg as TFA salt, 0.000035 mol) was dissolved in a mixture of methanol (2.0 mL, Acros) and tetrahydrofuran (2.0 mL, Acros), then sodium tetrahydroborate (3.8 mg, 0.00010 mol, Aldrich) was added. After 2 h, additional sodium tetrahydroborate (8.1 mg, 0.00021 mol, Aldrich) was added. After an additional 2 h, the reaction mixture was quenched with 250 uL of saturated NH$_4$Cl, and solvents were removed under vacuum. DMSO (½ mL) was added to the residue but it did not completely solubilize. The material was partitioned between methylene chloride and water. The emulsion was broken up by adding saturated sodium chloride and solid sodium chloride. The organics were dried with magnesium sulfate, filtered and evaporated. The residue was purified via preparative HPLC to give pure product (6.3 mg, 38%) as TFA salt. MS: m/z=357.20 [M+H]+. $^1$H NMR (400 MHz, CHLOROFORM-d) δ ppm: 8.19 (d, J=8.5 Hz, 1H), 7.96 (d, J=9.3 Hz, 1H), 7.39-7.46 (m, 2H), 7.13 (d, J=2.8 Hz, 1H), 4.24-4.36 (m, 1H), 4.12-4.21 (m, 2H), 2.23-2.32 (m, 2H), 1.88-1.96 (m, 2H), 1.78 (s, 3H), 1.41-1.54 (m, 2H), 1.10-1.27 (m, 3H), 0.91 (s, 9H).

Example 19: 2-[6-(trans-4-tert-Butyl-cyclohexyloxy)-5-iodo-quinolin-2-yl]-2-nitro-propionic acid ethyl ester N-Iodosuccinimide (3446 mg, 0.01532 mol, Aldrich) and zirconium tetrachloride (481 mg, 0.00206 mol, Aldrich) were added to a solution of 2-[6-(trans-4-tert-Butyl-cyclohexyloxy)-quinolin-2-yl]-2-nitro-propionic acid ethyl ester (4.37 g, 0.0102 mol) in methylene chloride (150 mL, Acros) and was stirred at room temperature for 1 h. The reaction was filtered through Celite, washed, then filtered through a paper filter. The solution was held at room temperature for 2 h. The solvent was then evaporated to approximately 100 mL and then silica gel was added. The solvent was removed under reduced pressure, and the residue was purified by silica gel chromatography using 0-25% ethyl acetate in hexanes as eluent to give the product (Rf=0.33 in 7:1 hexanes/ethyl acetate) in 5.28 g yield (93%). Note that the product contains 6% of an unidentified material (possibly the analogous chloride).

Example 19A: 2-[6-(trans-4-tert-butyl-cyclohexyloxy)-5-trifluoromethyl-quinolin-2-yl]-2-nitro-propionic acid ethyl ester A solution of 2-[6-(trans-4-tert-Butyl-cyclohexyloxy)-5-iodo-quinolin-2-yl]-2-nitro-propionic acid ethyl ester (5.28 g, 9.52 mmol), hexamethylphosphoramide (8.37 mL, 47.6 mmol, Fluka) in N,N-dimethylformamide (55 mL, Aldrich) was degassed by stirring vigorously while forcing argon through the apparatus (5 min). To this was added copper(I) iodide (3.26 g, 17.1 mmol, Aldrich) and methyl fluorosulphonyldifluoroacetate (6.24 mL, 47.6 mmol, Aldrich) and the reaction was stirred in a sealed vessel at 80° C. under an atmosphere of argon. After stirring for 17 hours, the reaction was evaporated, then diluted with methylene chloride. Silica gel was added and the solvent removed under reduced pressure. The material was purified by silica gel chromatography using 0-35% ethyl acetate in hexanes as eluent (Rf=0.25 in 7:1 ethyl acetate/hexanes) to give the product in 4.71 g (100%) yield. The impurity seen in 2-[6-(trans-4-tert-Butyl-cyclohexyloxy)-5-iodo-quinolin-2-yl]-2-nitro-propionic acid ethyl ester is still present, in less than 5%.

Example 20: 2-Amino-2-[6-(trans-4-tert-butyl-cyclohexyloxy)-5-trifluoromethyl-quinolin-2-yl]-propionic acid ethyl ester 2-Amino-2-[6-(trans-4-tert-butyl-cyclohexyloxy)-5-trifluoromethyl-quinolin-2-yl]-propionic acid ethyl ester was synthesized as per 2-amino-2-[6-(trans-4-tert-butyl-cyclohexyloxy)-quinolin-2-yl]-propionic acid ethyl ester (Example 17) in 20% yield (TFA salt) using 2-[6-(trans-4-tert-Butyl-cyclohexyloxy)-5-trifluoromethyl-quinolin-2-yl]-2-nitro-propionic acid ethyl ester as starting material.

Example 21: 2-Amino-2-[6-(trans-4-tert-butyl-cyclohexyloxy)-5-trifluoromethyl-quinolin-2-yl]-propan-1-ol 2-Amino-2-[6-(trans-4-tert-butyl-cyclohexyloxy)-5-trifluoromethyl-quinolin-2-yl]-propan-1-ol was synthesized as per 2-amino-2-[6-(trans-4-tert-butyl-cyclohexyloxy)-quinolin-2-yl]-propan-1-ol (Example 18) in 49% yield (TFA salt) using 2-amino-2-[6-(trans-4-tert-butyl-cyclohexyloxy)-5-trifluoromethyl-quinolin-2-yl]-propionic acid ethyl ester as starting material (TFA salt). MS: m/z=425.20 [M+H]+. $^1$H NMR (400 MHz, CHLOROFORM-d) δ ppm: 8.70 (d, J=8.8 Hz, 1H), 8.15 (d, J=9.5 Hz, 1H), 7.62 (d, J=9.5 Hz, 1H), 7.50 (d, J=9.3 Hz, 1H), 4.33-4.45 (m, 1H), 4.08-4.25 (m, 2H), 2.15-2.27 (m, 2H), 1.85-1.98 (m, 2H), 1.78 (s, 3H), 1.48-1.64 (m, 2H), 1.04-1.24 (m, 3H), 0.90 (s, 9H).

Example 22: 2-Amino-2-[6-(trans-4-tert-butyl-cyclohexyloxy)-quinolin-2-yl]-propionic acid ethyl ester Enantiomer 1 and

2-Amino-2-[6-(trans-4-tert-butyl-cyclohexyloxy)-quinolin-2-yl]-propionic acid ethyl ester Enantiomer 2

2-Amino-2-[6-(trans-4-tert-butyl-cyclohexyloxy)-quinolin-2-yl]-propionic acid ethyl ester (racemic mixture, 522 mg) was separated by chiral chromatography (ChiralPak IC (3×15 cm) 35% EtOH (0.1% DEA)/$CO_2$ 100 bar 75 mL/min 220 nm inj vol 0.5 mL 26 mg/mL methanol). Isolated were 220 mg (42%) of enantiomer 1 (RT=1.65 min on Chiralpak IC 15×0.46 cm, 40% ethanol(DEA)/CO2, 100 bar, 3 ml/min, 220 nm) and 226 mg (43%) of enantiomer 2 (RT=2.25 min, same conditions).

Example 23: 2-Amino-2-[6-(trans-4-tert-butyl-cyclohexyloxy)-quinolin-2-yl]-propan-1-ol Enantiomer 1

2-Amino-2-[6-(trans-4-tert-butyl-cyclohexyloxy)-quinolin-2-yl]-propan-1-ol Enantiomer 1 was synthesized as per 2-Amino-2-[6-(trans-4-tert-butyl-cyclohexyloxy)-quinolin-2-yl]-propan-1-ol (Example 18) in 31% yield as bis-TFA salt, using 2-amino-2-[6-(trans-4-tert-butyl-cyclohexyloxy)-quinolin-2-yl]-propionic acid ethyl ester Enantiomer 1 as starting material. MS: m/z=357.30 [M+H]+. $^1$H NMR (400 MHz, CHLOROFORM-d) δ ppm: 8.18 (d, J=8.5 Hz, 1H), 7.96 (d, J=9.0 Hz, 1H), 7.38-7.47 (m, 2H), 7.13 (d, J=2.8 Hz, 1H), 4.25-4.35 (m, 1H), 4.11-4.23 (m, 2H), 2.24-2.32 (m, 2H), 1.88-1.97 (m, 2H), 1.83 (s, 3H), 1.41-1.54 (m, 2H), 1.10-1.31 (m, 3H), 0.91 (s, 9H).

Example 24: 2-Amino-2-[6-(trans-4-tert-butyl-cyclohexyloxy)-quinolin-2-yl]-propan-1-ol Enantiomer 2

2-Amino-2-[6-(trans-4-tert-butyl-cyclohexyloxy)-quinolin-2-yl]-propan-1-ol Enantiomer 2 was synthesized as per 2-amino-2-[6-(trans-4-tert-butyl-cyclohexyloxy)-quinolin-2-yl]-propan-1-ol (Example 18) in 19% yield as bis-TFA salt, using 2-amino-2-[6-(trans-4-tert-butyl-cyclohexyloxy)-quinolin-2-yl]-propionic acid ethyl ester Enantiomer 2 as starting material. MS: m/z=357.20 [M+H]+. $^1$H NMR (400 MHz, CHLOROFORM-d) δ ppm: 8.19 (d, J=8.5 Hz, 1H), 7.96 (d, J=9.3 Hz, 1H), 7.38-7.48 (m, 2H), 7.13 (d, J=2.8 Hz, 1H), 4.25-4.35 (m, 1H), 4.10-4.23 (m, 2H), 2.23-2.32 (m, 2H), 1.88-1.98 (m, 2H), 1.82 (s, 3H), 1.41-1.54 (m, 2H), 1.10-1.28 (m, 3H), 0.91 (s, 9H).

Example 25: 2-Amino-2-[6-(trans-4-tert-butyl-cyclohexyloxy)-5-trifluoromethyl-quinolin-2-yl]-propionic acid ethyl ester Enantiomer 1 and

2-Amino-2-[6-(trans-4-tert-butyl-cyclohexyloxy)-5-trifluoromethyl-quinolin-2-yl]-propionic acid ethyl ester Enantiomer 2

Racemic 2-Amino-2-[6-(trans-4-tert-butyl-cyclohexyloxy)-5-trifluoromethyl-quinolin-2-yl]-propionic acid ethyl ester (755 mg) was separated into two enantiomers by Chiralpak IC (3×15 cm); 20% methanol (0.1% DEA)/$CO_2$, 100 bar; 75 ml/min, 220 nm; inj vol. 0.3 mL, 38 mg/mL methanol. Isolated were: Enantiomer 1: 323 mg (43%), >99%, >99% ee RT=1.22 min on Chiralpak IC (15×0.46 cm); 40% methanol (DEA)/$CO_2$, 100 bar; 3 ml/min, 220 nm Enantiomer 2: 322 mg (43%), >99%, >98% ee RT=1.34 min on Chiralpak IC (15×0.46 cm); 40% methanol (DEA)/$CO_2$, 100 bar; 3 mL/min, 220 nm

Example 26: 2-Amino-2-[6-(trans-4-tert-butyl-cyclohexyloxy)-5-trifluoromethyl-quinolin-2-yl]-propan-1-ol Enantiomer 1

2-Amino-2-[6-(trans-4-tert-butyl-cyclohexyloxy)-5-trifluoromethyl-quinolin-2-yl]-propan-1-ol Enantiomer 1 was synthesized as per 2-amino-2-[6-(trans-4-tert-butyl-cyclohexyloxy)-quinolin-2-yl]-propan-1-ol (Example 18) in 52% yield as bis-TFA salt using 2-amino-2-[6-(trans-4-tert-butyl-cyclohexyloxy)-5-trifluoromethyl-quinolin-2-yl]-propionic acid ethyl ester Enantiomer 1 as starting material. MS: m/z=425.30 [M+H]+. $^1$H NMR (400 MHz, CHLOROFORM-d) δ ppm: 8.68 (d, J=8.8 Hz, 1H), 8.12 (d, J=9.0 Hz, 1H), 7.47-7.60 (m, 2H), 4.31-4.44 (m, 1H), 4.09-4.26 (m, 2H), 2.13-2.25 (m, 2H), 1.85-1.95 (m, 2H), 1.81 (s, 3H), 1.48-1.62 (m, 2H), 1.03-1.22 (m, 3H), 0.90 (s, 9H).

Example 27: 2-Amino-2-[6-(trans-4-tert-butyl-cyclohexyloxy)-5-trifluoromethyl-quinolin-2-yl]-propan-1-ol Enantiomer 2

2-Amino-2-[6-(trans-4-tert-butyl-cyclohexyloxy)-5-trifluoromethyl-quinolin-2-yl]-propan-1-ol Enantiomer 2 was synthesized as per 2-amino-2-[6-(trans-4-tert-butyl-cyclohexyloxy)-quinolin-2-yl]-propan-1-ol (Example 17) in 55% yield as bis-TFA salt using 2-amino-2-[6-(trans-4-tert-butyl-cyclohexyloxy)-5-trifluoromethyl-quinolin-2-yl]-propionic acid ethyl ester Enantiomer 2 as starting material. MS: m/z=425.30 [M+H]+. $^1$H NMR (400 MHz, CHLOROFORM-d) δ ppm: 8.68 (d, J=8.5 Hz, 1H), 8.13 (d, J=9.5 Hz, 1H), 7.56 (d, J=9.8 Hz, 1H), 7.51 (d, J=9.0 Hz, 1H), 4.30-4.44 (m, 1H), 4.06-4.24 (m, 2H), 2.12-2.26 (m, 2H), 1.85-1.95 (m, 2H), 1.80 (s, 3H), 1.48-1.62 (m, 2H), 1.03-1.22 (m, 3H), 0.90 (s, 9H).

Example 28: {1-[6-(trans-4-tert-butyl-cyclohexyloxy)-quinolin-2-yl]-2-hydroxy-1-methyl-ethyl}-carbamic acid tert-butyl ester Enantiomer 1

2-Amino-2-[6-(trans-4-tert-butyl-cyclohexyloxy)-quinolin-2-yl]-propan-1-ol Enantiomer 1 (0.1055 g, 0.0001805 mol as bis-TFA salt) was dissolved in chloroform (2.0 mL, Aldrich) along with di-tert-Butyldicarbonate (89 mg, 0.00041 mol, Aldrich). Saturated aqueous sodium bicarbonate solution (1.0 mL, 0.010 mol) was added and the reaction was stirred vigorously for 16 h. The reaction was diluted with methylene chloride and the aqueous layer removed. Drying with $MgSO_4$, filtering, evaporation of solvent and purification by silica gel chromatography using 0-50% ethyl acetate in hexanes as eluent to give the product (Rf=0.20 in 3:1 hexanes/ethyl acetate) in 81 mg yield (98%).

Example 29: [1-[6-(4-trans-tert-butyl-cyclohexyloxy)-quinolin-2-yl]-2-(di-tert-butoxy-phosphoryloxy)-1-methyl-ethyl]-carbamic acid tert-butyl ester Enantiomer 1

To a solution of {1-[6-(trans-4-tert-Butyl-cyclohexyloxy)-quinolin-2-yl]-2-hydroxy-1-methyl-ethyl}-carbamic acid tert-butyl ester Enantiomer 1 (81.0 mg, 0.000177 mol) and 1H-tetrazole (0.124 g, 0.00177 mol, Waterstone) in tetrahydrofuran (1.2 mL, Acros) was added di-tert-butyl N,N-diethylphosphoramidite (247 uL, 0.000887 mol, Aldrich) at rt. After 2 h, the phosphite was oxidized with hydrogen peroxide (118 uL, 0.00115 mol, Aldrich) and stirred for 1 hour. The reaction was then quenched with 10% $NaS_2O_3$ in saturated sodium bicarbonate, extracted with EtOAc, washed with saturated sodium chloride and then dried with $Na_2SO_4$. The drying agent was filtered and the organic layer was concentrated in vacuo, yielding the crude product. The crude was taken up in DCM and purified using silica gel chromatography using 0-100% ethyl acetate in hexanes as eluent. Isolated was the product (Rf=0.47 in 1:1 hexanes/ethyl acetate) in 86 mg yield (75%).

Example 30: Phosphoric acid mono-{2-amino-2-[6-(4-tert-butyl-cyclohexyloxy)-quinolin-2-yl]-propyl}ester Enantiomer 1

To [1-[6-(trans-4-tert-Butyl-cyclohexyloxy)-quinolin-2-yl]-2-(di-tert-butoxy-phosphoryloxy)-1-methyl-ethyl]-carbamic acid tert-butyl ester Enantiomer 1 (86 mg, 0.00013 mol) was added 12 M hydrogen chloride in water (1.0 mL, Fisher) and acetic acid (5.0 mL, Fisher) and the solution was stirred for 1.5 h at RT. Removal of solvent gave an oil, which was purified by preparative HPLC to give the product in 14 mg yield as bis-TFA salt (16%). MS: m/z=437.62 [M+H]+. $^1$H NMR (400 MHz, METHANOL-$d_4$) δ ppm: 8.30 (d, J=8.5 Hz, 1H), 8.00 (d, J=9.3 Hz, 1H), 7.63 (d, J=8.3 Hz, 1H), 7.40 (dd, J=9.2, 2.6 Hz, 1H), 7.33 (d, J=2.5 Hz, 1H), 4.35-4.45 (m, 1H), 4.27-4.35 (m, 1H), 3.95-4.01 (m, 1H), 2.24-2.34 (m, 2H), 1.89-1.98 (m, 2H), 1.79 (s, 3H), 1.38-1.53 (m, 2H), 1.22-1.37 (m, 2H), 1.08-1.20 (m, J=13.6 Hz, 1H), 0.94 (s, 9H).

Example 31: {1-[6-(trans-4-tert-Butyl-cyclohexyloxy)-5-trifluoromethyl-quinolin-2-yl]-2-hydroxy-1-methyl-ethyl}-carbamic acid tert-butyl ester Enantiomer 1

{1-[6-(trans-4-tert-Butyl-cyclohexyloxy)-5-trifluoromethyl-quinolin-2-yl]-2-hydroxy-1-methyl-ethyl}-carbamic acid tert-butyl ester Enantiomer 1 was synthesized as per {1-[6-(trans-4-tert-Butyl-cyclohexyloxy)-quinolin-2-yl]-2-hydroxy-1-methyl-ethyl}-carbamic acid tert-butyl ester Enantiomer 1 (Example 28) in 95% yield using 2-amino-2-[6-(trans-4-tert-butyl-cyclohexyloxy)-5-trifluoromethyl-quinolin-2-yl]-propan-1-ol Enantiomer 1 as starting material (bis-TFA salt).

Example 32: [1-[6-(trans-4-tert-Butyl-cyclohexyloxy)-5-trifluoromethyl-quinolin-2-yl]-2-(di-tert-butoxy-phosphoryloxy)-1-methyl-ethyl]-carbamic acid tert-butyl ester Enantiomer 1

[1-[6-(trans-4-tert-Butyl-cyclohexyloxy)-5-trifluoromethyl-quinolin-2-yl]-2-(di-tert-butoxy-phosphoryloxy)-1-methyl-ethyl]-carbamic acid tert-butyl ester Enantiomer 1 was synthesized as per [1-[6-(trans-4-tert-Butyl-cyclohexyloxy)-quinolin-2-yl]-2-(di-tert-butoxy-phosphoryloxy)-1-methyl-ethyl]-carbamic acid tert-butyl ester Enantiomer 1 (Example 29) in 68% yield using {1-[6-(trans-4-tert-Butyl-cyclohexyloxy)-5-trifluoromethyl-quinolin-2-yl]-2-hydroxy-1-methyl-ethyl}-carbamic acid tert-butyl ester Enantiomer 1 as starting material.

Example 33: Phosphoric acid mono-{2-amino-2-[6-(trans-4-tert-butyl-cyclohexyloxy)-5-trifluoromethyl-quinolin-2-yl]-propyl}ester Enantiomer 1

Phosphoric acid mono-{2-amino-2-[6-(trans-4-tert-butyl-cyclohexyloxy)-5-trifluoromethyl-quinolin-2-yl]-propyl}ester Enantiomer 1 was synthesized as per Phosphoric acid mono-{2-amino-2-[6-(trans-4-tert-butyl-cyclohexyloxy)-quinolin-2-yl]-propyl}ester Enantiomer 1 (Example 30) in 88% yield as bis-HCl salt using [1-[6-(trans-4-tert-Butyl-cyclohexyloxy)-5-trifluoromethyl-quinolin-2-yl]-2-(di-tert-butoxy-phosphoryloxy)-1-methyl-ethyl]-carbamic acid tert-butyl ester Enantiomer 1 as starting material. (Note that HPLC purification was not necessary and compound was isolated as bis-HCl salt). MS: m/z=505.20 [M+H]+. $^1$H NMR (400 MHz, METHANOL-$d_4$) δ ppm: 8.67 (d, J=8.5 Hz, 1H), 8.31 (d, J=9.5 Hz, 1H), 7.85 (d, J=9.3 Hz, 1H), 7.79 (d, J=9.3 Hz, 1H), 4.50-4.62 (m, 1H), 4.34-4.42 (m, 1H), 4.26-4.34 (m, 1H), 2.17-2.29 (m, 2H), 1.88-1.98 (m, 2H), 1.80 (s, 3H), 1.45-1.59 (m, 2H), 1.20-1.34 (m, 2H), 1.07-1.19 (m, 1H), 0.93 (s, 9H).

Example 34: 6-Heptyloxyquinoline

Quinolin-6-ol (1, 2.00 g, 0.0138 mol), 1-heptanol (1.60 g, 0.0138 mol) and triphenylphosphine (4.34 g, 0.0165 mol) were placed in a flask, and dissolved in tetrahydrofuran (200 mL, 2 mol) at 23° C. A solution of diisopropyl azodicarboxylate (3.46 mL, 0.0165 mol) in THF (5 mL) was then added dropwise. The reaction mixture was then allowed to stir at 23° C. for 15 hours. Solvent was removed, and the residue was then purified via chromatography (SiO$_2$, 120 g, 5% MeOH in DCM) to give 2.95 g product (88%). $^1$H NMR (CHLOROFORM-d) δ: 8.76 (dd, J=4.0, 1.5 Hz, 1H), 8.02 (dd, J=15.9, 8.7 Hz, 2H), 7.31-7.44 (m, 2H), 7.07 (d, J=2.8 Hz, 1H), 4.09 (t, J=6.5 Hz, 2H), 1.79-1.96 (m, 2H), 1.45-1.60 (m, 4H), 1.14-1.45 (m, 4H), 0.82-0.99 (m, 3H). MS (M+1): 244.20.

Example 35: 6-Heptyloxyquinoline 1-oxide

6-Heptyloxyquinoline (1000.0 mg, 0.0041094 mol) was dissolved in acetone (20 mL, 0.3 mol), followed by m-chloroperbenzoic acid (1060 mg, 0.00493 mol) in small portions at 23° C. The reaction mixture was then stirred at 23° C. for 3 hours, and LC/MS indicated all the SM was converted to the desired product. A solution of sodium thiosulfate (1950 mg, 0.0123 mol) was added. The reaction mixture was then allowed to stir for 1 hour. Excess of solvents were removed under vacuum, and the residue was treated with DCM (100×3 mL). Combined organic layers were treated with sodium sulfate and filtrated. The crude mixture was then purified via chromatography (SiO$_2$, 120 g, 0-8% MeOH/DCM) to give 653 mg (53%) pure product. $^1$H NMR (CHLOROFORM-d) δ: 8.65 (d, J=9.5 Hz, 1H), 8.38 (d, J=5.8 Hz, 1H), 7.60 (d, J=8.5 Hz, 1H), 7.38 (dd, J=9.5, 2.5 Hz, 1H), 7.23 (dd, J=8.3, 6.0 Hz, 1H), 7.09 (d, J=2.5 Hz, 1H), 4.08 (t, J=6.5 Hz, 2H), 1.80-1.92 (m, 2H), 1.44-1.57 (m, 2H), 1.28-1.44 (m, 6H), 0.90 (t, J=6.8 Hz, 3H). MS (M+1): 260.20.

Example 36: Ethyl 2-(6-heptyloxyquinolin-2-yl)-2-nitropropanoate

A solution of 6-Heptyloxy-quinoline 1-oxide (500 mg, 0.002 mol) and acetic anhydride (0.255 mL, 0.00270 mol) in N,N-dimethylformamide (5 mL, 0.06 mol) was added to a solution of ethyl 2-nitropropionate (284 mg, 0.00193 mol) in DMF (2 mL) at at 23° C. dropwise. The reaction mixture was then stirred at 23° C. for 12 hours. The reaction mixture was then heated at 50° C. for 6 hours. Solvent was removed under vacuum, and the residue was treated with Na$_2$CO$_3$ (sat), and DCM. Organic layer was collected, and dried over Na$_2$SO$_4$. The mixture was then purified via chromatography (SiO$_2$, 24 g, ethyl acetate/hexanes 0-35%) to give a pure product 523 mg (70%). $^1$H NMR (CHLOROFORM-d) δ: 8.09 (d, J=8.5 Hz, 1H), 7.95 (d, J=9.0 Hz, 1H), 7.52 (d, J=8.8 Hz, 1H), 7.39 (dd, J=9.3, 2.5 Hz, 1H), 7.08 (d, J=2.5 Hz, 1H), 4.40 (q, J=7.0 Hz, 2H), 4.09 (t, J=6.5 Hz, 2H), 2.40 (s, 3H), 1.82-1.93 (m, 2H), 1.45-1.56 (m, 2H), 1.26-1.44 (m, 9H), 0.92 (t, J=6.7 Hz, 3H). MS (M+1): 389.30.

Example 37: Ethyl 2-amino-2-(6-heptyloxyquinolin-2-yl)propanoate

Ethyl 2-(6-heptyloxyquinolin-2-yl)-2-nitropropanoate (325.0 mg, 0.0008366 mol) was dissolved in acetic acid (5 mL, 0.09 mol), and cooled to at 10° C., followed by zinc (547.1 mg, 0.008366 mol;) in very small portions to keep the temperature constant. The reaction mixture was then allowed to stir for additional for 5 hours, and filtered through a Celite pad. The excess of solvents were removed under vacuum, and the residue was purified via HPLC (10-100% acetonitrile with 0.1% formic acid) to give a pure product (57.0 mg, 14%). $^1$H NMR (CHLOROFORM-d) δ: 8.05 (d, J=8.5 Hz, 1H), 7.94 (d, J=9.3 Hz, 1H), 7.57 (d, J=8.5 Hz, 1H), 7.36 (dd, J=9.3, 2.5 Hz, 1H), 7.06 (d, J=2.5 Hz, 1H), 4.20 (q, J=7.0 Hz, 2H), 4.07 (t, J=6.5 Hz, 2H), 1.77-1.93 (m, 5H), 1.44-1.57 (m, 2H), 1.28-1.44 (m, 6H), 1.22 (t, J=7.2 Hz, 3H), 0.90 (t, J=6.8 Hz, 3H). MS (M+1): 359.30.

Example 38: 2-amino-2-(6-(heptyloxy)quinolin-2-yl)propan-1-ol

Ethyl 2-amino-2-(6-heptyloxyquinolin-2-yl)propanoate (7, 5.0 mg, 0.000014 mol) was dissolved in a mixture of methanol (1.0 mL, 0.025 mol) and tetrahydrofuran (1.0 mL, 0.012 mol), followed by sodium tetrahydroborate (1.06 mg, 0.0000279 mol) in small portions at 23° C. The reaction mixture was then allowed to stir for 2 hours. The reaction mixture was quenched with NH$_4$Cl (sat), and solvents were removed under vacuum. The solid residue was then treated with MeOH/DCM, and the crude product was purified via HPLC to give pure product (4 mg, 70%). $^1$H NMR (CHLOROFORM-d) δ: 8.22 (d, J=8.5 Hz, 1H), 7.97 (d, J=9.3 Hz, 1H), 7.39-7.51 (m, 2H), 7.10 (d, J=2.5 Hz, 1H), 4.14 (br. s., 2H), 4.08 (t, J=6.5 Hz, 2H), 1.81-1.93 (m, 2H), 1.77 (s, 3H), 1.50 (d, J=8.0 Hz, 2H), 1.21-1.44 (m, 6H), 0.81-0.99 (m, 3H). MS (ES, M+1): 317.30.

Example 39: 5-(Heptyloxy)-2-nitrobenzaldehyde

5-Hydroxy-2-nitrobenzaldehyde (3.60 g, 0.0215 mol), 1-heptanol (2.50 g, 0.0215 mol) and triphenylphosphine polymer bound (3 mmol/g loading; 9 g, 0.028 mol) were placed in a flask followed by tetrahydrofuran (300 mL, 4 mol). A solution of azodicarboxylic acid di-tert-butyl ester (5.94 g, 0.0258 mol) in THF (15 mL) was then added dropwise at 23° C. The reaction mixture was then allowed to stir for 1 day. Filtered through a celite pad, and the crude mixture was then purified via chromatography (SiO$_2$, 120 g, 0-100% ethyl acetate/hexanes) to give a pure product (3.25 g, 57%). $^1$H NMR (CHLOROFORM-d) δ: 10.50 (s, 1H), 8.16 (d, J=9.0 Hz, 1H), 7.32 (d, J=3.0 Hz, 1H), 7.14 (dd, J=9.0, 2.8 Hz, 1H), 4.11 (t, J=6.5 Hz, 2H), 1.76-1.92 (m, 2H), 1.42-1.53 (m, 2H), 1.21-1.42 (m, 6H), 0.82-0.99 (m, 3H). MS (M+1): 266.20.

Example 40: 2-(5-Heptyloxy)-2-nitrophenyl-1,3-dioxolane 5-(heptyloxyl)-2-nitrobenzaldehyde (3, 1.00 g, 0.00377 mol) and 1,2-Bis-trimethylsilanyloxy-ethane (0.924 mL, 0.00377 mol) were placed in a 40 mL vial, followed by methylene chloride (50 mL, 0.8 mol). The reaction mixture was then cooled to −78° C., and trimethylsilyl trifluoromethanesulfonate (0.03 mL, 0.0002 mol) was added dropwise under N$_2$. The reaction mixture was allowed to stir for about for 3 hours at −78° C. The reaction mixture was then warmed up to 23° C., and then cooled down to −78° C. again. A solution of NaOH (4N) was added to quench the reaction, and organic layer was separated. The crude mixture was then purified via chromatography (SiO$_2$, 24 g, 0-35% ethyl acetate/hexanes) to give the desired product (1030 mg, 88%). $^1$H NMR (CHLOROFORM-d) δ: 8.04 (d, J=9.0 Hz, 1H), 7.29 (d, J=2.8 Hz, 1H), 6.91 (dd, J=9.0, 2.8 Hz, 1H), 6.58 (s, 1H), 398-4.12 (m, 6H), 1.74-1.90 (m, 2H), 1.42-1.53 (m, 2H), 1.24-1.41 (m, 6H), 0.83-0.98 (m, 3H). MS (M+1): 310.20.

Example 41: 2-(1,3-Dioxolan-2-yl)-4-heptyloxyaniline 2-(5-Heptyloxy)-2-nitrophenyl-1,3-dioxolane (4, 950.00 mg, 0.0030709 mol), platinum dioxide (40 mg, 0.0002 mol) and sodium acetate trihydrate (30 mg, 0.0002 mol) were placed in a pressure flask, followed by ethyl acetate (50 mL, 0.5 mol). The reaction mixture was then purged under N$_2$ for at least 3 times, and H$_2$ was introduced (purged 3 times) and maintained at 52 psi for 3 hours. The reaction mixture was then filtered, and solvent was removed to give a pure product (855 mg, 100%). $^1$H NMR (CHLOROFORM-d) δ: 6.95 (d, J=2.8 Hz, 1H), 6.76 (dd, J=8.5, 2.8 Hz, 1H), 6.63 (d, J=8.5 Hz, 1H), 5.84 (s, 1H), 4.01-4.18 (m, 4H), 3.81-3.95 (m, 2H), 1.67-1.81 (m, 2H), 1.56 (br. s., 2H), 1.38-1.50 (m, 2H), 1.20-1.38 (m, 4H), 0.84-0.95 (m, 3H). MS (M+1): 280.20.

Example 42: (R)-Methyl 3-(methoxymethoxy)-2-methylpropanoate (R)-3-Hydroxy-2-methyl-propionic acid methyl ester (8.60 g, 0.0728 mol) was dissolved in methylene chloride (200 mL, 3 mol), followed by N,N-diisopropylethylamine (25.4 mL, 0.146 mol). The reaction mixture was then cooled to −78° C., and chloromethyl methyl ether (9.48 mL, 0.0874 mol) was added dropwise. The reaction mixture was then allowed to warm up gradually over for 5 hours to 23° C., and quenched with Na$_2$CO$_3$ (sat). Organic layer was separated, and washed with water, brine, and then dried over Na$_2$SO$_4$. The crude mixture was purified via chromatography (SiO$_2$, 120 g, 0-30% ethyl acetate/hexanes) to give 10.3 g clear liquid product (87%). $^1$H NMR (CHLOROFORM-d) δ: 4.61 (s, 2H), 3.71 (m, 4H), 3.58 (dd, J=9.5, 5.5 Hz, 1H), 3.35 (s, 3H), 2.77 (m, 1H), 1.19 (d, J=7.0 Hz, 3H).

Example 43: (R)-3-(methoxymethoxy)-2-methylpropanoic acid (R)-Methyl 3-(methoxymethoxy)-2-methylpropanoate (7, 5.00 g, 0.0308 mol) was dissolved in methanol (50 mL, 1 mol). The solution was then cooled to −78° C. Sodium methoxide (5.26 g, 0.0925 mol), was added gradually (in very small portions) followed by water (1.11 mL, 0.0616 mol) at −78° C. The reaction mixture was then stirred at 23° C. for 12 hours. An additional portion of NaOMe (95%, 1.0 g) was added to the reaction mixture followed by H$_2$O (0.8 mL). The reaction mixture was allowed to stir at 23° C. for 4 hours. All the solvents were removed under vacuum, and before quenched with concentrated HCl to pH~5. Excess of solvents were removed under vacuum. The residue was extracted with DCM (50×3 mL). The combined organic layers were treated with water, brine and dried over Na$_2$SO$_4$. Removal of solvent gave a liquid product (4.37 g, 96%). $^1$H NMR (CHLOROFORM-d) δ: 4.64 (s, 2H), 3.69-3.82 (m, 1H), 3.56-3.68 (m, 1H), 3.37 (s, 3H), 2.80 (m, 1H), 1.23 (d, J=7.3 Hz, 3H).

Example 44: (R)—N-2-(1,3-Dioxolan-2-yl)-4-heptyloxyphenyl-3-methoxymethoxy-2-methylpropanamide (R)-3-(methoxymethoxy)-2-methylpropanoic acid (1.27 g, 0.00859 mol) was dissolved in methylene chloride (20 mL, 0.4 mol), and cooled to at −78° C., followed by oxalyl chloride (0.909 mL, 0.0107 mol) and catalytic amounts of N,N-dimethylformamide (0.006 mL, 0.00007 mol). The reaction mixture was allowed to warm up gradually until bubbles appeared. The reaction mixture was then maintained at that temperature until bubbling ceased. The reaction mixture was then cooled down again to at −78° C. and excess reagent and solvent were removed under vacuum. The crude residue was then re-dissolved in THF (5 mL), and added drop wise to a solution of 2-(1,3-dioxolan-2-yl)-4-heptyloxyaniline (2.00 g, 0.00716 mol) and triethylamine (2.00 mL, 0.0143 mol) in tetrahydrofuran (60 mL, 0.8 mol) at −78° C. The reaction mixture was then gradually warmed up to at 23° C. for additional 2 hours before quenched with sat Na$_2$CO$_3$. Solvents were removed under vacuum, and the residue was treated with DCM (50×3 mL). Combined organic layers were dried over Na$_2$SO$_4$, and purified via chromatography (SiO$_2$, 40 g, 0-50% ethyl acetate/hexanes) to give a desired product (2.83 g, 97%). $^1$H NMR (CHLOROFORM-d) δ: 8.48 (br. s., 1H), 7.97 (d, J=8.8 Hz, 1H), 7.02 (d, J=2.8 Hz, 1H), 6.88 (dd, J=8.9, 2.9 Hz, 1H), 5.88 (s, 1H), 4.66 (s, 2H), 4.01-4.18 (m, 4H), 3.95 (t, J=6.5 Hz, 2H), 3.71-3.81 (m, 1H), 3.66 (dd, J=9.5, 4.8 Hz, 1H), 3.36 (s, 3H), 2.60-2.76 (m, 1H), 1.69-1.84 (m, 2H), 1.58 (br. s., 2H), 1.39-1.51 (m, 2H), 1.15-1.39 (m, 7H), 0.90 (t, J=6.7 Hz, 3H). MS (M+1): 410.30.

Example 45: (R)—N-(2-Formyl-4-heptyloxyphenyl)-3-methoxymethoxy-2-methylpropanamide (R)—N-2-(1,3-Dioxolan-2-yl)-4-heptyloxyphenyl-3-methoxymethoxy-2-methylpropanamide (2.80 g, 0.00684 mol) was dissolved in acetone (20 mL, 0.2 mol), followed by 6 M hydrogen chloride in water (5 mL) at 0° C. The reaction mixture was then gradually warmed up to 23° C. for 1 hour. NaHCO$_3$ (sat) was then added to give pH~7. Acetone was removed under vacuum, and the residue was extracted with DCM (50×3 mL). The combined organic layers were then dried over Na$_2$SO$_4$. Removal of solvent gave the desired product (2.50 g, 100%). $^1$H NMR (CHLOROFORM-d) δ: 11.00 (br. s., 1H), 9.89 (s, 1H), 8.72 (d, J=9.5 Hz, 1H), 7.06-7.22 (m, 2H), 4.65 (s, 2H), 4.00 (t, J=6.7 Hz, 2H), 3.74-3.87 (m, 1H), 3.66 (dd, J=9.8, 5.0 Hz, 1H), 3.35 (s, 3H), 2.79 (m, 1H), 1.68-1.89 (m, 2H), 1.58 (br. s., 2H), 1.17-1.52 (m, 9H), 0.91 (t, J=6.8 Hz, 3H). MS (M+1): 366.30.

Example 46: (S)-6-Heptyloxy-2-(1-methoxymethoxypropan-2-yl)quinazoline (R)—N-(2-Formyl-4-heptyloxyphenyl)-3-methoxymethoxy-2-methylpropanamide (2.50 g, 0.00684 mol) was dissolved in methanol (200 mL, 5 mol), and cooled to −78° C., followed by ammonia (20 g, 1 mol) bubbling for 3 hours. The reaction mixture was then transferred to a pre-cooled high pressure reactor, and heated at 130° C. for 15 hours (310 psi). Solvent was removed, and the crude mixture was purified via chromatography (SiO$_2$, 40 g, 0-60% ethyl acetate/hexanes) to give the desired product (1.78 g, 75%). $^1$H NMR (CHLOROFORM-d) δ: 9.26 (s, 1H), 7.90 (d, J=9.3 Hz, 1H), 7.52 (dd, J=9.2, 2.6 Hz, 1H), 7.10 (d, J=2.3 Hz, 1H), 4.55-4.68 (m, 2H), 4.02-4.16 (m, 3H), 3.85 (dd, J=9.4, 6.4 Hz, 1H), 3.45-3.61 (m, 1H), 3.27 (s, 3H), 1.79-1.95 (m, 2H), 1.45-1.57 (m, 2H), 1.27-1.45 (m, 9H), 0.91 (t, J=6.7 Hz, 3H). MS (M+1): 347.30.

Example 47: (S)-2-(6-Heptyloxyquinazolin-2-yl)propan-1-ol (S)-6-Heptyloxy-2-(1-methoxymethoxypropan-2-yl)quinazoline (1500 mg, 0.0043 mol) was dissolved in methanol (60 mL, 1 mol), followed by 6 M hydrogen chloride in water (20 mL) and at 0° C. The reaction mixture was then heated at 80° C. for 30 minutes. Saturated K$_2$CO$_3$ was then added in small portions (pH~8), and MeOH was removed under vacuum. The aqueous layer was treated with DCM (50×5 mL). The combined organic layers were then washed with water and brine, and then dried over Na$_2$SO$_4$. The crude mixture was purified via chromatography (SiO$_2$, 4 g, 0-100% ethyl acetate/hexanes) to give 1.10 g (84%), and 189 mg of methyl ether side product. $^1$H NMR (CHLOROFORM-d) δ: 9.25 (s, 1H), 7.88 (d, J=9.3 Hz, 1H), 7.49-7.62 (m, 1H), 7.12 (d, J=2.5 Hz, 1H), 4.18-4.29 (m, 1H), 4.04-4.15 (m, 3H), 3.90-4.03 (m, 1H), 3.39 (m, 1H), 1.79-1.97 (m, 2H), 1.21-1.60 (m, 11H), 0.92 (t, J=6.8 Hz, 3H). MS (M+1): 303.30.

Example 48: (S)-2-(6-Heptyloxyquinazolin-2-yl)propyl carbamate (S)-2-(6-Heptyloxy-quinazolin-2-yl)-propan-1-ol (13, 950 mg, 0.0031 mol) was dissolved in methylene chloride (100 mL, 2 mol), followed by trichloroacetyl isocyanate (449 μL, 0.00377 mol) dropwise at 0° C. The reaction mixture was then gradually warmed up to 23° C., and stirred for additional for 1 hour. Solvent was removed under vacuum, and the residue was redissolved in methanol (100 mL, 3 mol), followed by potassium carbonate (5000 mg, 0.03 mol) and water (20 mL, 1 mol) at 0° C. The reaction mixture was then warmed up to at 23° C. and stirred for 3 hours. MeOH was removed under vacuum, and the aqueous layer was treated with DCM (10×5 mL). The combined organic layers were then washed with water and brine, and then dried over Na$_2$SO$_4$. The crude mixture was purified via chromatography (SiO$_2$, 4 g, 0-100% ethyl acetate/hexanes) to give 1.05 g, (97%). $^1$H NMR (400 MHz, CHLOROFORM-d) δ: 9.24 (s, 1H), 7.89 (d, J=9.3 Hz, 1H), 7.53 (dd, J=9.0, 2.8 Hz, 1H), 7.11 (d, J=2.8 Hz, 1H), 4.60 (dd, J=10.5, 8.0 Hz, 1H), 4.51 (br. s., 2H), 4.45 (dd, J=10.5, 6.0 Hz, 1H), 4.09 (t, J=6.5 Hz, 2H), 3.47-3.62 (m, 1H), 1.81-1.92 (m, 2H), 1.40-1.65 (m, 11H), 0.82-0.96 (m, 3H). MS (ES, M+1): 346.30.

Example 49: (R)-4-(6-Heptyloxyquinazolin-2-yl)-4-methyloxazolidin-2-one (S)-2-(6-Heptyloxyquinazolin-2-yl)propyl carbamate (14, 350 mg, 0.0010 mol) was dissolved in toluene (20 mL, 0.2 mol), followed by magnesium monoxide (93.9 mg, 0.00233 mol), iodobenzene diacetate (359 mg, 0.00111 mol) and finally Rh$_2$(esp)$_2$ (35 mg, 0.000046 mol). The reaction mixture was then heated at 40° C. for 3 days. DCM was added to the reaction mixture, and the reaction mixture was filtered. The crude mixture was then purified via chromatography (SiO$_2$, 12 g, 0-80% ethyl acetate/hexanes) to give 53 mg of the desired product (15%) and 215.0 mg of 14. $^1$H NMR (CHLOROFORM-d) δ: 9.27 (s, 1H), 7.90 (d, J=9.3 Hz, 1H), 7.58 (dd, J=9.2, 2.6 Hz, 1H), 7.15 (d, J=2.5 Hz, 1H), 6.19 (br. s., 1H), 5.18 (d, J=8.5 Hz, 1H), 4.49 (d, J=8.8 Hz, 1H), 4.11 (t, J=6.5 Hz, 2H), 1.80-1.97 (m, 2H), 1.76 (s, 3H), 1.21-1.60 (m, 8H), 0.91 (t, J=6.7 Hz, 3H). MS (M+1): 344.30.

Example 50: (R)-2-Amino-2-(6-heptyloxyquinazolin-2-yl)propan-1-ol (R)-4-(6-Heptyloxy-quinazolin-2-yl)-4-methyl-oxazolidin-2-one (40.0 mg, 0.000116 mol) was dissolved in ethanol (2 mL, 0.03 mol), followed by 4 M lithium hydroxide in water (1 mL). The reaction mixture was then heated at 80° C. for 2 hours. All solvent was removed. The solid was extracted with DCM, and was purified via chromatography (SiO$_2$, 4 g, 0-100% (10% of MeOH with 2N ammonia in DCM and DCM) to give the desired product (21 mg, 57%). $^1$H NMR (CHLOROFORM-d) δ: 9.25 (s, 1H), 7.87 (d, J=9.0 Hz, 1H), 7.49 (dd, J=9.7, 2.4 Hz, 1H), 7.08 (d, J=2.5 Hz, 1H), 6.60 (br. s., 3H), 4.26 (d, J=11.8 Hz, 1H), 4.17 (d, J=11.8 Hz, 1H), 4.06 (t, J=6.7 Hz, 2H), 1.81-2.00 (m, 4H), 1.77 (s, 3H), 1.43-1.61 (m, 2H), 1.20-1.43 (m, 4H), 0.84-1.01 (m, 3H). MS (ES, M+1): 318.30.

Example 51: (R)-2-Amino-2-(6-(heptyloxy)quinazolin-2-yl)propyl dihydrogen phosphate A three step procedure similar to that used for phosphoric acid mono-{2-amino-2-[6-(4-tert-butyl-cyclohexyloxy)-quinolin-2-yl]-propyl}ester Enantiomer 1 (Examples 28-30) was used to make the title compound from (R)-2-amino-2-(6-heptyloxyquinazolin-2-yl)propan-1-ol. $^1$H NMR (MeOD) δ: 9.49 (s, 1H), 8.01 (d, J=9.3 Hz, 1H), 7.69 (dd, J=9.2, 2.6 Hz, 1H), 7.49 (d, J=2.8 Hz, 1H), 4.63 (dd, J=10.8, 4.8 Hz, 1H), 4.47 (dd, J=10.9, 4.9 Hz, 1H), 4.18 (t, J=6.4 Hz, 2H), 1.83-1.96 (m, 2H), 1.81 (s, 3H), 1.48-1.60 (m, 2H), 1.23-1.47 (m, 6H), 0.84-0.99 (m, 3H). MS (M+1): 398.30.

Example 52: 5-Methoxy-2-nitrobenzaldehyde

5-Hydroxy-2-nitrobenzaldehyde (25.0 g, 150 mmol) was dissolved in N,N-dimethylformamide (200 mL, 2000 mmol), followed by potassium carbonate (20.7 g, 150 mmol) and methyl iodide (10.2 mL, 164 mmol). The reaction mixture was stirred for 10 hours at 23° C. Ethyl acetate (1000 mL) was added, and the mixture was washed with water and brine. Organic layer was dried over sodium sulfate. Removal of solvent gave a crude solid product, which was treated with DCM and hexanes. The solid was collected and washed with hexanes (27.0 g, 100%). $^1$H NMR (CHLOROFORM-d) δ: 10.50 (s, 1H), 8.18 (d, J=9.0 Hz, 1H), 7.34 (d, J=2.8 Hz, 1H), 7.16 (dd, J=9.2, 2.9 Hz, 1H), 3.97 (s, 3H). MS (M+1): 182.10.

Example 53: 2-(5-Methoxy-2-nitrophenyl)-1,3-dioxolane

5-Methoxy-2-nitro-benzaldehyde (30.00 g, 0.1656 mol) and 1,2-bis-trimethylsilanyloxy-ethane (40.6 mL, 0.166 mol) were placed in a 40 mL vial, followed by Methylene chloride (1000 mL, 20 mol). The reaction mixture was then cooled to −78° C., and trimethylsilyl trifluoromethanesulfonate (1 mL, 0.008 mol) was added dropwise under N$_2$. The reaction mixture was allowed to warm up to at 23° C. for 1 day. A solution of saturated K$_2$CO$_3$ (50 mL) was added to quench the reaction, and organic layer was separated. Removal of solvent gave a oily product, which was treated with ether/hexanes to give a pure solid product (37.0 g, 99%). $^1$H NMR (MeOD) δ: 8.01 (d, J=9.0 Hz, 1H), 7.29 (d, J=2.8 Hz, 1H), 7.05 (dd, J=8.9, 2.9 Hz, 1H), 6.49 (s, 1H), 4.85 (s, 3H), 3.91 (s, 4H). MS (M+1): 226.10.

Example 54: 2-(1,3-Dioxolan-2-yl)-4-methoxyaniline 2-(5-Methoxy-2-nitrophenyl)-1,3-dioxolane (15.00 g, 0.06661 mol), platinum dioxide (900 mg, 0.004 mol) and sodium acetate trihydrate (700 mg, 0.005 mol) were placed in a pressure flask, followed by ethyl acetate (400 mL, 4 mol). The reaction mixture was then purged under N$_2$ for at least 3 times, and H$_2$ was introduced (purged 3 times) and maintained at 52 psi for 3 hours. The reaction mixture was then filtered, and solvent was removed to give a pure product (13 g, 100%). $^1$H NMR (CHLOROFORM-d) δ: 6.96 (d, J=2.8 Hz, 1H), 6.76 (dd, J=8.5, 3.0 Hz, 1H), 6.64 (d, J=8.5 Hz, 1H), 5.84 (s, 1H), 4.00-4.18 (m, 4H), 3.89 (br. s., 2H). MS (M+1): 196.10.

Example 55: (S)-tert-Butyl 1-(2-(1,3-dioxolan-2-yl)-4-methoxyphenylamino)-3-hydroxy-2-methyl-1-oxopropan-2-ylcarbamate (S)-2-tert-Butoxycarbonylamino-3-hydroxy-2-methyl-propionic acid (247.1 mg, 0.001127 mol) was dissolved in DMF, followed by N,N-diisopropylethylamine (0.892 mL, 0.00512 mol), and then 2-(1,3-dioxolan-2-yl)-4-methoxyaniline (200.0 mg, 0.001024 mol) and N,N,N',N'-tetramethyl-O-(7-azabenzotriazol-1-yl)uronium hexafluorophosphate (389.5 mg, 0.001024 mol) at 23° C. The reaction mixture was allowed to stir at 23° C. for 10 hours. Ethyl acetate (50 mL) was added, followed by water (10 mL). Organic layer was separated, and the aqueous layer was extracted with additional ethyl acetate (2×10 mL). Combined organic layers were washed with water (3×10 mL), brine and dried over Na$_2$SO$_4$. The crude product was purified via chromatography (SiO$_2$, 12 g, 0-50% ethyl acetate/hexanes) to give the desired product (176 mg, 43%). $^1$H NMR (MeOD) δ: 7.98 (s, 1H), 7.01 (d, J=3.0 Hz, 1H), 6.93 (dd, J=8.9, 2.9 Hz, 1H), 5.76 (s, 1H), 4.13-4.26 (m, 2H), 3.95-4.09 (m, 2H), 3.69-3.85 (m, 7H), 1.37-1.53 (m, 12H). MS (M+1): 397.20.

Example 56: (R)-2-Amino-2-(6-methoxyquinazolin-2-yl)propan-1-ol

[(S)-1-(2-1,3-Dioxolan-2-yl-4-methoxy-phenylcarbamoyl)-2-hydroxy-1-methyl-ethyl]-carbamic acid tert-butyl ester (20 g, 50 mmol) was dissolved in MeOH (50 mL), and cooled to around −30° C. 6 M Hydrogen chloride in water (10.09 mL, 60.54 mmol) was added and the reaction mixture was allowed to warm to at 23° C. over for 2 hours. All the solvents were removed under vacuum and the residue was re-dissolved in MeOH (20 mL) and cooled to −78° C. This solution was then added to a solution of ammonia in MeOH (80 mL, with ammonia gas bubbled through for 3 h at −78° C.). The mixture was then transferred to a high pressure vessel, and heated at 130° C. for 6 hours (320 psi). The mixture was filtrated and the residue was purified via chromatography (SiO$_2$, 120 g, 0-20% MeOH/DCM) to give 3.1 g of pure product (30%). $^1$H NMR (CHLOROFORM-d) δ: 9.28 (s, 1H), 7.90 (d, J=9.4 Hz, 1H), 7.56 (dd, J=9.3, 2.8

Hz, 1H), 7.14 (d, J=2.6 Hz, 1H), 4.07 (d, J=11.0 Hz, 1H), 3.97 (s, 3H), 3.84 (d, J=10.6 Hz, 1H), 2.67 (br. s., 3H), 1.57 (s, 3H). MS (M+1): 234.10.

Example 57: (R)-4-(6-Methoxyquinazolin-2-yl)-4-methyloxazolidin-2-one (R)-2-Amino-2-(6-methoxy-quinazolin-2-yl)-propan-1-ol (3.10 g, 13.3 mmol) was dissolved in methylene chloride (60 mL, 900 mmol), followed by N,N-diisopropylethylamine (6.94 mL, 39.9 mmol). The mixture was then cooled down to −78° C., and triphosgene (4.34 g, 14.6 mmol) was added in small portions over for 1 hour. The reaction mixture was then warmed up to 23° C. gradually and stirred for additional for 3 hours. Quenched with $K_2CO_3$ (sat), and organic layer was separated. The aqueous layer was extracted with DCM (2×20 mL) and combined organic layers were washed with water, brine and dried over $Na_2SO_4$. The crude product was then purified via chromatography ($SiO_2$, 40 g, 0-10% MeOH/DCM) (1.78 g, 51%). $^1$H NMR (CHLOROFORM-d) δ: 9.29 (s, 1H), 7.90 (d, J=9.4 Hz, 1H), 7.58 (dd, J=9.1, 2.6 Hz, 1H), 7.16 (d, J=2.6 Hz, 1H), 6.29 (br. s., 1H), 5.18 (d, J=8.7 Hz, 1H), 4.49 (d, J=8.7 Hz, 1H), 3.97 (s, 3H), 1.76 (s, 3H). MS (M+1): 260.10.

Example 58: (R)-4-(6-Hydroxyquinazolin-2-yl)-4-methyloxazolidin-2-one (R)-4-(6-Methoxy-quinazolin-2-yl)-4-methyl-oxazolidin-2-one (860.0 mg, 3.317 mmol) was dissolved in methylene chloride (60 mL, 900 mmol), and cooled to −78° C. A solution of 1.0 M of boron tribromide in nethylene chloride (9.95 mL, 9.95 mmol) was then added dropwise. The reaction mixture was then warmed up to at 23° C. gradually and then heated at 50° C. for 2 hours. The reaction mixture was then question with $NaHCO_3$ (sat) to basic, and neutralized back to pH-7-8. DCM was removed under vacuum, the white solid was collected and washed with water and hexanes (560 mg, 69%). $^1$H NMR (MeOD) δ: 9.32 (s, 1H), 7.91 (d, J=9.3 Hz, 1H), 7.57 (dd, J=9.0, 2.8 Hz, 1H), 7.26 (d, J=2.5 Hz, 1H), 4.98 (d, J=8.5 Hz, 1H), 4.46 (d, J=8.5 Hz, 1H), 1.78 (s, 3H). MS (M+1): 246.10.

Example 59: (R)-4-(6-Hydroxy-5-iodoquinazolin-2-yl)-4-methyloxazolidin-2-one (R)-4-(6-Hydroxy-quinazolin-2-yl)-4-methyl-oxazolidin-2-one (330.0 mg, 0.001346 mol) was dissolved in methylene chloride (500 mL, 8 mol), (heterogeneous) followed by N-iodosuccinimide (302.8 mg, 0.001346 mol) at 23° C. The reaction mixture was then sonicated for 30 seconds, and all the solvent was removed under vacuum (rotavap). The residue was purified via chromatography ($SiO_2$, 20 gm, 0-100% ethyl acetate/hexanes) to give 420 mg of desired product (84%). $^1$H NMR (MeOD) δ: 9.50 (s, 1H), 7.90 (d, J=9.0 Hz, 1H), 7.60 (d, J=9.0 Hz, 1H), 4.99 (d, J=8.8 Hz, 1H), 4.48 (d, J=8.8 Hz, 1H), 1.79 (s, 3H). MS (M+1): 372.00.

Example 59A: (R)-4-(6-(trans-4-tert-Butylcyclohexyloxy)-5-iodoquinazolin-2-yl)-4-methyloxazolidin-2-one (R)-4-(6-Hydroxy-5-iodo-quinazolin-2-yl)-4-methyl-oxazolidin-2-one (350.0 mg, 0.0009431 mol), methanesulfonic acid 4-tert-butyl-cyclohexyl ester (884.0 mg, 0.003772 mol) and cesium carbonate (921.8 mg, 0.002829 mol) were dissolved in a mixture of tert-butyl alcohol (19.9 mL, 0.208 mol) and 2-butanone (6.6 mL, 0.074 mol). The reaction mixture was heated at 80° C. for 1 hour (MW), an additional methanesulfonic acid 4-tert-butyl-cyclohexyl ester (500 mg) was added, and the mixture was heated at 80° C. for an additional for 1 hour. LC/MS indicated that reaction was completed. Removal of solvents gave a solid mixture, which was treated with DCM and filtered. The filtrate was then washed with water, brine and dried over $Na_2SO_4$. The crude mixture was then purified via chromatography ($SiO_2$, 24 gm, 0-100% ethyl acetate/hexanes) to give 451 mg desired product (94%). $^1$H NMR (CHLOROFORM-d) δ: 9.55 (s, 1H), 7.94 (d, J=9.3 Hz, 1H), 7.61 (d, J=9.3 Hz, 1H), 6.07 (s, 1H), 5.16 (d, J=8.8 Hz, 1H), 4.50 (d, J=8.8 Hz, 1H), 4.24-4.42 (m, 1H), 2.24 (d, J=12.0 Hz, 2H), 1.92 (d, J=9.5 Hz, 2H), 1.76 (s, 3H), 1.63 (d, J=11.3 Hz, 1H), 1.22-1.39 (m, 2H), 1.15 (br. s., 2H), 0.81-0.98 (m, 9H). MS (M+1): 510.10.

Example 60: (R)-4-(6-(trans-4-tert-Butylcyclohexyloxy)-5-(trifluoromethyl)quinazolin-2-yl)-4-methyloxazolidin-2-one (R)-4-[6-(4-tert-Butyl-cyclohexyloxy)-5-iodo-quinazolin-2-yl]-4-methyl-oxazolidin-2-one (360.0 mg, 0.0007067 mol) and copper(I) iodide (202 mg, 0.00106 mol) were placed in a vial, and purged with $N_2$. N,N-cimethylformamide (10.0 mL, 0.129 mol) was added followed by hexamethylphosphoramide (0.700 mL, 0.00402 mol). Methyl fluorosulphonyldifluoroacetate (0.900 mL, 0.00707 mol) was added dropwise at 23° C. The reaction mixture was then heated to 80° C. for 40 min. The reaction mixture was then cooled to at 23° C., and filtrated. Majority of the solvent was removed under vacuum, and water was added to the residue solution and extracted with DCM (25×3 mL). Combined organic layers were dried over $Na_2SO_4$, and purified via chromatography ($SiO_2$, 12 gm, 0-50% ethyl acetate/hexanes) to give 197 mg of the desired product (62%). $^1$H NMR (CHLOROFORM-d) δ: 9.75 (s, 1H), 8.12 (d, J=9.4 Hz, 1H), 7.76 (d, J=9.4 Hz, 1H), 6.18 (s, 1H), 5.14 (d, J=9.1 Hz, 1H), 4.48 (d, J=8.7 Hz, 1H), 4.27-4.45 (m, 1H), 2.20 (d, J=11.3 Hz, 2H), 1.81-2.00 (m, 2H), 1.76 (s, 3H), 1.45-1.68 (m, 1H), 1.03-1.36 (m, 4H), 0.78-0.94 (m, 9H). MS (M+1): 452.20.

Example 61: (R)-2-Amino-2-(6-(trans-4-tert-butylcyclohexyloxy)-5-(trifluoromethyl)quinazolin-2-yl)propan-1-ol (R)-4-[6-(4-tert-Butyl-cyclohexyloxy)-5-trifluoromethyl-quinazolin-2-yl]-4-methyl-oxazolidin-2-one (180.0 mg, 0.0003987 mol) was dissolved in ethanol (7 mL, 0.1 mol), followed by 4 M lithium hydroxide in water (3 mL, 0.01 mol). The reaction mixture was then heated at 80° C. for 2 hours. All solvent was removed. The solid was extracted with DCM, and organic layers were dried over $Na_2SO_4$. Removal of solvent gave a pure product (152 mg, 90%). $^1$H NMR (MeOD) δ: 9.73 (s, 1H), 8.24 (d, J=9.3 Hz, 1H), 8.05 (d, J=9.5 Hz, 1H), 4.50-4.68 (m, 1H), 4.11 (d, J=11.0 Hz, 1H), 3.84 (d, J=11.0 Hz, 1H), 2.22 (d, J=10.8 Hz, 2H), 1.92 (d, J=13.1 Hz, 2H), 1.61 (s, 3H), 1.43-1.58 (m, 2H), 1.18-1.35 (m, 2H), 1.04-1.18 (m, 1H), 0.91 (s, 9H). MS (M+1): 426.30.

Example 62: (R)-2-amino-2-(6-(trans-4-tert-butylcyclohexyloxy)-5-(trifluoromethyl)quinazolin-2-yl)propyl dihydrogen phosphate A three step procedure similar to that used for phosphoric acid mono-{2-amino-2-[6-(4-tert-butyl-cyclohexyloxy)-quinolin-2-yl]-propyl}ester Enantiomer 1 (Examples 28-30) was used to make the title compound from (R)-2-amino-2-(6-(trans-4-tert-butylcyclohexyloxy)-5-(trifluoromethyl) quinazolin-2-yl)propan-1-ol. $^1$H NMR (MeOD) δ: 9.81 (s, 1H), 8.29 (d, J=9.5 Hz, 1H), 8.13 (d, J=9.5 Hz, 1H), 4.55-4.70 (m, 2H), 4.44 (dd, J=10.9, 4.9 Hz, 1H), 2.23 (d, J=11.0 Hz, 2H), 1.93 (d, J=13.1 Hz, 2H), 1.81 (s, 3H), 1.43-1.65 (m, 2H), 1.18-1.37 (m, 2H), 1.04-1.19 (m, 1H), 0.92 (s, 9H). MS (M+1): 506.20.

Example 63: (R)-2-Amino-2-(6-(trans-4-tert-butyl-cyclohexyloxy)quinazolin-2-yl)propan-1-ol Coupling of t-butyl cyclohexane to the core was performed similar to that described for (R)-4-(6-(trans-4-tert-butylcyclohexyloxy)-5-iodoquinazolin-2-yl)-4-methyloxazolidin-2-one (Example 60) utilizing (R)-4-(6-hydroxyquinazolin-2-yl)-4-methyloxazolidin-2-one as the starting material. Deprotection was then performed similar to that described for (R)-2-amino-2-(6-(trans-4-tert-butylcyclohexyloxy)-5-(trifluoromethyl)quinazolin-2-yl)propan-1-ol (Example 61) to give the title compound. $^1$H NMR (MeOD) δ: 9.37 (s, 1H), 7.92 (d, J=9.3 Hz, 1H), 7.57 (dd, J=9.2, 2.6 Hz, 1H), 7.42 (d, J=2.5 Hz, 1H), 4.34-4.49 (m, 1H), 4.05 (d, J=10.8 Hz, 1H), 3.79 (d, J=10.8 Hz, 1H), 2.29 (d, J=10.8 Hz, 2H), 1.93 (d, J=12.8 Hz, 2H), 1.54 (s, 3H), 1.38-1.51 (m, 2H), 1.21-1.35 (m, 2H), 1.08-1.19 (m, 1H), 0.93 (s, 9H). MS (M+1): 358.20.

Example 64: tert-butyl (R)-2-((R)-6-(trans-4-tert-butylcyclohexyloxy)-1,2,3,4-tetrahydronaphthalen-2-yl)-1-hydroxypropan-2-ylcarbamate (R)-2-Amino-2-((R)-6-(trans-4-tert-butylcyclohexyloxy)-1,2,3,4-tetrahydronaphthalen-2-yl)propan-1-ol (Example 11) (30.0 mg, 0.0000834 mol) in chloroform (4 mL, 0.05 mol) and saturated aqueous sodium bicarbonate solution (2 mL, 0.02 mol) was added di-tert-butyldicarbonate (27.3 mg, 0.000125 mol) and the mixture was stirred at rt for 24 h. TLC shows complete reaction. After separation of organic layer, the aqueous layer was extracted with CHCl$_3$. The organic layer was washed with brine and dried over anhydrous Na$_2$SO$_4$. The concentrated residue was chromatographed with MeOH/CH$_2$Cl$_2$ (0-55%) to give tert-butyl (R)-2-((R)-6-(trans-4-tert-butylcyclohexyloxy)-1,2,3,4-tetrahydronaphthalen-2-yl)-1-hydroxypropan-2-ylcarbamate (38.4 mg, 100%).

Example 65: (R)-2-((R)-6-(trans-4-tert-butylcyclohexyloxy)-1,2,3,4-tetrahydronaphthalen-2-yl)-1-(phosphonooxy-o-xylylene)propan-2-ylcarbamate To a solution of tert-butyl (R)-2-((R)-6-(trans-4-tert-butylcyclohexyloxy)-1,2,3,4-tetrahydronaphthalen-2-yl)-1-hydroxypropan-2-ylcarbamate (38.4 mg, 0.0000835 mol) and 1H-tetrazole (17.6 mg, 0.000251 mol) in tetrahydrofuran (0.88 mL, 0.011 mol) was added o-xylylene N,N-diethylphosphoramidite (27.0 uL, 0.000125 mol) at rt. The resulting mixture was stirred at rt for 3 d, then hydrogen peroxide (190 uL, 0.0018 mol) was added and the mixture was stirred at rt for 1 h. The reaction was quenched with satd. NaS$_2$O$_3$, then extracted with EtOAc, then dried over Na$_2$SO$_4$. The residue was chromatographed with MeOH/CH$_2$Cl$_2$ (0-100%) to give desired product (46.3 mg, 86%). H1NMR confirms the identity.

Example 66: (R)-2-((R)-6-(trans-4-tert-butylcyclohexyloxy)-1,2,3,4-tetrahydronaphthalen-2-yl)-1-(phosphonooxy)propan-2-ylcarbamate The above phosphate (46.3 mg, 0.0000721 mol) in methanol (2.0 mL, 0.049 mol) was added 10% palladium on carbon (1:9, palladium:carbon black, 7.7 mg). The mixture was stirred under hydrogen (0.4 L, 0.02 mol) for 2 h, filtered through Celite and washed with MeOH. The concentrated residue was dissolved in methylene chloride and was chromatographed with MeOH/CH$_2$Cl$_2$ (0-50%) to give tert-butyl (R)-2-((R)-6-(trans-4-tert-butylcyclohexyloxy)-1,2,3,4-tetrahydronaphthalen-2-yl)-1-(phosphonooxy)propan-2-ylcarbamate as a white solid (38.0 mg, 97.6%). $^1$H NMR was consistent with the title compound.

Example 67: (R)-2-amino-2-((R)-6-(trans-4-tert-butylcyclohexyloxy)-1,2,3,4-tetrahydronaphthalen-2-yl)propyl dihydrogen phosphate tert-Butyl (R)-2-((R)-6-(trans-4-tert-butylcyclohexyloxy)-1,2,3,4-tetrahydronaphthalen-2-yl)-1-(phosphonooxy)propan-2-ylcarbamate (38.4 mg, 0.0000712 mol) was dissolved in acetic acid (2.2 mL, 0.039 mol) and 10 M hydrogen chloride in water (0.6 mL) was added and the mixture was stirred for 1 d. Lyophilizing gave (R)-2-amino-2-((R)-6-(trans-4-tert-butylcyclohexyloxy)-1,2,3,4-tetrahydronaphthalen-2-yl)propyl dihydrogen phosphate as a white solid (16.4 mg, 52%). LCMS: Rf=1.57 min 214 nm (440.22, [M+1]+, 100%). $^1$H NMR (400 MHz, MeOD) δ=7.03 (d, J=8.3 Hz, 1H), 6.70 (d, J=10.9 Hz, 1H), 6.66 (s, 1H), 4.26 (dd, J=5.3, 11.1 Hz, 1H), 4.18-4.09 (m, 1H), 4.06 (dd, J=4.2, 11.0 Hz, 1H), 2.98-2.64 (m, 4H), 2.27-2.14 (m, 3H), 2.05 (d, J=10.2 Hz, 1H), 1.89 (d, J=12.3 Hz, 2H), 1.62-1.42 (m, 1H), 1.32 (s, 3H), 1.32-1.29 (m, 1H), 1.28-1.02 (m, 3H), 0.92 (s, 9H).

Example 68: (R)-2-amino-2-((S)-6-(trans-4-tert-butylcyclohexyloxy)-1,2,3,4-tetrahydronaphthalen-2-yl)propyl dihydrogen phosphate The title compound (12.5 mg) was prepared from (R)-2-amino-2-((S)-6-(trans-4-tert-butylcyclohexyloxy)-1,2,3,4-tetrahydronaphthalen-2-yl)propan-1-ol (Example 12) (30.0 mg) following the four step procedure described in Examples 64-67. LCMS: Rf=1.61 min 214 nm (440.30, [M+1]+, 100%). $^1$H NMR (400 MHz, MeOD) δ=6.97 (br. s., 1H), 6.67 (br. s., 1H), 6.62 (br. s., 1H), 4.22 (br. s., 1H), 4.10 (br. s., 1H), 4.03 (br. s., 1H), 3.17-2.49 (m, 4H), 2.15 (br. s., 2H), 1.84 (br. s., 2H), 1.67-1.42 (m, 1H), 1.33 (br. s., 3H), 1.29-1.04 (m, 3H), 0.88 (s, 9H).

Example 69: (R)-4-((S)-6-(trans-4-tert-butylcyclohexyloxy)-5-iodo-1,2,3,4-tetrahydronaphthalen-2-yl)-4-methyloxazolidin-2-one A mixture of (R)-4-((S)-6-(trans-4-tert-butylcyclohexyloxy)-1,2,3,4-tetrahydronaphthalen-2-yl)-4-methyloxazolidin-2-one (100 mg, 0.000259 mol), N-iodosuccinimide (65.4 mg, 0.000290 mol) and zirconium tetrachloride (9.1 mg, 0.000039 mol) in methylene chloride (2.13 mL, 0.0332 mol) was stirred at rt under Ar in a vial for 3 h. The precipitate was filtered off and the residue was purified with silica gel chromatography eluted with EtOAc/hexane (0 to 40%) to give (R)-4-((S)-6-(trans-4-tert-butylcyclohexyloxy)-5-iodo-1,2,3,4-tetrahydronaphthalen-2-yl)-4-methyl1oxazolidin-2-one as a solid (130 mg, 98%). $^1$H NMR shows 1.6:1 mixture of 5-iodo and 7-iodo isomers. LCMS: Rf=2.40 min 512.39 ([M+1], 30%).

Example 70: (R)-4-((S)-6-(trans-4-tert-butylcyclohexyloxy)-5-(trifluoromethyl)-1,2,3,4-tetrahydronaphthalen-2-yl)-4-methyloxazolidin-2-one To a solution of (R)-4-((S)-6-(trans-4-tert-butylcyclohexyloxy)-5-iodo-1,2,3,4-tetrahydronaphthalen-2-yl)-4-methyloxazolidin-2-one (130 mg, 0.254 mmol), hexamethylphosphoramide (0.22 mL, 1.3 mmol) and copper(I) iodide (73 mg, 0.38 mmol) in N,N-dimethylformamide (1 mL, 20 mmol) was added methyl fluorosulphonyldifluoroacetate (0.17 mL, 1.3 mmol). The mixture was heated at 80° C. overnight. After filtration, the solvent was evaporated and the residue was purified with Si gel chromatography eluted with EtOAc/hexane (0 to 40%) to give a mixture of (R)-4-((S)-6-(trans-4-tert-butylcyclohexyloxy)-5-(trifluoromethyl)-1,2,3,4-tetrahydronaphthalen-2-yl)-4-methyloxazolidin-2-one and its 7-$CF_3$ isomer (1.8:1 shown by $^1$H NMR) as a gel (95 mg, 82%). LCMS: Rf=2.41 min, 450.28 (80%).

Example 71: (R)-2-amino-2-((S)-6-(trans-4-tert-butylcyclohexyloxy)-5-(trifluoromethyl)-1,2,3,4-tetrahydronaphthalen-2-yl)propan-1-ol and

Example 71A: (R)-2-amino-2-((S)-6-(trans-4-tert-butylcyclohexyloxy)-7-(trifluoromethyl)-1,2,3,4-tetrahydronaphthalen-2-yl)propan-1-ol (R)-4-((S)-6-(trans-4-tert-butylcyclohexyloxy)-5-(trifluoromethyl)-1,2,3,4-tetrahydronaphthalen-2-yl)-4-methyloxazolidin-2-one and its 7-$CF_3$ isomer (95.0 mg, 0.000209 mol) and lithium hydroxide (55.2 mg, 0.00230 mol) in ethanol (1.3 mL, 0.023 mol) and water (0.44 mL, 0.025 mol) was heated to reflux for overnight. The solvent was removed under vacuum and the residue was partitioned between water/$CH_2Cl_2$. The aqueous was extensively extracted with $CH_2Cl_2$ and the combined organic phase was dried over $Na_2SO_4$. The concentrated residue was taken up into $CH_2Cl_2$ and subjected to chromatography purification with MeOH/$CH_2Cl_2$ (10:90 to 80:20) to give the product (64.1 mg, 72%) as a mixture of (R)-2-amino-2-((S)-6-(trans-4-tert-butylcyclohexyloxy)-5-(trifluoromethyl)-1,2,3,4-tetrahydronaphthalen-2-yl)propan-1-ol and its 7-$CF_3$ isomer (1.8:1 shown by $^1$H NMR). LCMS: Rf=1.79 min 428.17 ([M+1], 100%). The mixture was subjected to SFC separation (Chiralpak AD-H (2×15 cm) 08-9743, 20% methanol (0.1% DEA)/$CO_2$, 100 bar, 50 mL/min) yielded 20 mg of (R)-2-amino-2-((S)-6-(trans-4-tert-butylcyclohexyloxy)-5-(trifluoromethyl)-1,2,3,4-tetrahydronaphthalen-2-yl)propan-1-ol
(Rf=1.82 min, chemical purity>97%, ee>99%). LCMS: Rf=1.79 min 428.17 ([M+1], 100%). $^1$H NMR (400 MHz, MeOD) δ=7.22 (br. s., 1H), 6.96 (br. s., 1H), 4.20 (br. s., 1H), 3.53 (d, J=11.0 Hz, 1H), 3.46 (d, J=11.0 Hz, 1H), 3.11 (d, J=17.1 Hz, 1H), 2.81 (d, J=15.2 Hz, 2H), 2.63 (t, J=13.9 Hz, 1H), 2.22-2.03 (m, 3H), 1.87 (d, J=11.0 Hz, 2H), 1.82-1.70 (m, 1H), 1.51-1.07 (m, 6H), 1.05 (br. s., 3H), 0.91 (br. s., 9H).
and 21 mg of (R)-2-amino-2-((S)-6-(trans-4-tert-butylcyclohexyloxy)-7-(trifluoromethyl)-1,2,3,4-tetrahydronaphthalen-2-yl)propan-1-ol (Rf=3.53 min, chemical purity>98%, ee>99%). LCMS: Rf=1.79 min 428.16 ([M+1], 100%). $^1$H NMR (400 MHz, CHLOROFORM-d) δ=7.27 (s, 1H), 6.72 (s, 1H), 4.15 (tt, J=4.4, 10.8 Hz, 1H), 3.49 (d, J=10.4 Hz, 1H), 3.44 (d, J=10.4 Hz, 1H), 2.93-2.72 (m, 3H), 2.64-2.52 (m, 1H), 2.18 (dd, J=3.0, 12.8 Hz, 2H), 1.97 (ddd, J=2.4, 5.0, 12.5 Hz, 1H), 1.86 (d, J=10.0 Hz, 2H), 1.81-1.71 (m, 1H), 1.66 (br. s., 4H), 1.51-1.34 (m, 3H), 1.19-1.11 (m, 1H), 1.11-1.06 (m, 3H), 0.88 (s, 9H).

Example 72: tert-butyl (R)-2-((S)-6-((trans)-4-tert-butylcyclohexyloxy)-5-(trifluoromethyl)-1,2,3,4-tetrahydronaphthalen-2-yl)-1-hydroxypropan-2-ylcarbamate (R)-2-amino-2-((S)-6-(trans-4-tert-butylcyclohexyloxy)-5-(trifluoromethyl)-1,2,3,4-tetrahydronaphthalen-2-yl)propan-1-ol (Example 70) (30.4 mg, 0.0000711 mol) in chloroform (3 mL, 0.04 mol) and saturated aqueous sodium bicarbonate solution (2 mL, 0.02 mol) was added di-tert-butyldicarbonate (23.3 mg, 0.000107 mol) and the mixture was stirred at rt for 24 h. TLC shows complete reaction. After separation of organic layer, the aqueous layer was extracted with $CHCl_3$. The organic layer was washed with brine and dried over anhydrous $Na_2SO_4$. The concentrated residue was chromatographed with MeOH/$CH_2Cl_2$ (0-55%) to give tert-butyl (R)-2-((S)-6-((trans)-4-tert-butylcyclohexyloxy)-5-(trifluoromethyl)-1,2,3,4-tetrahydronaphthalen-2-yl)-1-hydroxypropan-2-ylcarbamate (37 mg, 99%).

Example 73: tert-Butyl (R)-2-((S)-6-(trans-4-tert-butylcyclohexyloxy)-5-(trifluoromethyl)-1,2,3,4-tetrahydronaphthalen-2-yl)-1-(phosphonooxy-o-xylylene)propan-2-ylcarbamate To a solution of tert-butyl (R)-2-((S)-6-((1r,4S)-4-tert-butylcyclohexyloxy)-5-(trifluoromethyl)-1,2,3,4-tetrahydronaphthalen-2-yl)-1-hydroxypropan-2-ylcarbamate (37.5 mg, 0.0000711 mol) and 1H-tetrazole (14.9 mg, 0.000213 mol) in tetrahydrofuran (0.75 mL, 0.0092 mol) was added o-xylylene N,N-diethylphosphoramidite (23.0 uL, 0.000107 mol) at rt. The resulting mixture was stirred at rt for 1 d, then hydrogen peroxide (160 μL, 0.0016 mol) was added and the mixture was stirred at rt for 1 h. The reaction was quenched with satd. $NaS_2O_3$, then extracted with EtOAc, then dried over $Na_2SO_4$. The residue was chromatographed with MeOH—$CH_2Cl_2$ (0-100%) to give desired phosphate (50 mg, 100%). $^1$H NMR was consistent with the title compound.

Example 74: tert-butyl (R)-2-((S)-6-(trans-4-tert-butylcyclohexyloxy)-5-(trifluoromethyl)-1,2,3,4-tetrahydronaphthalen-2-yl)-1-(phosphonooxy)propan-2-ylcarbamate To a solution of tert-Butyl (R)-2-((S)-6-(trans-4-tert-butylcyclohexyloxy)-5-(trifluoromethyl)-1,2,3,4-tetrahydronaphthalen-2-yl)-1-(phosphonooxy-o-xylylene)propan-2-ylcarbamate (50.4 mg, 0.0000710 mol) in methanol (2.0 mL, 0.048 mol) and was added 10% palladium on carbon (1:9, palladium:carbon black, 7.6 mg, 0.0000071 mol). The mixture was stirred under hydrogen (0.4 L, 0.02 mol) for 2 h. Filtered through celite and was washed with MeOH. The concentrated residue was dissolved in $CH_2Cl_2$ and was chromatographed with MeOH/$CH_2Cl_2$ (0-50%) to give tert-butyl (R)-2-((S)-6-(trans-4-tert-butylcyclohexyloxy)-5-(trifluoromethyl)-1,2,3,4-tetrahydronaphthalen-2-yl)-1-(phosphonooxy)propan-2-ylcarbamate as a white solid (22.0 mg, 51%). $^1$H NMR was consistent with the title compound.

Example 75: (R)-2-amino-2-((S)-6-(trans-4-tert-butylcyclohexyloxy)-5-(trifluoromethyl)-1,2,3,4-tetrahydronaphthalen-2-yl)propyl dihydrogen phosphate tert-Butyl (R)-2-((S)-6-(trans-4-tert-butylcyclohexyloxy)-5-(trifluoromethyl)-1,2,3,4-tetrahydronaphthalen-2- yl)-1-(phosphonooxy)propan-2-ylcarbamate (22.0 mg, 0.0000362 mol) was dissolved in trifluoroacetic Acid (1.0 mL, 0.013 mol) and methylene chloride (1.0 mL, 0.016 mol) was added and the mixture was stirred for 1 h. Concentration and lypholyzing gave pure (R)-2-amino-2-((S)-6-(trans-4-tert-butylcyclohexyloxy)-5-(trifluoromethyl)-1,2,3,4-tetrahydronaphthalen-2-yl)propyl dihydrogen phosphate as a white solid (18.0 mg, 98%). LCMS: Rf=1.74 min 508.41 [M+1]. $^1$H NMR (400 MHz, MeOD) δ=7.25 (d, J=9.0 Hz, 1H), 7.00 (d, J=8.6 Hz, 1H), 4.23 (dd, J=4.9, 11.2 Hz, 1H), 4.18 (m, 1H), 4.03 (dd, J=4.1, 11.3 Hz, 1H), 3.22-2.82 (m, 3H), 2.77-2.64 (m, 1H), 2.15 (d, J=12.6 Hz, 2H), 2.02 (d, J=10.6 Hz, 1H), 1.87 (d, J=13.2 Hz, 2H), 1.56-1.35 (m, 2H), 1.33 (s, 3H), 1.24-1.01 (m, 2H), 0.89 (s, 9H).

Example 76: 6-bromo-2-(trans-4-tert-butylcyclohexyloxy)quinoline

The mixture of 6-bromo-quinolin-2-ol (1.00 g, 0.00446 mol), cis-4-tert-butylcyclohexanol (0.837 g, 0.00536 mol), and triphenylphosphine (1.405 g, 0.005356 mol) in toluene (9.508 mL, 0.08926 mol) was heated to reflux, and diisopropyl azodicarboxylate (1.054 mL, 0.005356 mol) was added dropwise and was stirred at reflux for 6 hours. The mixture was taken up into methylene chloride and subjected to chromatography with EtOAc/hexane (0:100 to 40:60) to give 6-bromo-2-(trans-4-tert-butylcyclohexyloxy)quinoline as a white solid (0.581 g, 36%). LCMS: Rf=2.82 min (362.38, [M]+, 100%).

Example 77: 2-Methyl-propane-2-sulfinic acid [(R)-1-[2-(4-trans-tert-butylcyclohexyloxy)-quinolin-6-yl]-2-(tert-butyl-dimethyl-silanyloxy)-1-methyl-ethyl]-amide To a solution of 6-bromo-2-(4-trans-tert-butyl-cyclohexyloxy)-quinoline (0.273 g, 0.000755 mol) in ether (1.3 mL, 0.012 mol) at −78° C. was added 2.0 M of n-butyllithium in cyclohexane (0.412 mL, 0.000823 mol) and stirred for 30 min then to 0° C. for 5 min. To a solution of (S)—N-(1-(tert-butyldimethylsilyloxy)propan-2-ylidene)-2-methylpropane-2-sulfinamide (0.200 g, 0.000686 mol) in toluene (6.8 mL, 0.064 mol) at −78° C. was added 2.0 M trimethylaluminum in toluene (0.377 mL, 0.000755 mol). The organolithium solution was transferred to the above mixture by syringe. And the mixture was stirred at −41° C. for 3 h. The reaction was quenched with Na$_2$SO$_4$ aqueous saturated solution, diluted with EtOAc, and filtrated through Celite. washed with brine, dried. The mixture was concentrated and crude NMR showed desired product as 1:0.28 diastereoisomer mixture. The mixture was taken up into methylene chloride and subjected to chromatography purification with EtOAc/hexane (0:100 to 100:0) to give 2-methyl-propane-2-sulfinic acid [(R)-1-[2-(4-tertbutyl-cyclohexyloxy)-quinolin-6-yl]-2-(tert-butyl-dimethyl-silanyloxy)-1-methyl-ethyl]-amide (3.6:1 mixture) as a white sticky solid (0.227 g, 58%). LCMS 2.77 min 575.73 ([M+1], 100%).

Example 78: 2-amino-2-(2-(trans-4-tert-butylcyclohexyloxy) quinolin-6-yl)propan-1-ol 2-Methyl-propane-2-sulfinic acid [(R)-1-[2-(4-trans-tert-butyl-cyclohexyloxy)-quinolin-6-yl]-2-(tert-butyl-dimethyl-silanyloxy)-1-methyl-ethyl]-amide (227.4 mg, 0.3955 mmol, the above mixture) in methanol (4.5 mL, 110 mmol) was added 4.0 M hydrogen chloride in 1,4-dioxane (2.2 mL, 9.0 mmol) and was stirred overnight. LC showed single peak. After removal of solvent, the residue was dissolved in methylene chloride, 1M aq. NH$_4$OH was added, and the extracted organic layer was dried. The concentrated residue was subjected to chromatography purification with MeOH/CH$_2$Cl$_2$ (20-40%) give 2-amino-2-(2-(trans-4-tert-butylcyclohexyloxy) quinolin-6-yl)propan-1-ol as a foamy solid (110 mg, 78%). LCMS: Rf=1.51 min 357.42 ([M+1]). $^1$H NMR (400 MHz, MeOD) δ=8.10 (d, J=8.8 Hz, 1H), 7.86 (s, 1H), 7.77 (d, J=1.4 Hz, 1H), 6.87 (d, J=8.8 Hz, 1H), 5.14 (tt, J=4.6, 11.0 Hz, 1H), 3.74 (d, J=11.0 Hz, 1H), 3.69 (d, J=11.0 Hz, 1H), 2.29 (d, J=12.5 Hz, 2H), 1.93 (d, J=11.4 Hz, 2H), 1.54 (s, 3H), 1.51-1.38 (m, 2H), 1.37-1.22 (m, 2H), 1.20-1.09 (m, 1H), 0.94 (s, 9H).

Example 79: (R)-2-amino-2-(2-(trans-4-tert-butylcyclohexyloxy)quinolin-6-yl)propan-1-ol and

Example 79A: (S)-2-amino-2-(2-(trans-4-tert-butylcyclohexyloxy)quinolin-6-yl)propan-1-ol SFC separation of the above 2-amino-2-[2-(4-trans-tert-butyl-cyclohexyloxy)-quinolin-6-yl]-propan-1-ol (Example 78) (100 mg, 0.3 mmol) with Whelk-01 (R,R) (3×15 cm) 08-10149 in 15% MeOH (0.1% DEA)/CO2, 100 bar, 85 mL/min, 220 nm gave 62 mg of peak 1 (>99% ee) and 12 mg of peak 2 (>99% ee). Peak 1 was subjected to chromatography purification with CH$_2$Cl$_2$/MeOH (20-50%) give (R)-2-amino-2-(2-(trans-4-tert-butylcyclohexyloxy)quinolin-6-yl)propan-1-ol as a foamy solid (39.4 mg). LCMS 1.42 min 357.30 ([M+1], 100%). $^1$H NMR (400 MHz, MeOD) δ=8.10 (d, J=8.8 Hz, 1H), 7.86 (s, 1H), 7.78 (s, 2H), 6.87 (d, J=8.8 Hz, 1H), 5.20-5.09 (m, 1H), 3.75 (d, J=11.0 Hz, 1H), 3.70 (d, J=11.0 Hz, 1H), 2.29 (d, J=8.0 Hz, 2H), 1.93 (d, J=14.5 Hz, 2H), 1.55 (s, 3H), 1.52-1.38 (m, 2H), 1.38-1.23 (m, 2H), 1.20-1.07 (m, 1H), 0.94 (s, 9H).

Peak 2 was subjected to chromatography purification with MeOH/CH$_2$Cl$_2$ (20-50%) give (S)-2-amino-2-(2-(trans-4-tert-butylcyclohexyloxy) quinolin-6-yl)propan-1-ol as a gel (2.0 mg). LCMS 1.42 min 357.30 ([M+1], 100%). $^1$H NMR (400 MHz, MeOD) δ=8.10 (d, J=8.8 Hz, 1H), 7.86 (s, 1H), 7.77 (d, J=1.4 Hz, 1H), 6.87 (d, J=8.8 Hz, 1H), 5.14 (tt, J=4.6, 11.0 Hz, 1H), 3.74 (d, J=11.0 Hz, 1H), 3.69 (d, J=11.0 Hz, 1H), 2.29 (d, J=12.5 Hz, 2H), 1.93 (d, J=11.4 Hz, 2H), 1.54 (s, 3H), 1.51-1.38 (m, 2H), 1.37-1.22 (m, 2H), 1.20-1.09 (m, 1H), 0.94 (s, 9H).

Example 80: tert-butyl (R)-2-(2-(trans-4-tert-butylcyclohexyloxy)quinolin-6-yl)-1-hydroxypropan-2-ylcarbamate (R)-2-Amino-2-[2-(4-tert-butyl-cyclohexyloxy)-quinolin-6-yl]-propan-1-ol (20.5 mg, 0.0000575 mol) in chloroform (3 mL, 0.03 mol) and saturated aqueous sodium bicarbonate solution (2 mL, 0.02 mol) and di-tert-butyldicarbonate (18.8 mg, 0.0000862 mol) was added and the mixture was stirred at rt for 24 h. After separation of organic layer, the aqueous layer was extracted with CHCl$_3$. The organic layer was washed with brine and dried over anhydrous Na$_2$SO$_4$. The concentrated residue was chromatographed with MeOH/CH$_2$Cl$_2$ (0-55%) to give tert-butyl (R)-2-(2-(trans-4-tert-butylcyclohexyloxy)quinolin-6-yl)-1-hydroxypropan-2-ylcarbamate (26.0 mg, 100%).

Example 81: {(R)-1-[2-(4-tert-Butyl-cyclohexyloxy)-quinolin-6-yl]-1-methyl-2-phosphonooxy-o-xylylene-ethyl}-carbamic acid tert-butyl ester To a solution of {(R)-1-[2-(4-tert-Butyl-cyclohexyloxy)-quinolin-6-yl]-2-hydroxy-1-methyl-ethyl}-carbamic acid tert-butyl ester (41.6 mg, 0.0000911 mol) and 1H-tetrazole (19.1 mg, 0.000273 mol) in tetrahydrofuran (0.96 mL, 0.012 mol) was added o-xylylene N,N-diethylphosphoramidite (29.5 uL, 0.000137 mol) at rt. The resulting mixture was stirred at rt for 1 d, then hydrogen peroxide (200 μL, 0.0020 mol) was added and the mixture was stirred at rt for 1 h. The reaction was quenched with satd. $NaS_2O_3$, then extracted with EtOAc, then dried over $Na_2SO_4$. The residue was chromatographed with $MeOH/CH_2Cl_2$ (0-100%) to give the title compound (38.5 mg, 98%).

Example 82: (R)-2-amino-2-(2-(trans-4-tert-butylcyclohexyloxy)quinolin-6-yl)propyl dihydrogen phosphate {(R)-1-[2-(4-tert-Butyl-cyclohexyloxy)-quinolin-6-yl]-1-methyl-2-phosphonooxy-o-xylylene-ethyl}-carbamic acid tert-butyl ester (38.5 mg, 0.0000603 mol) in methanol (1.7 mL, 0.041 mol) and was added 10% palladium on carbon (1:9, palladium:carbon black, 6.4 mg, 0.0000060 mol). The mixture was stirred under hydrogen (0.3 L, 0.01 mol) for 2 h. Filtrate through Celite and washed with MeOH. The concentrated residue (28.6 mg) was moved to next step directly. (R)-1-[2-(4-tert-Butyl-cyclohexyloxy)-quinolin-6-yl]-1-methyl-2-phosphonooxy-ethyl}-carbamic acid tert-butyl ester (28.6 mg, 0.0000533 mol) was dissolved in methylene chloride (1.0 mL, 0.016 mol) and trifluoroacetic Acid (1.0 mL, 0.013 mol) was added and the mixture was stirred for 1 h. LC give a single peak. Concentration and lyophilizing gave (R)-2-amino-2-(2-(trans-4-tert-butylcyclohexyloxy)quinolin-6-yl)propyl dihydrogen phosphate as a white solid (30 mg, 100%). LCMS: Rf=1.32 min 254 nm (437.20, [M+1]+, 100%). $^1$H NMR (400 MHz, MeOD) δ=8.17 (d, J=10.4 Hz, 1H), 7.95-7.85 (m, 2H), 7.81-7.74 (m, 1H), 6.97 (d, J=8.2 Hz, 1H), 5.23-5.11 (m, 1H), 4.33 (dd, J=4.0, 11.0 Hz, 1H), 4.20 (d, J=5.5 Hz, 1H), 2.29 (d, J=13.0 Hz, 2H), 1.93 (d, J=12.9 Hz, 2H), 1.56-1.20 (m, 4H), 1.20-1.06 (m, 1H), 0.94 (s, 9H).

Example 83: 3-acetamidophenyl acetate

3-Aminophenol (19 g 0.17 mol) was dissolved in $Ac_2O$ (162 g, 1.59 mol, 9.5 eq.), and pyridine (4.9 g, 0.062 mol, 0.36 eq.) was added. Then the reaction mixture was stirred at 80° C. over 2 h. Ice water (50 mL) was added to the mixture, and saturated $NaHCO_3$ solution was added to the mixture until pH=7, then extracted (EA), washed (brine), dried ($Na_2SO_4$), and concentrated to give 3-acetamidophenyl acetate as gray solid (30 g, yield: 93%). ESI-MS: 194 (M+H)+.

Example 84: 2-chloro-3-formylquinolin-7-yl acetate

A three-neck flask was charged with DMF (25 mL, 0.325 mol, 3 eq.), then $POCl_3$ (70 mL, 0.758 mol, 7 eq.) was added to the DMF at 0° C. The solution was stirred at 0° C. for 30 min. Then 3-acetamidophenyl acetate (20.8 g, 0.108 mol) was added to the mixture at 0° C. After 30 min the mixture was heated to 65° C. and stirred for 16 h. Then, the reaction mixture was added to ice water (300 mL) and neutralized with saturated $NaHCO_3$ to pH=6, extracted (EA), washed (brine), dried ($Na_2SO_4$), filtered and evaporated to dryness to give the crude product, which was purified by silica gel column chromatography (EA-PE, 3:1) to give desired compound as gray solid (2.67 g, yield 10%). ESI-MS: 250 (M+H)+. $^1$H NMR (300 MHz, $CDCl_3$) δ: 2.39 (s, 3H), 7.42-7.45 (m, 1H), 7.80-7.81 (d, 1H), 7.97-8.00 (d, 1H), 8.74 (s, 1H), 10.54 (s, 1H).

Example 85: 7-hydroxyquinoline-3-carbaldehyde

To a solution of 2-chloro-3-formylquinolin-7-yl acetate (2.9 g, 14 mmol) and $Pd(PPh_3)_4$ (1.6 g, 1.4 mmol, 0.1 eq.), $Et_3N$ (17 g, 168 mmol, 16 eq.) in DMF (100 mL) was added formic acid (3.48 g, 75.6 mmol, 5.4 eq.) dropwise over 5 min. The mixture was warmed to 110° C. over 2 h. Then, the reaction mixture was diluted (water), extracted (EA), washed (brine), dried ($Na_2SO_4$), filtered and evaporated to dryness to give the crude product, which was purified by silica gel column chromatography (PE-EA, 1:1) to give desired compound as yellow solid (1.45 g, yield 60%). ESI-MS: 216 (M+H)+. $^1$H NMR (300 MHz, $CDCl_3$) δ: 7.26-7.32 (m, 2H), 8.04-8.07 (d, 1H), 8.78 (d, 1H), 9.13 (s, 1H), 10.13 (s, 1H).

Example 86: 7-(heptyloxy)quinoline-3-carbaldehyde

To a solution of 7-hydroxyquinoline-3-carbaldehyde (1.3 g, 7.5 mmol) in DMF (30 mL) was added 1-bromo-heptane (5.37 g, 30 mmol, 4 eq.) and $K_2CO_3$ (2.0 g, 15 mmol, 2 eq.). The mixture was warmed to 60° C. over 3 h. Then, the reaction mixture was diluted (water), extracted (EA), washed (brine), dried ($Na_2SO_4$), filtered and evaporated to dryness to give the crude product, which was purified by silica gel column chromatography (PE-EA, 10:1) to give desired compound as yellow solid (610 mg, yield 30%). ESI-MS: 272 (M+H)+. $^1$H NMR (300 MHz, $CDCl_3$) δ: 0.90 (t, 3H), 1.252 (s, 3H), 1.32-1.48 (m, 6H), 1.50-1.54 (m, 2H), 1.84-1.91 (m, 2H), 4.15 (t, 2H), 7.27-7.29 (m, 1H), 7.454 (s, 1H), 7.828-7.851 (d, 1H), 8.506 (s, 1H), 9.286 (s, 1H), 10.17 (s, 1H).

Example 87: 1-(7-(heptyloxy)quinolin-3-yl)ethanol

To a solution of 7-(heptyloxy)quinoline-3-carbaldehyde (1.6 g, 5.9 mmol) in THF (30 mL) at 0° C. was added $CH_3MgI$ (2 g, 12 mmol, 2 eq.) dropwise over 10 min. The mixture was warmed to rt over 8 h. Then, the reaction mixture was quenched (water), extracted (EA), washed (brine), dried ($Na_2SO_4$), filtered and evaporated to dryness to give the crude product, which was purified by silica gel column chromatography (PE-EA, 1:5) to give desired compound as yellow oil (1.35 g, yield 80%). ESI-MS: 288 (M+H)+. $^1$H NMR (300 MHz, $CDCl_3$) δ: 0.90 (t, 3H), 1.32-1.41 (m, 6H), 1.43-1.49 (m, 2H), 1.56-1.58 (d, 2H), 1.78-1.85 (m, 2H), 4.02 (t, 2H), 5.02-5.07 (q, 1H), 7.14-7.17 (m, 1H), 7.36 (s, 1H), 7.60-7.63 (d, 1H), 8.01 (s, 1H), 8.72 (s, 1H).

Example 88: 1-(7-(heptyloxy)quinolin-3-yl)ethanone

To a solution of oxalyl chloride (987 mg, 7.8 mmol, 1.5 eq.) in dry $CH_2Cl_2$ (40 mL) was added slowly DMSO (1.6 g, 20.8 mmol, 4 eq.) at −78° C. under $N_2$ After 30 min, alcohol 1-(7-(heptyloxy)quinolin-3-yl)ethanol (1.5 g, 5.2 mmol) was added dropwise at −78° C. The mixture was stirred for 2 h at −78° C., and then $Et_3N$ (3.2 g, 31 mmol, 6 eq.) was added at −78° C. After 20 min, the mixture was warmed to room temperature. Then the reaction mixture was added to water (30 mL), extracted (DCM), washed (brine), dried ($Na_2SO_4$), filtered and evaporated to dryness to give the crude product, which was purified by silica gel column chromatography (PE-EA, 10:1) to give desired compound as yellow solid (1.08 g, yield 73%). ESI-MS: 286 (M+H)+. 1H NMR (300 MHz, CDCl3) δ: 0.90 (t, 3H), 1.32-1.54 (m, 10H), 1.84-1.89 (m, 3H), 2.71 (s, 3H), 4.14 (t, 2H), 7.25 (m, 1H), 7.43-7.44 (m, 1H), 7.79-7.82 (d, 1H), 8.61 (d, 1H), 9.12 (s, 1H).

Example 89: 5-(7-(heptyloxy)quinolin-3-yl)-5-methylimidazolidine-2,4-dione

A mixture of 1-(7-(heptyloxy)quinolin-3-yl)ethanone (730 mg, 2.56 mmol), EtOH (2 mL), H2O (3 mL), (NH4)2CO3 (1.47 g, 15.36 mmol, 6 eq.), and NaCN (251 mg, 5.12 mmol, 2 eq.) was stirred for 16 h at 60° C. Then, to the reaction mixture was added water (20 mL), extracted (EA), washed (brine), dried (Na2SO4), filtered and evaporated to dryness to give the crude product, which was purified by silica gel column chromatography (PE-EA, 1:2) to give desired compound as yellow solid (480 mg, yield 53%). ESI-MS: 356 (M+H)+. 1H NMR (300 MHz, CDCl3) δ: 0.81-0.83 (t, 3H), 1.25-1.32 (m, 7H), 1.42-1.46 (m, 2H), 1.75-1.82 (m, 2H), 1.91 (s, 3H), 3.99-4.03 (t, 2H), 7.14-7.17 (m, 1H), 7.36 (s, 1H), 7.60-7.64 (m, 2H), 8.21 (s, 1H), 9.03 (s, 1H).

Example 90: 2-amino-2-(7-(heptyloxy)quinolin-3-yl)propanoic acid

A mixture of 5-(7-(heptyloxy)quinolin-3-yl)-5-methylimidazolidine-2,4-dione (1 g, 2.8 mmol), EtOH (2 mL), H2O (4 mL), and NaOH (2.24 g, 56 mmol, 20 eq.) was stirred for 4 day at 110° C. Then, to the reaction mixture was added HCl (40%) to adjust to pH=5 and then the desired compound was generated as yellow solid (740 mg, yield 80%), without further purification for next step. ESI-MS: 331 (M+H)+. 1H NMR (300 MHz, CD3OD) δ: 0.81-0.83 (t, 3H), 1.06-1.09 (t, 3H), 1.18-1.33 (m, 8H), 1.41-1.45 (m, 2H), 1.75-1.78 (m, 2H), 1.96 (s, 3H), 3.48-3.53 (m, 2H), 4.04 (m, 2H), 7.18-7.24 (m, 2H), 7.79-7.81 (d, 1H), 8.39 (s, 1H), 8.89 (s, 1H).

Example 91: 2-amino-2-(7-(heptyloxy)quinolin-3-yl)propan-1-ol

To a solution of crude 2-amino-2-(7-(heptyloxy)quinolin-3-yl)propanoic acid (600 mg, 1.8 mmol) in dry THF (30 mL) was added LAH (138 mg, 3.6 mmol, 2 eq.) at 0° C. under N2. The mixture was warmed to room temperature for 3 h. Then to the reaction mixture was added water (1 mL), diluted (EA), filtered and dried (Na2SO4), evaporated to dryness to give the crude product, which was purified by prep-HPLC to give desired compound as white solid (200 mg, yield 35%). ESI-MS: 317 (M+H)+. 1H NMR (300 MHz, CDCl3) δ: 0.90 (t, 3H), 1.32-1.42 (m, 6H), 1.48-1.52 (m, 2H), 1.53 (s, 3H), 1.82-1.89 (m, 2H), 2.34 (brs, 3H), 3.66-3.69 (d, 1H), 3.81-3.84 (d, 1H), 4.08 (t, 2H), 7.11-7.14 (m, 1H), 7.26 (s, 1H), 7.57-7.59 (d, 1H), 8.10 (s, 1H), 8.83 (s, 1H). HPLC: 214 nm: 98.948%, 254 nm: 99.526%.

Example 92: (E)-1-nitro-4-(oct-1-enyl)benzene 1-bromo-4-nitrobenzene (2.01 g, 10 mmol), 1-ocetene (7.8 mL, 50 mmol), and Pd(OAc)2 (50 mg, 0.2 mmol) were stirred for 10 min under nitrogen atmosphere. Then tri-o-tolylphosphine (24 mg, 0.8 mmol) was added to the mixture and stirred for 10 min. Et3N (5.5 mL, 40 mmol) was then added to the mixture. The mixture was heated to 110° C. for 18 h. Water was added to the mixture and extracted with EtOAc. The organic layer was concentrated and purified by silica gel chromatography using PE as eluent to give compound the title compound (2.121 g, 90%). 1H NMR (300 MHz, CDCl3) δ 8.097 (d, 2H), 7.235 (d, 2H), 6.442 (s, 1H), 5.976-5.377 (m, 1H), 2.231-2.052 (m, 2H), 1.710-1.246 (m, 8H), 0.850 (t, 3H).

Example 93: 4-octylaniline

A MeOH (20 mL) solution of compound (E)-1-nitro-4-(oct-1-enyl)benzene (2.121 g, 9.0 mmol) and Pd-C (200 mg, 0.9 mmol) was stirred at r.t. for 2 h under hydrogen atmosphere. Then the mixture was filtered and the filtrate was evaporated to give product the title compound (1.586 g, 85%) as a pink liquid. 1H NMR (300 MHz, CDCl3) δ 6.962 (d, 2H), 6.636 (d, 2H), 3.487 (b, 2H), 2.484 (t, 2H), 1.581-1.467 (m, 2H), 1.291-1.166 (m, 10H), 0.874 (t, 3H).

Example 94: 6-octylbenzo[d]thiazol-2-amine 4-octylaniline (500 mg, 2.5 mmol), AcOH (4 mL), and KSCN (970 mg, 10 mmol) were stirred at r.t. for 10 min, and then a solution of bromine (0.13 mL, 2.5 mmol) in AcOH (2 mL) was added to the mixture over 20 min. The reaction mixture was stirred at r.t. for 8 h, then poured into cold water and extracted with EtOAc. The organic layer was purified by silica gel chromatography using PE/EA (3/1) to give compound the title compound (460 mg, 70%). 1H NMR (300 MHz, CDCl3) δ 7.446 (s, 1H), 7.320 (s, 1H), 7.230 (d, 1H), 2.577 (t, 2H), 1.567-1.506 (m, 2H), 1.266-1.167 (m, 10H), 0.847 (t, 3H).

Example 95: 2-bromo-6-octylbenzo[d]thiazole

To a solution of p-TsOH.H2O (108 mg, 0.57 mmol) in MeCN (2 mL) was added compound 6-octylbenzo[d]thiazol-2-amine (50 mg, 0.19 mmol). The resulting suspension was cooled to 10-15° C. and to this was added, gradually, a solution of NaNO2 (26 mg, 0.38 mmol) and KBr (56 mg, 0.48 mmol) in H2O (0.5 mL). The mixture was then stirred at r.t. for 1 h. Then the mixture was extracted with EtOAc and purified by silica gel chromatography using PE to give product the title compound (50 mg, 82%). 1H NMR (300 MHz, CDCl3) δ 7.880 (t, 1H), 7.585 (s, 1H), 7.286 (t, 1H), 2.711 (t, 2H), 1.686-1.571 (m, 2H), 1.309-1.186 (m, 10H), 0.874 (t, 3H).

Example 96: 1-(tert-butyldimethylsilyloxy)propan-2-one

To a DCM (5 mL) solution of 1-hydroxypropan-2-one (500 mg, 6.8 mmol), DMAP (41 mg, 0.34 mmol) and Et3N (1.2 mL, 8.16 mmol) was added TBSCl (1.133 g, 7.5 mmol) at 0° C. under nitrogen atmosphere. The mixture was stirred at r.t. for 2 h. Then the mixture was added water and extracted with EtOAc. The organic layer was purified by silica gel chromatography using PE/EA (10/1) to give the title compound (950 mg, 75%). EDI-MS (M+1): 189. 1H NMR (300 MHz, CDCl3) δ 4.057 (s, 2H), 2.080 (s, 3H), 0.832 (s, 9H), 0.001 (s, 6H).

Example 97: (E)-N-(1-(tert-butyldimethylsilyloxy)propan-2-ylidene)-2-methylpropane-2-sulfinamide 1-(tert-butyldimethylsilyloxy)propan-2-one (188 mg, 1.0 mmol) and Ti(OEt)4 (0.52 mL, 2.5 mmol) were dissolved in THF (5 mL). Then 2-methylpropane-2-sulfinamide (121 mg, 1.0 mmol) was added to the mixture under nitrogen atmosphere. The mixture was heated to 70° C. for 2 h. The mixture was poured into brine and filtered through a plug of Celite. The organic layer was concentrated and purified by silica gel chromatography using PE/EA (5/1) to give product the title compound (190 mg, 65%). EDI-MS (M+1): 292. $^1$H NMR (300 MHz, CDCl$_3$) δ 4.152 (s, 2H), 2.248 (s, 3H), 1.156 (s, 9H), 0.839 (s, 9H), 0.001 (s, 6H).

Example 98: N-(1-(tert-butyldimethylsilyloxy)-2-(6-octylbenzo[d]thiazol-2-yl)propan-2-yl)-2-methylpropane-2-sulfinamide A toluene (2 mL) solution of 2-bromo-6-octylbenzo[d]thiazole (167 mg, 0.515 mmol) was cooled down to −78° C., then 2.5 N n-BuLi (0.2 mL, 0.515 mmol) was added to the mixture drop wise, and the mixture was stirred at −78° C. for 30 min. The toluene (2 mL) solution of (E)-N-(1-(tert-butyldimethylsilyloxy)propan-2-ylidene)-2-methylpropane-2-sulfinamide (100 mg, 0.344 mmol) was cooled down to −78° C., then 2.0 N AlMe$_3$ (0.26 mL, 0.515 mmol) was added to the mixture drop wise, and the mixture was stirred at −78° C. for 30 min. The mixture of (E)-N-(1-(tert-butyldimethylsilyloxy)propan-2-ylidene)-2-methylpropane-2-sulfinamide was added to the mixture of the lithiated 2-bromo-6-octylbenzo[d]thiazole and stirred at −78° C. for 1 h. Then saturated NH$_4$Cl solution was added to the mixture to quench the reaction. The mixture was extracted with EtOAc and purified by silica gel chromatography using PE/EA (5/1) to give the title compound. (90 mg, 48%). EDI-MS (M+1): 539. $^1$H NMR (300 MHz, CDCl$_3$) δ 7.858 (d, 1H), 7.626 (s, 1H), 7.252 (s, 1H), 4.031 (d, 2H), 3.850 (d, 1H), 3.470 (s, 1H), 2.699 (t, 2H), 1.797 (s, 3H), 1.623 (t, 2H), 1.295-1.261 (m, 21H), 0.850 (s, 9H), 0.012 (s, 6H).

Example 99: 2-amino-2-(6-octylbenzo[d]thiazol-2-yl)propan-1-ol

A methanol (5 mL) solution of N-(1-(tert-butyldimethylsilyloxy)-2-(6-octylbenzo[d]thiazol-2-yl)propan-2-yl)-2-methylpropane-2-sulfinamide (90 mg) and 4N HCl (0.325 mL, 1.3 mmol) was stirred at r.t. for 24 h. Then the mixture was extracted with EtOAc and purified by silica gel chromatography using PE/EA (½) to give product the title compound (11 mg, 26%). EDI-MS (M+1): 321. $^1$H NMR (300 MHz, CDCl$_3$) δ 7.840 (d, 1H), 7.699 (s, 1H), 7.276 (d, 1H), 4.031 (d, 1H), 3.722 (d, 1H), 2.730 (t, 2H), 2.632 (b, 3H), 1.666 (t, 2H), 1.564 (s, 3H), 1.330-1.283 (m, 10H), 0.866 (t, 3H). HPLC: 96.9% (214 nm); 98.0% (254 nm).

Example 100: 6-bromo-2-(heptyloxy)quinoline

To a mixture of 6-bromoquinolin-2-ol (352 mg 1.57 mmol) and silver carbonate (863 mg, 3.14 mmol, 2.0 eq.) in toluene (20 mL) was added 1-iodoheptane (355 mg, 1.57 mmol, 1.0 eq.) and stirred for 3 h at 110° C. The reaction mixture was evaporated under reduced pressure to remove most of solvent, then filtered, and washed with ethyl acetate. The filtrate was concentrated to give crude the title compound. The crude product was purified by flash chromatography using PE/EA (20/1) as eluent to give product as a red oil (300 mg, 60%). ESI-MS: 323.8 (M+H)$^+$. $^1$H NMR (400 MHz, DMSO-d$_6$) δ: 7.84-7.83 (m, 2H), 7.70-7.68 (m, 2H), 6.89 (d, 1H), 4.43 (t, 2H), 1.81 (q, 2H), 1.51-1.28 (m, 8H), 0.90 (t, 3H).

Example 101: 2-(heptyloxy)-6-(1-nitroethyl)quinoline 6-bromo-2-(heptyloxy)quinoline (2.014 g, 6.27 mmol) and Pd$_2$(dba)$_3$ (172 mg, 0.188 mmol, 0.03 eq.) were dissolved in DME (5 mL) and stirred under nitrogen atmosphere for 10 min. 2-di-tert-butylphosphino-2'-methylbiphenyl (117 mg, 0.36 mmol, 0.06 eq.) was added and the mixture was stirred at r.t. for 10 min. Then nitroethane (0.9 mL, 12.54 mmol, 2.0 eq.) and cesium carbonate (2.5 g, 7.5 mmol, 1.2 eq.) were added. The mixture was stirred at 50° C. under nitrogen atmosphere for 15 h. The mixture was extracted with ethyl acetate and the organic layer was purified by silica gel column chromatography using petroleum/ethyl acetate (5/1) as eluent to give product as a slight red oil (1.5 g, 78%). ESI-MS: 317.1 (M+H)$^+$. $^1$H NMR (400 MHz, CDCl$_3$) δ 7.98 (d, 1H), 7.86 (d, 1H), 7.79 (s, 1H), 7.69 (q, 1H), 6.93 (d, 1H), 5.77-5.74 (m, 1H), 4.46 (t, 2H), 1.98 (d, 3H), 1.84-1.80 (m, 2H), 1.48-1.29 (m, 8H), 0.89 (t, 3H).

Example 102: 2-(2-(heptyloxy)quinolin-6-yl)-2-nitropropan-1-ol 2-(heptyloxy)-6-(1-nitroethyl)quinoline (1.823 g, 5.77 mol) and paraformaldehyde (346 mg, 11.54 mmol, 2.0 eq.) were dissolved in THF (10 mL). CH$_3$ONa (115 mg, 2.13 mmol, 0.37 eq.) in methanol (2 mL) was added to the solution. The mixture was stirred at 80° C. under nitrogen atmosphere for 15 h. The mixture was extracted with ethyl acetate and the organic layer was concentrated and purified by silica gel column chromatography using petroleum/ethyl acetate (5/1) as eluent to give product as a slight red oil (823 mg, 43%). ESI-MS: 347.1 (M+H)$^+$. $^1$H NMR (400 MHz, CDCl$_3$) δ 7.97 (d, 1H), 7.88 (d, 1H), 7.69 (d, 1H), 7.56 (q, 1H), 6.93 (d, 1H), 4.62 (d, 1H), 4.47 (t, 2H), 3.90 (d, 1H), 2.15 (s, 3H), 1.84-1.80 (m, 2H), 1.49-1.24 (m, 8H), 0.89 (t, 3H).

Example 103: 2-amino-2(2-(heptyloxy)quinolin-6-yl)propan-1-ol 2-(2-(heptyloxy)quinolin-6-yl)-2-nitropropan-1-ol (200 mg, 0578 mmol) was dissolved in acetic acid (5 mL). zinc (376 mg, 5.78 mmol, 10.0 eq.) was added to the mixture at 0° C. and the mixture was stirred at 20° C. for 15 h. Saturated sodium carbonate solution was added to the mixture until pH=8. Then the mixture was extracted with EtOAc and the organic layer was concentrated and purified by silica gel column chromatography using dichloromethane/methanol (10/1) as eluent to give product (50 mg, 27%) as a slight yellow solid. ESI-MS: 317.2 (M+H)$^+$. HPLC: 95.99%. $^1$H NMR (400 MHz, CD$_3$OD) δ 8.09 (d, 1H), 7.81-7.79 (m, 2H), 7.68 (q, 1H), 6.92 (d, 1H), 4.38 (t, 2H), 3.84 (d, 1H), 3.74 (d, 1H), 1.86-1.75 (m, 2H), 1.70 (s, 3H), 1.43-1.25 (m, 8H), 0.85 (t, 3H).

Example 104: 6-(Benzyloxy)-3,4-dihydronaphthalen-1(2H)-one

The mixture of 6-hydroxy-3,4-dihydro-2H-naphthalen-1-one (30.74 g, 0.1895 mol), benzyl bromide (27.0 mL, 0.227 mol) and potassium carbonate (39.3 g, 0.284 mol) in acetone (250 mL, 3.4 mol) was heated to reflux under an atmosphere of nitrogen for 3 hours. The mixture was cooled to 10° C. with an ice bath, filtered and washed with small amount of acetone. The filtrate was concentrated in rotavap. The resulting crystals were collected by filtration and washed with EtOAc-hexane then hexane to give a pale yellow solid product as the first crop. The mother liquid was concentrated in rotavapor and the residue was purified by chromatograph with EtOAc:hexane (0:100 to 20:80) to give the second crop of solid product (38.07 g, 80%). $^1$H NMR (CHLOROFORM-d) δ: 8.02 (d, J=8.6 Hz, 1H), 7.32-7.51 (m, 5H), 6.91 (dd, J=8.8, 2.3 Hz, 1H), 6.80 (s, 1H), 5.13 (s, 2H), 2.93 (t, J=6.1 Hz, 2H), 2.56-2.68 (m, 2H), 2.12 (quin, J=6.3 Hz, 2H). MS (M+1): 253.0.

Example 105: 6-(Benzyloxy)-2-bromo-3,4-dihydronaphthalen-1(2H)-one

Copper(II) bromide (43.1 g, 0.193 mol) was heated to reflux in ethyl acetate (150 mL, 1.5 mol). 6-Benzyloxy-3,4-dihydro-2H-naphthalen-1-one (24.35 g, 0.09651 mol) in chloroform (150 mL, 1.9 mol) was slowly added and the mixture was refluxed overnight. The mixture was cooled to r.t., filtered. The filtrate was decolorized with activated carbon, and filtered through Celite. The filtrate was concentrated and dried in high vacuum pump to give an oily product (32.9 g, 97%). $^1$H NMR (CHLOROFORM-d) δ: 8.08 (d, J=9.1 Hz, 1H), 7.30-7.50 (m, 5H), 6.96 (dd, J=8.8, 2.3 Hz, 1H), 6.82 (s, 1H), 5.14 (s, 2H), 4.70 (t, J=4.0 Hz, 1H), 3.29 (dt, J=11.0, 5.4 Hz, 1H), 2.87 (dt, J=16.9, 4.2 Hz, 1H), 2.36-2.59 (m, 2H). MS (M+1): 332.0

Example 106: 7-(Benzyloxy)-3-bromo-1,2-dihydronaphthalene

6-Benzyloxy-2-bromo-3,4-dihydro-2H-naphthalen-1-one (32.9 g, 0.0964 mol) was dissolved in ether (200 mL, 2 mol) and methanol (30.0 mL, 0.740 mol), cooled with ice bath to internal temperature of 3° C. Sodium tetrahydroborate (1.82 g, 0.0482 mol) was added portionwise over 15 min at 3° C.-8° C. (internal). The mixture was stirred at 2-5° C. for 1 hour. Acetic acid (2.74 mL, 0.0482 mol) was added and the mixture was quenched with water, extracted with EtOAc (100 mL), washed with water (2×), brine, dried over anhydrous sodium sulfate, filtered, and concentrated to give a crude intermediate, 6-(benzyloxy)-2-bromo-1,2,3,4-tetrahydronaphthalen-1-ol (29.5 g).

The intermediate, 6-(benzyloxy)-2-bromo-1,2,3,4-tetrahydronaphthalen-1-ol, was heated to reflux with p-toluenesulfonic acid monohydrate (0.916 g, 0.00482 mol) in toluene (300 mL, 3 mol) with a Dean-Stark tube for 1 hour, cooled to r.t., washed with saturated NaHCO$_3$, water, brine, dried over anhydrous Na$_2$SO$_4$, filtered, evaporated in rotavapor to give a crude oil. Chromatograph with EtOAc:hexane (0:100 to 10:90) gave a solid product (17.29 g, 57%). $^1$H NMR (CHLOROFORM-d) δ: 7.30-7.49 (m, 5H), 6.85-6.96 (m, 1H), 6.76 (m, 3H), 5.06 (s, 2H), 2.87-3.00 (m, 2H), 2.67-2.83 (m, 2H). MS (M+1): 316.0.

Example 107: 2-(Benzylamino)-2-(6-(benzyloxy)-3,4-dihydronaphthalen-2-yl)propane-1,3-diol 7-Benzyloxy-3-bromo-1,2-dihydro-naphthalene (21.75 g, 0.06900 mol) was azeotroped with toluene (100 mL, 0.9 mol) and dried on the high vacuum for 30 min. This was dissolved in tetrahydrofuran (200 mL, 2 mol), cooled with a dry ice-isopropanol bath under an atmosphere of nitrogen. 1.70 M tert-Butyllithium in pentane (89.3 mL, 0.152 mol) was added slowly, stirred for 10 min. Triisopropyl borate (79.1 mL, 0.345 mol) was added and the mixture was stirred for 1 hour with cooling then brought to r.t. The reaction was quenched with ice-water. The organic layer was separated and the aqueous layer was extracted with EtOAc (3×50 mL). The combined organic layers were washed with water, brine, dried over anhydrous Na$_2$SO$_4$, filtered, concentrated and dried on the high vacuum to give a crude intermediate, 6-(benzyloxy)-3,4-dihydronaphthalen-2-ylboronic acid.

The intermediate, 6-(benzyloxy)-3,4-dihydronaphthalen-2-ylboronic acid, from previous step was dissolved in ethanol (400 mL, 7 mol). 1,3-Dihydroxy-2-propanone (6.22 g, 0.0690 mol) was added followed by benzylamine (7.54 mL, 0.0690 mol). The solution turned into a yellow suspension in 1 min. The mixture was stirred at r.t. for 2 hours under an atmosphere of nitrogen. The mixture was filtered. The filtrate was concentrated and the residue was dissolved in EtOAc/MeOH (300 mL/30 mL), washed with saturated NaHCO$_3$/water (50 mL/50 mL) and the aqueous layer was extracted with EtOAc (2×50 mL). The combined organic layers were washed with water (50 mL), brine, dried with Na$_2$SO$_4$, filtered, concentrated and dried in high vacuum to give a red-brown solid product as the first crop. The collected solid was dissolved in DCM-MeOH (50 ml/50 mL) and stirred at r.t. overnight under an atmosphere of nitrogen. The solution was concentrated. The residue was treated as the first crop with EtOAc-MeOH-aqueous NaHCO$_3$ to afford the second crop of product (4.40 g, 15%). $^1$H NMR (CHLOROFORM-d) δ: 6.98-7.66 (m, 13H), 6.77 (br. s., 1H), 5.05 (br. s., 2H), 3.75-4.21 (m, 6H), 2.78 (m, 2H), 1.88-2.54 (m, 2H). MS (M+1): 416.0.

Example 108: 2-Amino-2-(6-hydroxy-1,2,3,4-tetrahydronaphthalen-2-yl)propane-1,3-diol A 1 L pressure vessel was charged 10% Pd-C, dry Engelhard (10:90, palladium:carbon black, 0.966 g, 0.000908 mol) under an atmosphere of nitrogen. The solution of 2-benzylamino-2-(6-benzyloxy-3,4-dihydro-naphthalen-2-yl)-propane-1,3-diol (23.75 g, 0.05716 mol) in ethanol (300 mL, 5 mol) and ethyl acetate (300 mL, 3 mol) was added under an atmosphere of nitrogen. The mixture was connected to a H$_2$ line, flashed with 50 psi of H$_2$ three times, then stirred under 50 psi of H$_2$ for 6 hours. The mixture was continuously stirred under 50 psi of H$_2$ overnight. Acetic acid (18.0 mL, 0.316 mol) was added and the mixture was stirred under 50 psi of H$_2$ for 30 hours. 10% Pd-C, dry Engelhard (10:90, palladium:carbon black, 1.01 g, 0.000949 mol) suspended in 10 mL of EtOAc was added and the mixture was continuously stirred under 50 psi of H$_2$ for 45 hours. The mixture was filtered through Celite, concentrated to 54 g. The material was dissolved in ethanol (300 mL, 5 mol) and acetic acid (10.0 mL, 0.176 mol). The resulted solution was added to a pressure hydrogenation flask charged with 10% Pd-C, dry Engelhard (10:90, palladium:carbon black, 2.10 g, 0.00197 mol) under an atmosphere of Nitrogen. The mixture was flashed with 50 psi of H$_2$ three times then stirred under 50 psi of H$_2$ for 3 days. Acetic acid (10.0 mL, 0.176 mol) was added and the mixture was continuously stirred under 50 psi of H$_2$ for 24 more hours. The reaction mixture was released from the H$_2$ pressure, filtered through Celite, concentrated and dried in high vacuum to give a crude product. The material was used for next step without further purification. $^1$H NMR (MeOD) δ: 6.84-6.99 (m, 1H), 6.43-6.61 (m, 2H), 3.62-3.88 (m, 4H), 2.55-2.94 (m, 4H), 2.17-2.35 (m, 1H), 1.91-2.11 (m, 1H), 1.68-1.82 (m, 1H). MS (M+1): 238.0.

Example 109: tert-Butyl 1,3-dihydroxy-2-(6-hydroxy-1,2,3,4-tetrahydronaphthalen-2-yl)propan-2-ylcarbamate 2-Amino-2-(6-hydroxy-1,2,3,4-tetrahydro-naphthalen-2-yl)-propane-1,3-diol (27.2 g, 0.0573 mol) was dissolved in tetrahydrofuran (180 mL, 2.2 mol) and water (250 mL, 14 mol). To the solution was added portionwise sodium bicarbonate (48.1 g, 0.573 mol) (pH~8). The solution was cooled with an ice bath. Di-tert-butyldicarbonate (25.0 g, 0.115 mol) was added and the mixture was brought to r.t. overnight. Di-tert-butyldicarbonate (5.00 g, 0.0229 mol) was added and the mixture was stirred for 24 hours. The mixture was extracted with EtOAc (2×100 mL), brine (2×), dried over anhydrous sodium sulfate, filtered, concentrated in rotavapor to give a dark brown oily residue. $Et_2O$ (150 mL) was added. The resulted solid was collected by filtration and washed with $Et_2O$, dried in air. The filtrate was concentrated in rotavapor and subject to chromatography purification with DCM:MeOH (100:0 to 96:4) to give a solid product (1.03 g, 5%). $^1$H NMR (MeOD) δ: 6.76-6.95 (m, 1H), 6.40-6.62 (m, 2H), 3.64-3.92 (m, 4H), 2.53-2.89 (m, 4H), 2.16-2.40 (m, 1H), 1.84-2.11 (m, 2H), 1.45 (s, 9H). MS (M+1): 338.0.

Example 110: tert-Butyl 5-(6-hydroxy-1,2,3,4-tetrahydronaphthalen-2-yl)-2,2-dimethyl-1,3-dioxan-5-ylcarbamate tert-Butyl 1,3-dihydroxy-2-(6-hydroxy-1,2,3,4-tetrahydronaphthalen-2-yl)propan-2-ylcarbamate (0.400 g, 0.00118 mol) was treated with 2,2-dimethoxypropane (20.0 mL, 0.163 mol) and p-toluenesulfonic acid monohydrate (0.0226 g, 0.000118 mol) in ethyl acetate (20.0 mL, 0.205 molat r.t. for 24 hours. The solvent was removed. 2,2-dimethoxypropane (20.0 mL, 0.163 mol) was added, followed by boron trifluoride etherate (0.150 mL, 0.00118 mol). The mixture was stirred at r.t. overnight. The mixture was quenched with saturated $NaHCO_3$ aqueous solution, extracted with EtOAc, washed with brine, dried over $Na_2SO_4$, filtered, and concentrated to give a crude. Chromatograph with DCM:MeOH (100:0 to 93:7) gave a solid product (560 mg, 100%). $^1$H NMR (CHLOROFORM-d) δ: 6.89-6.99 (m, 1H), 6.49-6.65 (m, 2H), 6.46-6.47 (s, br, 1H), 3.99 (m, 4H), 3.13-3.30 (m, 4H), 2.69-2.85 (m, 2H), 2.10-2.39 (m, 1H), 1.56 (s, 6H), 1.37-1.50 (s, br, 9H). MS (M+Na+): 400.0.

Example 111: 6-(5-(tert-Butoxycarbonylamino)-2,2-dimethyl-1,3-dioxan-5-yl)-5,6,7,8-tetrahydronaphthalen-2-yl trifluoromethanesulfonate

[5-(6-Hydroxy-1,2,3,4-tetrahydro-naphthalen-2-yl)-2,2-dimethyl-1,3-dioxinan-5-yl]-carbamic acid tert-butyl ester (0.560 g, 0.00119 mol) was dissolved in methylene chloride (20 mL, 0.3 mol). N,N-Diisopropylethylamine (0.620 mL, 0.00356 mol) was added followed by N-phenylbis(trifluoromethanesulphonimide) (0.594 g, 0.00166 mol). The solution was stirred at r.t. for 22 hours. The mixture was concentrated to ~5 mL, chromatographed with EtOA:hexane (0:100 to 40:60) and a solid product was obtained (313 mg, 52%). $^1$H NMR (CHLOROFORM-d) δ: 7.11 (m, 1H), 6.95 (m, 2H), 4.81 (s, br, 1H), 3.95 (m, 4H), 3.20 (m, 1H), 2.86 (m, 3H), 2.67 (m, 1H), 2.50 (m, 1H), 2.02 (m, 1H), 1.43 (m, 15H). MS (M+1): 510.0.

Example 112: tert-Butyl 5-(6-(3-(benzyloxy)phenylthio)-1,2,3,4-tetrahydronaphthalen-2-yl)-2,2-dimethyl-1,3-dioxan-5-ylcarbamate Trifluoromethanesulfonic acid 6-(5-tert-butoxycarbonylamino-2,2-dimethyl-1,3-dioxinan-5-yl)-5,6,7,8-tetrahydro-naphthalen-2-yl ester (0.310 g, 0.000608 mol), 3-benzyloxy-benzenethiol (0.145 g, 0.000669 mol), tris(dibenzylideneacetone)-dipalladium(0) (0.0167 g, 0.0000182 mol) and xantphos (0.0211 g, 0.0000365 mol) were dissolved in 1,4-dioxane (10 mL, 0.1 mol). The solution was degassed by applying low vacuum and backfilling with $N_2$ for 5 times. The pre-degassed N,N-diisopropylethylamine (0.350 mL, 0.00201 mol) in the same way was added. The mixture was heated to reflux under an atmosphere of nitrogen for 14 hours then cooled to r.t. tris(dibenzylideneacetone)dipalladium(0) (0.0501 g, 0.0000548 mol) and xantphos (0.0634 g, 0.000110 mol) was added. The mixture was degassed three times, heated to reflux for 6 more hours, cooled to r.t. The mixture was filtered, and concentrated to give a crude residue. Chromatography with EtOAc-hexane (0:100 to 20:80) two times gave a solid product (243 mg, 43%). $^1$H NMR (CHLOROFORM-d) δ: 7.31-7.44 (m, 5H), 7.18-7.23 (m, 1H), 7.17 (d, J=2.0 Hz, 2H), 7.04-7.09 (m, 1H), 6.97-7.04 (m, 1H), 6.84-6.92 (m, 1H), 6.79-6.84 (m, 1H), 5.02 (s, 2H), 4.86 (s, br, 1H), 3.95-4.05 (m, 4H), 2.77-2.97 (m, 4H), 2.64-2.76 (m, 1H), 2.47-2.60 (m, 1H), 2.00-2.14 (m, 1H), 1.51-1.60 (m, 6H), 1.41-1.51 (m, 9H). MS (M+Na+): 598.0.

Example 113: 2-Amino-2-(6-(3-(benzyloxy)phenylthio)-1,2,3,4-tetrahydronaphthalen-2-yl)propane-1,3-diol tert-Butyl 5-(6-(3-(benzyloxy)phenylthio)-1,2,3,4-tetrahydronaphthalen-2-yl)-2,2-dimethyl-1,3-dioxan-5-ylcarbamate (0.240 g, 0.000292 mol) was treated with 6.0 M hydrogen chloride in water (10 mL, 0.06 mol) in methanol (20 mL, 0.5 mol) at r.t. for 17 hours, To the mixture was added ~2 mL of EtOAc and the mixture was continuously stirred at r.t. for 48 hours. The solution was concentrated to dryness and dissolved in methanol, purified by HPLC on a Gilson system. The pure fractions were combined, concentrated and lyophilized for 3 days to give a white powder product as TFA salt (0.100 g, yield 54.5%). $^1$H NMR (MeOD) δ: 7.15-7.30 (m, 5H), 7.04-7.11 (m, 1H), 6.99 (m, 3H), 6.65-6.76 (m, 3H), 4.90 (s, 2H), 3.65 (d, J=2.0 Hz, 4H), 2.62-2.83 (m, 4H), 2.13-2.27 (m, 1H), 1.88-1.98 (m, 1H), 1.37-1.53 (m, 1H). MS (M+1): 436.0.

Example 114: Sphingosine Kinase Assay

To assay a test compound for its properties as a substrate of sphingosine kinase 2 (SK2), an assay using recombinantly expressed SK2 was used. Briefly, HEK293E cells were transiently transfected with plasmids containing DNA encoding a sphingosine kinase 2 (SK2) (canine, mouse, or human). The cells were cultured in Dulbecco's Minimal Essential Medium (DMEM) containing 0.25 mg/mL G418, 10% fetal calf serum (FCS), and 10 mL/L amphotericin/streptomycin for 48 hours, then harvested, washed three times in phosphate buffered saline (PBS) and lysed by incubation in lysis buffer (20 mM Tris pH 7.4, 20% glycerol, 1 mM β-mercaptoethanol, 1 mM EDTA, 1 mM Na orthovanadate, 40 mM β-glycerophosphate, 15 mM NaF, 10 mg/mL, leupeptin, 10 mg/mL soybean trypsin inhibitor, 1 mM PMSF, 0.5 mM 4-deoxyperidoxone, 200 mM KCl, 10 mM $MgCl_2$, for about 30 minutes on ice. The lysate was centrifuged at 15,000 rpm for 18 minutes and the cell debris was discarded. The soluble fraction was used in the sphingosine kinase reaction. Examples of SPHK2 concentrations in the resulting lysates were 8.12 µg/µL (in a canine SPHK2 preparation) and 8.47 µg/µL (in a human SPHK2 preparation).

The SK2 kinase assay was performed in a 200 µL reaction mixture containing 20 µm sphingosine (control) or 20 µM test compound (prepared as a 200 μM stock solution containing 0.1% fatty acid-free bovine serum albumin (BSA)), 38 μL lysate, and 2 μM ATP (freshly prepared). Kinase reactions were incubated at 37° C. for 70 minutes followed by detection of phosphorylated compound (control or test compound) using UV absorbance at 282 nm. To further analyze the test compound from this reaction, test compound kinase reactions were mixed with an equal volume of acidic acetonitrile and shaken for 10 minutes. The protein precipitate was spun down. The supernatant was analyzed on HPLC using a C18 column. The parent and phosphorylated test compound were quantitated using area under the curve (AUC) calculation. Test compounds that are phosphorylated in this assay are candidate compounds for use as S1P modulators.

Example 115: Lymphopenia Assay

Measurement of circulating lymphocytes: Compounds were dissolved in 30% HPCD. Mice (C57bl/6 male, 6-10 week-old) were administered 0.5 and 5 mg/kg of a compound via oral gavage. 30% HPCD was included as a negative control.

Blood was collected from the retro-orbital sinus 5 and 24 hours after drug administration under short isoflurane anesthesia. Whole blood samples were subjected to hematology analysis. Peripheral lymphocyte counts were determined using an automated analyzer (HEMAVET™ 3700). Three mice were used to assess the lymphocyte depletion activity of each compound screened.

Compounds of formula (I) induced full lymphopenia at times as short as 3 hours or less to as long as 48 hours or more; for example, 4 to 36 hours, or 5 to 24 hours. In some cases, a compound of formula induced full lymphopenia at 5 hours and partial lymphopenia at 24 hours. The dosage required to induce lymphopenia can be in the range of, e.g., 0.001 mg/kg to 100 mg/kg; or 0.01 mg/kg to 10 mg/kg. The dosage can be 10 mg/kg or less, such as 5 mg/kg or less, 1 mg/kg or less, or 0.1 mg/kg or less.

| Example # | Lymphopenia ($ED_{50}$ mg/kg) |
|---|---|
| 18 | 0.5-5 mg/kg |
| 21 | <0.5 mg/kg |
| 23 | <0.5 mg/kg |
| 24 | >5 mg/kg |
| 26 | <0.5 mg/kg |
| 27 | >5 mg/kg |
| 38 | 0.5-5 mg/kg |
| 50 | 0.5-5 mg/kg |
| 61 | 0.5-5 mg/kg |
| 71 | <0.5 mg/kg |
| 71A | >5 mg/kg |
| 78 | >5 mg/kg |
| 79 | >5 mg/kg |
| 79A | >5 mg/kg |
| 91 | 0.5-5 mg/kg |
| 99 | >5 mg/kg |
| 103 | 0.5-5 mg/kg |
| 113 | <0.5 mg/kg |

These results demonstrated compounds of the invention can induce lymphopenia.

Example 116: Calcium Mobilization

Compounds that were not specific for the $S1P_1$ receptor, can have activity for other SIP receptor subtypes, e.g., $S1P_2$, $S1P_3$, $S1P_4$, or $S1P_5$, and can cause undesirable side effects. Accordingly, compounds were tested to identify those that were specific for $S1P_1$ activity and had little or no activity, or are antagonists of, $S1P_3$ activity. Accordingly, the test compounds were tested in a calcium mobilization assay to determine agonist activity at either the human $S1P_1$ or human $S1P_3$ receptor, and antagonist activity only at the human $S1P_3$ receptor. The procedure was essentially as described (with modifications described below) in Davis et al. (2005) Journal of Biological Chemistry, vol. 280, pp. 9833-9841, which is incorporated by reference in its entirety. Calcium mobilization assays were performed in recombinant CHEM cells expressing human $S1P_1$ or $S1P_3$ purchased from Millipore (Billerica, Mass.). To detect free intracellular calcium, $S1P_1$ or $S1P_3$ cells were loaded with FLIPR Calcium 4 dye from Molecular Devices (Sunnyvale, Calif.). Cells were imagined for calcium mobilization using a FLIPR$^{TETRA}$ equipped with a 96-well dispense head.

Figure 11:
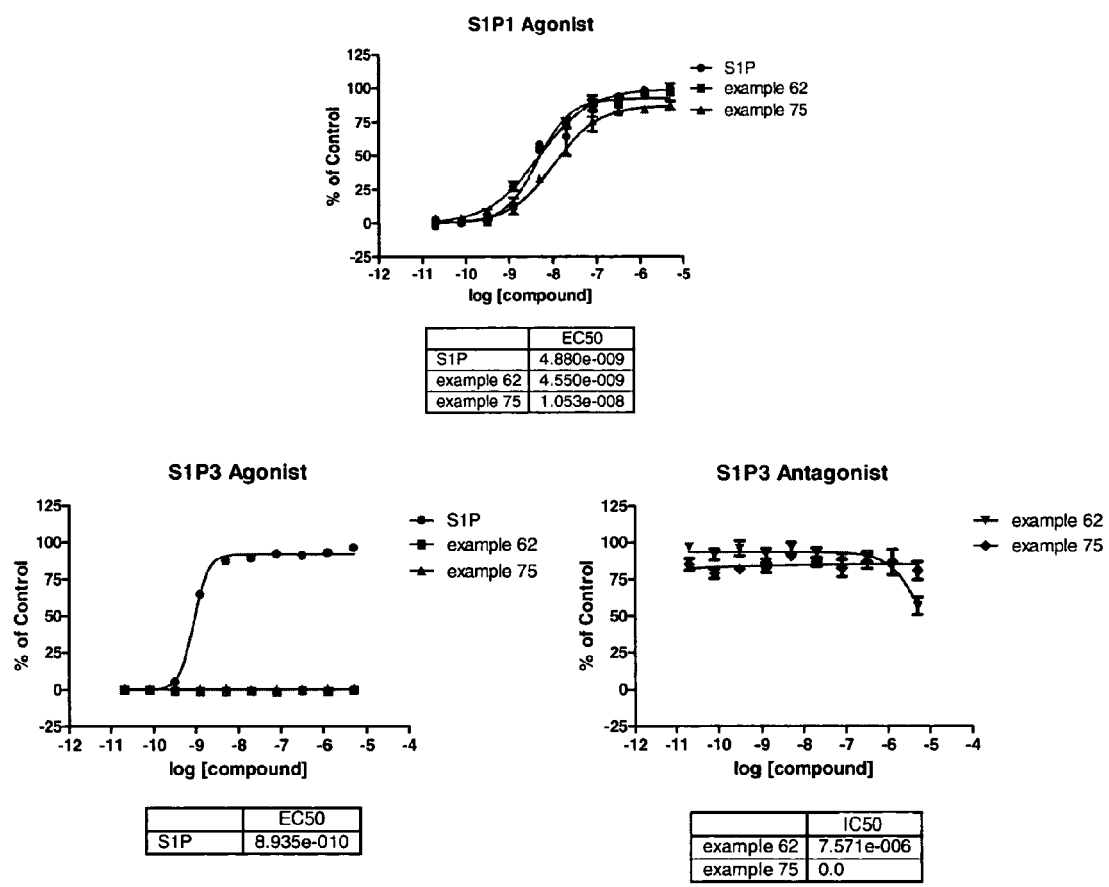
FIG. 11 is a graph depicting the results of various assays on compounds of formula (I).

The data of FIG. 8 show that compounds 21 and 61A are agonists of the $S1P_1$ receptor, with potencies similar to S1P. The data of FIG. 9 show that compound 21 has weak micromolar partial $S1P_3$ agonist activity, whereas no activity was seen for compound 2. S1P was a full $S1P_3$ agonist in this assay. The data of FIG. 10 show that compounds 21 and 61A do not antagonize the $S1P_3$ receptor. The data of FIG. 11 show that compounds 263 and 269 were $S1P_1$ agonists, were not $S1P_3$ agonists, but instead were $S1P_3$ antagonists.

Example 117: In Vivo Blood Lymphocyte Depletion

Compounds useful for treating $S1P_1$-related diseases, such as certain autoimmune diseases, are generally able to sustain lymphopenia, e.g., for at least one day, at least two days, at least three days, or at least one week, or longer. To further characterize the activity of a test compound, a test compound of formula I or the vehicle was administered orally by gavage to rats. Tail blood for hematological monitoring was obtained on day-1 to give the baseline individual values, and at 2, 6, 24, 48 and 72 hours after drug application.

Example 118: In Vivo Screening Assays

Measurement of circulating lymphocytes: Compounds were dissolved in DMSO and further diluted with deionized water. Mice (C57bl/6 male, 6-10 week-old) were administered 20 μg of a compound (diluted in 200 μL water, 4% DMSO) via intra-peritoneal (IP) injection under short isoflurane anesthesia. 200 μL water, 4% DMSO, and a known S1P agonist were included as negative controls.

Blood was collected from the retro-orbital sinus 18 hours after drug administration under short isoflurane anesthesia. Whole blood samples were subjected to hematology analysis. Peripheral lymphocyte counts were determined using an automated analyzer (HEMAVET™ 3700). Subpopulations of peripheral blood lymphocytes were stained by fluorochrome-conjugated specific antibodies and analyzed using a fluorescent activating cell sorter (FACSCALIBUR™). Two mice were used to assess the lymphocyte depletion activity of each compound screened. This assay indicated that compounds of the invention can suppress the level of circulating lymphocytes.

Example 119: Assessment of Heart Effect

One reported undesirable effect of an S1P agonist can be, e.g., bradycardia. Assays were conducted to determine the effect of test compounds on heart function. The effects of compounds on cardiac function were monitored using the AnonyMOUSE ECG recording system. ECGs were recorded in conscious mice (C57bl/6 male, 6-10 week-old) before and after compound administration. 90 μg of compound further diluted in 200 μL water and 15% DMSO were injected IP. Four mice were used to assess heart rate effect of each compound. Compounds were found to have little or no effect on heart rate at therapeutic levels.

The abbreviations used herein have their conventional meaning within the clinical, chemical, and biological arts. In the case of any inconsistencies, the present disclosure, including any definitions therein will prevail.

The disclosures of each and every patent, patent application, and publication cited herein are expressly incorporated herein by reference in their entirety into this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure and the claims shown below are not limited to the illustrative embodiments set forth herein.

What is claimed is:
1. A compound of formula (I):

or a pharmaceutically acceptable salt thereof, wherein:
 $A^1$ is —C($X^1$)=;
 $A^2$ is —C($X^2$)=;
 $A^3$ is —C($X^3$)($X^{3'}$)—;
 $A^4$ is C($X^4$)($X^{4'}$)—;
 $A^5$ is C($X^5$)($X^{5'}$)—;
 $A^6$ is —C($X^6$)=;
 $X^1$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;
 $X^2$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;
 $X^3$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;
 $X^{3'}$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;
 $X^4$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;
 $X^{4'}$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;
 $X^5$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;
 $X^{5'}$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;
 $X^6$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;
 Y is —OR$^f$, —(CR$^f$R$^g$)OR$^f$, —(CR$^f$R$^g$)$_2$OR$^f$, —O—P(O)(OR$^f$)OR$^g$, —OC(O)R$^c$, —C(O)OR$^c$, —(CR$^f$R$^g$)—P(O)(OR$^f$)OR$^g$, —(C(OH)R$^f$)—P(O)(OR$^f$)OR$^g$, —S—P(O)(OR$^f$)OR$^g$, tetrazole, —SO$_2$NHR$^f$, —SO$_3$, —CONHR$^f$, —Si(OH)$_2$, or —B(OH)$_2$;
 W is —CR$^f$R$^g$—, —NR$^f$—, —O—, —S—, —SO—, or —SO$_2$—;
 Cy is cycloalkyl, cycloalkenyl, heterocyclyl, aryl, or heteroaryl; wherein Cy is optionally substituted by 1-6 substituents selected from the group consisting of hydrogen, halo, hydroxy, nitro, cyano, —NR$^f$R$^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, haloalkoxy, cycloalkylalkoxy, cycloalkenylalkoxy, heterocyclylalkoxy, aryloxy, arylalkoxy, heteroaryloxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, and heteroaryl;
 $L^1$ is —CH$_2$—, —CHF—, or —CF$_2$—;
 $Z^4$ is hydrogen, halo, alkyl, haloalkyl, alkenyl, haloalkenyl, alkynyl, or —OR$^f$;
 or $Z^4$ is —CH$_2$— bound to the carbon atom to which Y is bound;
 or $L^1$, $Z^4$, Y, and the atoms to which they are bound form a 4-7 membered cycloalkyl group or a 4-7 membered heterocyclyl group having 1 or 2 heteroatoms selected from O and N;
 R$^a$ is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

R$^b$ is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

or R$^b$ and Z$^4$ are taken to together to form —C(O)O— or =C(R$^f$)O—;

R$^c$ is alkyl, aryl, trifluoromethyl, methylsulfonyl, trifluoromethylsulfonyl, p-tolylsulfonyl, or a group selected such that —OCOR$^c$ is a good leaving group;

each R$^f$, independently, is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

each R$^g$, independently, is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

wherein the aryl is a monocyclic, bicyclic, or tricyclic carbocyclic ring system having one or two aromatic rings; the heteroaryl is an optionally substituted mono- or bicyclic cyclic ring system containing one, two, or three heteroatoms, wherein the heteroatoms are independently selected from oxygen, sulfur, and nitrogen; and the heterocyclyl is an optionally substituted mono- or bicyclic carbocyclic ring system containing one, two, three, or four heteroatoms, wherein the heteroatoms are independently selected from oxygen, sulfur, and nitrogen.

2. The compound of claim 1, or a pharmaceutically acceptable salt thereof, wherein W is —O—.

3. The compound of claim 1, or a pharmaceutically acceptable salt thereof, wherein R$^a$ and R$^b$, independently, are each H or alkyl.

4. The compound of claim 1, or a pharmaceutically acceptable salt thereof, wherein Y is —OR$^f$.

5. The compound of claim 1, or a pharmaceutically acceptable salt thereof, wherein Y is —OH or —O—P(O)(OR$^f$)OR$^g$.

6. The compound of claim 1, or a pharmaceutically acceptable salt thereof, wherein X$^6$ is H, halo, alkyl, cycloalkyl, or haloalkyl.

7. The compound of claim 1, or a pharmaceutically acceptable salt thereof, wherein A$^3$ is —C(X$^3$)H—, A$^4$ is —C(X$^4$)H—, and A$^5$ is —C(X$^5$)H—.

8. The compound of claim 1, or a pharmaceutically acceptable salt thereof, wherein Cy has the formula:

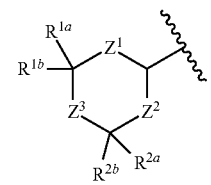

wherein

Z$^1$ is a bond, —[C(R$^d$R$^e$)]$_x$—, —CR$^d$=CR$^e$—, —O—, —NR$^f$—;

Z$^2$ is a bond, —[C(R$^d$R$^e$)]$_y$—, —CR$^d$=CR$^e$—, —O—, —NR$^f$—;

Z$^3$ is a bond, —[C(R$^d$R$^e$)]$_z$—, —CR$^d$=CR$^e$—, —O—, —NR$^f$—;

each of x, y, and z, independently, is 1 to 3;

each R$^d$, independently, is H, halo, hydroxy, alkyl, haloalkyl, alkenyl, alkoxy, cycloalkyl, —C(O)NR$^f$R$^g$, —NR$^f$R$^g$, —NR$^f$C(O)R$^g$, or —SO$_2$NR$^f$R$^g$;

each R$^e$, independently, is H, halo, hydroxy, alkyl, haloalkyl, alkenyl, alkoxy, or cycloalkyl, —C(O)NR$^f$R$^g$, —NR$^f$R$^g$, —NR$^f$C(O)R$^g$, or —SO$_2$NR$^f$R$^g$;

R$^{1a}$ and R$^{1b}$, independently, are hydrogen, halo, hydroxy, nitro, cyano, —NR$^f$R$^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl;

or R$^{1a}$ and R$^{1b}$, when taken together, are C$_2$-C$_5$ alkylene optionally terminated by or interrupted by 1 or 2 oxygen atoms, or C$_2$-C$_5$ alkenylene optionally terminated by or interrupted by 1 or 2 oxygen atoms;

R$^{2a}$ and R$^{2b}$, independently, are hydrogen, halo, hydroxy, nitro, cyano, —NR$^f$R$^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl;

or R$^{1a}$ and R$^{2a}$, when taken together, are C$_1$-C$_5$ alkylene optionally terminated by or interrupted by 1 or 2 oxygen atoms, or C$_2$-C$_5$ alkenylene optionally terminated by or interrupted by 1 or 2 oxygen atoms;

wherein R$^{1a}$, R$^{1b}$, R$^{2a}$, and R$^{2b}$ are each, independently, substituted with 0-5 substituents selected from halo, hydroxy, nitro, cyano, —NR$^f$R$^g$, or —CO$_2$R$^f$.

9. The compound of claim 8, or a pharmaceutically acceptable salt thereof, wherein R$^{1a}$ and R$^{2a}$ are both hydrogen.

10. The compound of claim 8, or a pharmaceutically acceptable salt thereof, wherein Z$^1$ is —CH$_2$CH$_2$—.

11. The compound of claim 10, or a pharmaceutically acceptable salt thereof, wherein Z$^2$ is —CH$_2$—.

12. The compound of claim 11, or a pharmaceutically acceptable salt thereof, wherein $Z^3$ is a bond.

13. The compound of claim 8, or a pharmaceutically acceptable salt thereof, wherein $R^{1b}$ is fluoro, chloro, bromo, iodo, methyl, difluoromethyl, triflurormethyl, ethyl, 1,1-difluoroethyl, propyl, isopropyl, n-butyl, i-butyl, t-butyl, n-pentyl, isopentyl, 1,1-dimethylpropyl, neopentyl, cyclopentyl, n-hexyl, cyclohexyl, methoxy, trifluoromethoxy, ethoxy, n-propoxy, i-propoxy, n-butoxy, i-butoxy, t-butoxy, n-pentyloxy, i-pentyloxy, 1,1-dimethylpropoxy, neopentyloxy, cyclopentyloxy, n-hexyloxy, or cyclohexyloxy.

14. A compound of formula (II):

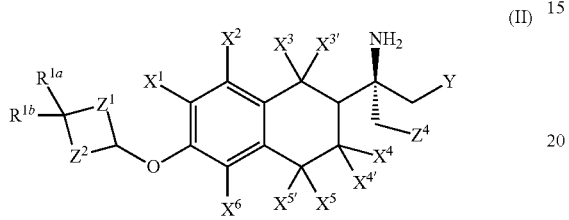

(II)

or a pharmaceutically acceptable salt thereof, wherein:

$X^1$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

$X^2$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

$X^3$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

$X^{3'}$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

$X^4$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

$X^{4'}$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

$X^5$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

$X^{5'}$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

$X^6$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

Y is —OR$^f$, —(CR$^f$R$^g$)OR$^f$, —(CR$^f$R$^g$)$_2$OR$^f$, —O—P(O)(OR$^f$)OR$^g$, —OC(O)OR$^c$, —C(O)OR$^c$, —(CR$^f$R$^g$)—P(O)(OR$^f$)OR$^g$, —(C(OH)R$^f$)—P(O)(OR$^f$)OR$^g$, —S—P(O)(OR$^f$)OR$^g$, tetrazole, —SO$_2$NHR$^f$, —SO$_3$, —CONHR$^f$, —Si(OH)$_2$, or —B(OH)$_2$;

$Z^4$ is hydrogen, halo, alkyl, haloalkyl, alkenyl, haloalkenyl, alkynyl, or —OR$^f$;

or $Z^4$ is —CH$_2$— bound to the carbon atom to which Y is bound;

or $Z^4$, Y, and the atoms to which they are bound form a 4-7 membered cycloalkyl group or a 4-7 membered heterocyclyl group having 1 or 2 heteroatoms selected from 0 and N;

$R^c$ is alkyl, aryl, trifluoromethyl, methylsulfonyl, trifluoromethylsulfonyl, p-tolylsulfonyl, or a group selected such that —OCOR$^c$ is a good leaving group;

each R$^f$, independently, is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

each R$^g$, independently, is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

$R^{1a}$ and $R^{1b}$, independently, are hydrogen, halo, hydroxy, nitro, cyano, —NR$^f$R$^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl;

or $R^{1a}$ and $R^{1b}$, when taken together, are C$_2$-C$_5$ alkylene optionally terminated by or interrupted by 1 or 2 oxygen atoms, or C$_2$-C$_5$ alkenylene optionally terminated by or interrupted by 1 or 2 oxygen atoms;

$Z^1$ is a bond, —[C(R$^d$R$^e$)]$_x$, or —CR$^d$=CR$^e$—;

$Z^2$ is a bond, —[C(R$^d$R$^e$)]$_x$, or —CR$^d$=CR$^e$—;

each of x and y, independently is 1 to 3;

each $R^d$, independently, is H, halo, hydroxyl, alkyl, alkenyl, alkoxy, or cycloalkyl;

each $R^e$, independently, is H, halo, hydroxyl, alkyl, alkenyl, alkoxy, or cycloalkyl;

wherein the aryl is a monocyclic, bicyclic, or tricyclic carbocyclic ring system having one or two aromatic rings; the heteroaryl is an optionally substituted mono- or bicyclic cyclic ring system containing one, two, or three heteroatoms, wherein the heteroatoms are independently selected from oxygen, sulfur, and nitrogen; and the heterocyclyl is an optionally substituted mono- or bicyclic carbocyclic ring system containing one, two, three, or four heteroatoms, wherein the heteroatoms are independently selected from oxygen, sulfur, and nitrogen.

15. The compound of claim 14, wherein Y is $-OR^f$.

16. The compound of claim 15, wherein Y is $-OH$ or $-O-P(O)(OR^f)OR^g$.

17. The compound of claim 14, wherein $X^6$ is H, halo, alkyl, cycloalkyl, or haloalkyl.

18. The compound of claim 14, wherein $Z^1$ is $-CH_2CH_2-$.

19. The compound of claim 18, wherein $Z^2$ is $-CH_2CH_2-$.

20. The compound of claim 19, wherein $R^{1a}$ is hydrogen, halo, hydroxy, alkyl, haloalkyl, cycloalkyl, cycloalkylalkyl, arylalkyl, alkoxy, cycloalkylalkoxy, arylalkoxy, or aryl.

21. The compound of claim 14, wherein Y is $-OH$ or $-O-P(O)(OR^f)OR^g$; $Z^4$ is H or $-OH$; $X^1$, $X^2$, $X^3$, $X^4$, and $X^5$ are each H; $X^{3'}$, $X^{4'}$, and $X^{5'}$ are each H; and $X^6$ is H, halo, alkyl, cycloalkyl, or haloalkyl.

22. The compound of claim 14, wherein $Z^1$ is $-(CH_2)_x-$ and $Z^2$ is $-(CH_2)_y-$.

23. The compound of claim 22, wherein $R^{1a}$ is alkyl, haloalkyl, cycloalkyl, aryl, or arylalkoxy.

24. The compound of claim 14, having the formula:

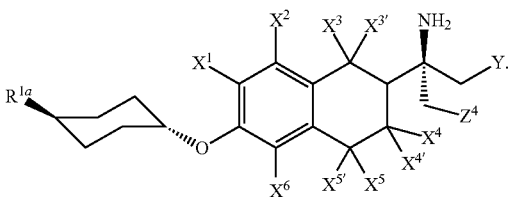

or a pharmaceutically acceptable salt thereof.

25. A pharmaceutical composition comprising a pharmaceutically acceptable carrier and a compound of formula (I):

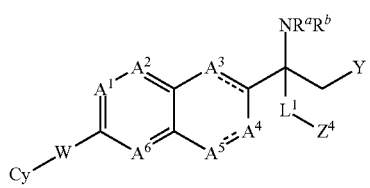

(I)

or a pharmaceutically acceptable salt thereof, wherein:
$A^1$ is $-C(X^1)=$;
$A^2$ is $-C(X^2)=$;
$A^3$ is $-C(X^3)(X^{3'})-$;
$A^4$ is $C(X^4)(X^{4'})-$;
$A^5$ is $C(X^5)(X^{5'})-$;
$A^6$ is $-C(X^6)=$;

$X^1$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, $-NR^fR^g$, $-N(R^f)SO_2R^g$, $-SO_2R^f$, $-SO_2NR^fR^g$, $-CO_2R^f$, trialkylamino, aryl, or heteroaryl;

$X^2$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, $-NR^fR^g$, $-N(R^f)SO_2R^g$, $-SO_2R^f$, $-SO_2NR^fR^g$, $-CO_2R^f$, trialkylamino, aryl, or heteroaryl;

$X^3$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, $-NR^fR^g$, $-N(R^f)SO_2R^g$, $-SO_2R^f$, $-SO_2NR^fR^g$, $-CO_2R^f$, trialkylamino, aryl, or heteroaryl;

$X^{3'}$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, $-NR^fR^g$, $-N(R^f)SO_2R^g$, $-SO_2R^f$, $-SO_2NR^fR^g$, $-CO_2R^f$, trialkylamino, aryl, or heteroaryl;

$X^4$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, $-NR^fR^g$, $-N(R^f)SO_2R^g$, $-SO_2R^f$, $-SO_2NR^fR^g$, $-CO_2R^f$, trialkylamino, aryl, or heteroaryl;

$X^{4'}$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, $-NR^fR^g$, $-N(R^f)SO_2R^g$, $-SO_2R^f$, $-SO_2NR^fR^g$, $-CO_2R^f$, trialkylamino, aryl, or heteroaryl;

$X^5$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, $-NR^fR^g$, $-N(R^f)SO_2R^g$, $-SO_2R^f$, $-SO_2NR^fR^g$, $-CO_2R^f$, trialkylamino, aryl, or heteroaryl;

$X^{5'}$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, $-NR^fR^g$, $-N(R^f)SO_2R^g$, $-SO_2R^f$, $-SO_2NR^fR^g$, $-CO_2R^f$, trialkylamino, aryl, or heteroaryl;

$X^6$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, $-NR^fR^g$, $-N(R^f)SO_2R^g$, $-SO_2R^f$, $-SO_2NR^fR^g$, $-CO_2R^f$, trialkylamino, aryl, or heteroaryl;

Y is $-OR^f$, $-(CR^fR^g)OR^f$, $-(CR^fR^g)_2OR^f$, $-O-P(O)(OR^f)OR^g$, $-OC(O)OR^c$, $-C(O)OR^c$, $-(CR^fR^g)-P(O)(OR^f)OR^g$, $-(C(OH)R^f)-P(O)(OR^f)OR^g$, $-S-P(O)(OR^f)OR^g$, tetrazole, $-SO_2NHR^f$, $-SO_3$, $-CONHR^f$, $-Si(OH)_2$, or $-B(OH)_2$;

W is $-CR^fR^g-$, $-NR^f-$, $-O-$, $-S-$, $-SO-$, or $-SO_2-$;

Cy is cycloalkyl, cycloalkenyl, heterocyclyl, aryl, or heteroaryl; wherein Cy is optionally substituted by 1-6 substituents selected from the group consisting of hydrogen, halo, hydroxy, nitro, cyano, $-NR^fR^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, haloalkoxy, cycloalkylalkoxy, cycloalkenylalkoxy, heterocyclylalkoxy, aryloxy, arylalkoxy, heteroaryloxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, and heteroaryl;

$L^1$ is —$CH_2$—, —CHF—, or —$CF_2$—;

$Z^4$ is hydrogen, halo, alkyl, haloalkyl, alkenyl, haloalkenyl, alkynyl, or —$OR^f$;

or $Z^4$ is —$CH_2$— bound to the carbon atom to which Y is bound;

or $L^1$, $Z^4$, Y, and the atoms to which they are bound form a 4-7 membered cycloalkyl group or a 4-7 membered heterocyclyl group having 1 or 2 heteroatoms selected from 0 and N;

$R^a$ is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —$CF_3$, —OH, —$NO_2$, alkyl, —$OCF_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

$R^b$ is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —$CF_3$, —OH, —$NO_2$, alkyl, —$OCF_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

or $R^b$ and $Z^4$ are taken to together to form —C(O)O— or =C($R^f$)O—;

$R^c$ is alkyl, aryl, trifluoromethyl, methylsulfonyl, trifluoromethylsulfonyl, p-tolylsulfonyl, or a group selected such that —$OCOR^c$ is a good leaving group;

each $R^f$, independently, is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —$CF_3$, —OH, —$NO_2$, alkyl, —$OCF_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

each $R^g$, independently, is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —$CF_3$, —OH, —$NO_2$, alkyl, —$OCF_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

wherein the aryl is a monocyclic, bicyclic, or tricyclic carbocyclic ring system having one or two aromatic rings; the heteroaryl is a mono- or bicyclic cyclic ring system containing one, two, or three heteroatoms, wherein the heteroatoms are independently selected from oxygen, sulfur, and nitrogen; and the heterocyclyl is a mono- or bicyclic carbocyclic ring system containing one, two, three, or four heteroatoms, wherein the heteroatoms are independently selected from oxygen, sulfur, and nitrogen.

26. The pharmaceutical composition of claim 25, wherein Y is —OH or —O—P(O)($OR^f$)$OR^g$.

27. The pharmaceutical composition of claim 25, wherein the compound is represented by formula (II):

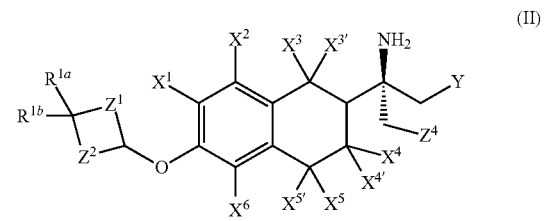

(II)

or a pharmaceutically acceptable salt thereof, wherein:

$X^1$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —$NR^fR^g$, —$N(R^f)SO_2R^g$, —$SO_2R^f$, —$SO_2NR^fR^g$, —$CO_2R^f$, trialkylamino, aryl, or heteroaryl;

$X^2$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —$NR^fR^g$, —$N(R^f)SO_2R^g$, —$SO_2R^f$, —$SO_2NR^fR^g$, —$CO_2R^f$, trialkylamino, aryl, or heteroaryl;

$X^3$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —$NR^fR^g$, —$N(R^f)SO_2R^g$, —$SO_2R^f$, —$SO_2NR^fR^g$, —$CO_2R^f$, trialkylamino, aryl, or heteroaryl;

$X^{3'}$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —$NR^fR^g$, —$N(R^f)SO_2R^g$, —$SO_2R^f$, —$SO_2NR^fR^g$, —$CO_2R^f$, trialkylamino, aryl, or heteroaryl;

$X^4$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —$NR^fR^g$, —$N(R^f)SO_2R^g$, —$SO_2R^f$, —$SO_2NR^fR^g$, —$CO_2R^f$, trialkylamino, aryl, or heteroaryl;

$X^{4'}$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —$NR^fR^g$, —$N(R^f)SO_2R^g$, —$SO_2R^f$, —$SO_2NR^fR^g$, —$CO_2R^f$, trialkylamino, aryl, or heteroaryl;

$X^5$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —$NR^fR^g$, —$N(R^f)SO_2R^g$, —$SO_2R^f$, —$SO_2NR^fR^g$, —$CO_2R^f$, trialkylamino, aryl, or heteroaryl;

$X^{5'}$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

$X^6$ is hydrogen, halo, hydroxy, nitro, cyano, alkyl, haloalkyl, cycloalkyl, halocycloalkyl, alkoxy, haloalkoxy, cycloalkoxy, halocycloalkoxy, acyl, aminoacyl, —NR$^f$R$^g$, —N(R$^f$)SO$_2$R$^g$, —SO$_2$R$^f$, —SO$_2$NR$^f$R$^g$, —CO$_2$R$^f$, trialkylamino, aryl, or heteroaryl;

Y is —OR$^f$, —(CR$^f$R$^g$)OR$^f$, —(CR$^f$R$^g$)$_2$OR$^f$, —O—P(O)(OR$^f$)OR$^g$, —OC(O)OR$^c$, —C(O)OR$^c$, —(CR$^f$R$^g$)—P(O)(OR$^f$)OR$^g$, —(C(OH)R$^f$)—P(O)(OR$^f$)OR$^g$, —S—P(O)(OR$^f$)OR$^g$, tetrazole, —SO$_2$NHR$^f$, —SO$_3$, —CONHR$^f$, —Si(OH)$_2$, or —B(OH)$_2$;

$Z^4$ is hydrogen, halo, alkyl, haloalkyl, alkenyl, haloalkenyl, alkynyl, or —OR$^f$;

or $Z^4$ is —CH$_2$— bound to the carbon atom to which Y is bound;

or $Z^4$, Y, and the atoms to which they are bound form a 4-7 membered cycloalkyl group or a 4-7 membered heterocyclyl group having 1 or 2 heteroatoms selected from 0 and N;

R$^c$ is alkyl, aryl, trifluoromethyl, methylsulfonyl, trifluoromethylsulfonyl, p-tolylsulfonyl, or a group selected such that —OCOR$^c$ is a good leaving group;

each R$^f$, independently, is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

each R$^g$, independently, is hydrogen, alkyl, haloalkyl, alkenyl, alkynyl, cycloalkyl, cycloalkenyl, aryl, heteroaryl, or heterocyclyl; wherein each of alkyl, cycloalkyl, cycloalkenyl, aryl, heteroaryl and heterocycle are optionally substituted with 1 to 5 substituents independently selected from the group consisting of halo, oxo, —CN, —CHO, —CF$_3$, —OH, —NO$_2$, alkyl, —OCF$_3$, alkoxy, cycloalkoxy, cycloalkenoxy, amino, alkylamino, dialkylamino, acylamino, aminoacyl, alkylsulfonyl, alkylaminosulfonyl, and dialkylaminosulfonyl;

$R^{1a}$ and $R^{1b}$, independently, are hydrogen, halo, hydroxy, nitro, cyano, —NR$^f$R$^g$, alkyl, haloalkyl, cycloalkyl, cycloalkenyl, cycloalkylalkyl, cycloalkenylalkyl, heterocyclylalkyl, arylalkyl, heteroarylalkyl, alkoxy, cycloalkylalkoxy, cycloalkenylalkoxy, heterocyclylalkoxy, arylalkoxy, heteroarylalkoxy, acyl, cycloalkylacyl, cycloalkenylacyl, heterocyclylacyl, arylacyl, heteroarylacyl, thioalkyl, alkenyl, alkynyl, cycloalkenyl, heterocyclyl, aryl, or heteroaryl;

or $R^{1a}$ and $R^{1b}$, when taken together, are C$_2$-C$_5$ alkylene optionally terminated by or interrupted by 1 or 2 oxygen atoms, or C$_2$-C$_5$ alkenylene optionally terminated by or interrupted by 1 or 2 oxygen atoms;

$Z^1$ is a bond, —[C(R$^d$R$^e$)]$_x$, or —CR$^d$=CR$^e$—;

$Z^2$ is a bond, —[C(R$^d$R$^e$)]$_x$, or —CR$^d$=CR$^e$—;

each of x and y, independently is 1 to 3;

each R$^d$, independently, is H, halo, hydroxyl, alkyl, alkenyl, alkoxy, or cycloalkyl;

each R$^e$, independently, is H, halo, hydroxyl, alkyl, alkenyl, alkoxy, or cycloalkyl;

wherein the aryl is a monocyclic, bicyclic, or tricyclic carbocyclic ring system having one or two aromatic rings; the heteroaryl is an optionally substituted mono- or bicyclic cyclic ring system containing one, two, or three heteroatoms, wherein the heteroatoms are independently selected from oxygen, sulfur, and nitrogen; and the heterocyclyl is an optionally substituted mono- or bicyclic carbocyclic ring system containing one, two, three, or four heteroatoms, wherein the heteroatoms are independently selected from oxygen, sulfur, and nitrogen.

28. The pharmaceutical composition of claim 27, wherein Y is —OH or —O—P(O)(OR$^f$)OR$^g$.

29. The pharmaceutical composition of claim 27, wherein the compound is represented by the following formula:

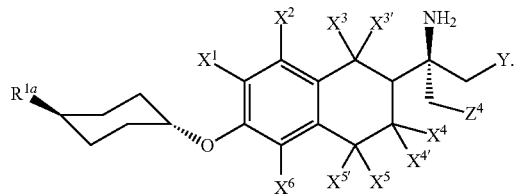

or a pharmaceutically acceptable salt thereof.

* * * * *